(12) United States Patent
Macias

(10) Patent No.: US 6,576,654 B1
(45) Date of Patent: Jun. 10, 2003

(54) METHOD FOR THE TREATMENT OF CYSTIC FIBROSIS

(75) Inventor: William Louis Macias, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/508,209

(22) PCT Filed: Sep. 23, 1998

(86) PCT No.: PCT/US98/19906

§ 371 (c)(1), (2), (4) Date: Mar. 8, 2000

(87) PCT Pub. No.: WO99/16453

PCT Pub. Date: Apr. 8, 1999

(51) Int. Cl.$^7$ .............................................. A61K 31/405
(52) U.S. Cl. ........................................ 514/415; 514/851
(58) Field of Search .................................. 514/415, 851

(56) References Cited

U.S. PATENT DOCUMENTS

| 5,405,852 | A |   | 4/1995  | Veale et al. ................. 514/292 |
| 5,436,258 | A |   | 7/1995  | Blake et al. ................. 514/372 |
| 5,453,443 | A |   | 9/1995  | Perrier et al. ................ 514/570 |
| 5,532,366 | A |   | 7/1996  | Edwards et al. ......... 514/234.2 |
| 5,547,975 | A |   | 8/1996  | Talley et al. ................. 514/406 |
| 5,565,482 | A |   | 10/1996 | Talley et al. ................. 514/406 |
| 5,641,800 | A | * | 6/1997  | Bach et al. .................. 514/415 |
| 5,654,326 | A |   | 8/1997  | Bach et al. .................. 514/419 |
| 5,719,149 | A |   | 2/1998  | Finke et al. ............. 514/231.8 |
| 5,807,829 | A |   | 9/1998  | Gyorkos et al. ............... 514/18 |
| 5,972,988 | A | * | 10/1999 | Macias ....................... 514/415 |

FOREIGN PATENT DOCUMENTS

WO         9916453    *    4/1999

* cited by examiner

Primary Examiner—Kevin E. Weddington
(74) Attorney, Agent, or Firm—Roger S. Benjamin

(57) ABSTRACT

A method is disclosed for the treatment of cystic fibrosis by administering to a human in need thereof a therapeutically effective amount of an sPLA$_2$ inhibitor, such as a 1H-indole-3-glyoxylamide.

1 Claim, No Drawings

METHOD FOR THE TREATMENT OF CYSTIC FIBROSIS

FIELD OF THE INVENTION

The present invention is directed to a method for treating cystic fibrosis. More specifically, the present invention is directed to a method for treating the symptoms of cystic fibrosis by administering a therapeutically effective amount of an $sPLA_2$ inhibitor.

BACKGROUND OF THE INVENTION

Cystic fibrosis is a hereditary disorder of the lungs, digestive, and reproductive systems. One in 2500 people in the general population in America are born with cystic fibrosis. It typically appears in early childhood and is a lifelong illness that generally gets more severe with age. Average life expectancy and quality of life are significantly reduced. There is no cure for cystic fibrosis at this time.

In cystic fibrosis the glands which produce mucus, saliva, and intestinal fluids do not work properly. Thick mucus in the lungs interferes with removal of pollutants and can cause breathing problems, infections, and lung damage. Thick secretions also may clog the pancreatic duct and block transfer of enzymes from the pancreas to the intestine. These enzymes help break down food so the body has proper growth and weight gain.

Males with cystic fibrosis are usually infertile and females may have reduced fertility due to thick secretions in the reproductive tract.

Major therapies for cystic fibrosis include the following:
1. gene therapy
2. breathing exercises
3. agents that degrade the high concentration of DNA in cystic fibrosis, e.g., human recombinant DNAse
4. drugs to restore salt and water balance, e.g., amiloride, triphosphite nucleotides
5. antibiotics for lung infection
6. inhaled beta-adrenergic agonists
7. pancreatic enzymes are taken with meals U.S. Pat. No. 5,453,443 describes bis(aryloxy)alkanes as inhibitors of phopholipase $A_2$ enzymes useful for a list of many disease states, inclusive of cystic fibrosis.

The mechanism of action for airway inflammation in cystic fibrosis remains poorly understood, but arachidonic acid may have a role (see, "Cystic Fibrosis Gene Mutation (dF508) is Associated with Intrinsic Abnormality in $Ca_2^+$— Induced Arachiodonic Acid Release by Eoithelial Cells" by Miele, L.; Cordella-Miele, Eleonora; Xing, Mingzhao; Frizzell, R.; Mukherjee, Anil., *DNA and Cell Biology*, Vol 16, No. 6, 1997, Many Ann Liebert, Inc., pp. 749–759).

U.S. Pat. No. 5,654,326 describes the use of 1H-indole-3-glyoxylamide sPLA2 inhibitors to inhibit the sPLA2 mediated release of fatty acid.

Accordingly, there is a substantial need for a novel effective, and easy to administer treatment for the many symptoms of cystic fibrosis. It is therefore an object of the present invention to provide a methodology for effectively treating cystic fibrosis.

SUMMARY OF THE INVENTION

This invention is a method of alleviating the symptoms of a human afflicted with cystic fibrosis by administering a therapeutically effective amount of a selected $sPLA_2$ inhibitor.

Is This invention is also a method of facilitating the clearance of retained pulmonary secretions in a human afflicted with cystic fibrosis.

This invention is also a method of facilitating lung mucus clearance in a human afflicted with cystic fibrosis.

This invention is also a method of inhibiting inflammation in the lungs in a human afflicted with cystic fibrosis.

This invention is also the use of $sPLA_2$ inhibitors to reduce the complications of acute or chronic infections of the respiratory tree in a human afflicted with cystic fibrosis.

This invention is also the use of $sPLA_2$ inhibitors for the manufacture of a medicament for the prophylactic or therapeutic treatment of a human afflicted with cystic fibrosis.

DETAILED DESCRIPTION OF THE INVENTION

Definitions

General Definitions

The term, "therapeutically effective amount" is a quantity of $sPLA_2$ inhibitor sufficient to significantly alleviate symptoms of cystic fibrosis in a human.

The term, "parenteral" means not through the alimentary canal but by some other route such as subcutaneous, intramuscular, intraorbital, intracapsular, intraspinal, intrasternal, or intravenous.

The term, "active compound" means one or more $sPLA_2$ inhibitors used in the method of the invention.

I. $sPLA_2$ INHIBITORS USEFUL IN THE METHOD OF THE INVENTION

Selected classes of secretary phopholipase $A_2$ ($sPLA_2$) inhibitors are useful in the practice of the method of this invention.

Exemplary of classes of suitable $sPLA_2$ useful in the the method of the invention for treatment of cystic fibrosis are the following:

1H-indole-3-glyoxylamides
1H-indole-3-hydrazides
1H-indole-3-acetamides
1H-indole-1-glyoxylamides
1H-indole-1-hydrazides
1H-indole-1-acetamides
indolizine-1-acetamides
indolizine-1-acetic acid hydrazides
indolizine-1-glyoxylamides
indene-1-acetamides
indene-1-acetic acid hydrazides
indene-1-glyoxylamides
carbazoles & tetrahydrocarbazoles
pyrazoles
phenyl glyoxamides
pyrroles
naphthyl glyoxamides
phenyl acetamides
naphthyl acetamides Each of the above $sPLA_2$ inhibitor types is discussed in the following sections (a) through (m) wherein details of their molecular configuration are given along with methods for their preparation.

a) The 1H-indole-3-glyoxylamide sPLA$_2$ inhibitors and method of making them are described in U.S. Pat. No. 5,654,326, the entire disclosure of which is incorporated herein by reference. Another method of making 1H-indole-3-glyoxylamide sPLA$_2$ inhibitors is described in U.S. patent application Ser. No. 09/105,381, filed Jun. 26, 1998 and titled, "Process for Preparing 4-substituted 1-H-Indole-3-glyoxyamides" the entire disclosure of which is incorporated herein by reference. U.S. patent application Ser. No. 09/105,381 discloses the following process having steps (a) thru (i):

Preparing a compound of the formula I or a pharmaceutically acceptable salt or prodrug derivative thereof

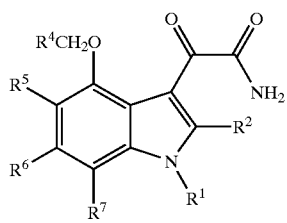

(I)

wherein:

R$^1$ is selected from the group consisting of —C$_7$–C$_{20}$ alkyl,

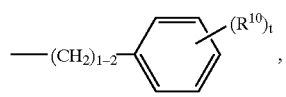

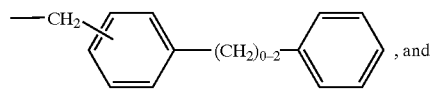, and

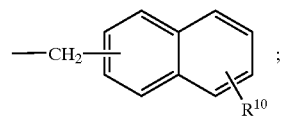;

where

R$^{10}$ is selected from the group consisting of halo, C$_1$–C$_{10}$ alkyl, C$_1$–C$_{10}$ alkoxy, —S—(C$_1$–C$_{10}$ alkyl) and halo(C$_1$–C$_{10}$)alkyl, and t is an integer from 0 to 5 both inclusive;

R$^2$ is selected from the group consisting of hydrogen, halo, C$_1$–C$_3$ alkyl, C$_3$–C$_4$ cycloalkyl, C$_3$–C$_4$ cycloalkenyl, —O—(C$_1$–C$_2$ alkyl), —S—(C$_1$–C$_2$ alkyl), aryl, aryloxy and HET;

R$^4$ is selected from the group consisting of —CO$_2$H, —SO$_3$H and —P(O)(OH)$_2$ or salt and prodrug derivatives thereof; and R$^5$, R$^6$ and R$^7$ are each independently selected from the group consisting of hydrogen, (C$_1$–C$_6$)alkyl, (C$_1$–C$_6$) alkoxy, halo(C$_1$–C$_6$)alkoxy, halo(C$_2$–C$_6$)alkyl, bromo, chloro, fluoro, iodo and aryl;

which process comprises the steps of:

a) halogenating a compound of formula X

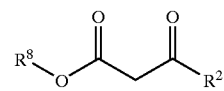

X where

R$^8$ is (C$_1$–C$_6$)alkyl, aryl or HET;

with SO$_2$Cl$_2$ to form a compound of formula IX

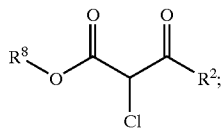

IX b) hydrolyzing and decarboxylating a compound of formula IX

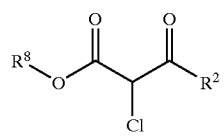

IX to form a compound of formula VIII

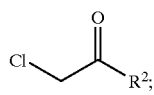

VIII c) alkylating a compound of formula VII

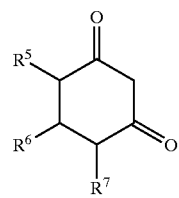

VII with a compound of formula VIII

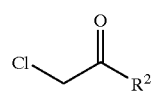

VIII to form a compound of formula VI

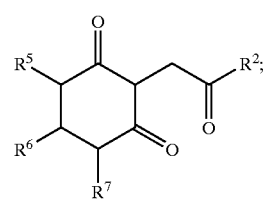

VI d) aminating and dehydrating a compound of formula VI

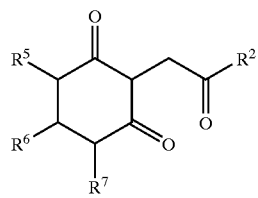

with an amine of the formula $R^1NH_2$ in the presence of a solvent that forms and azeotrope with water to form a compound of formula V;

e) oxidizing a compound of formula V

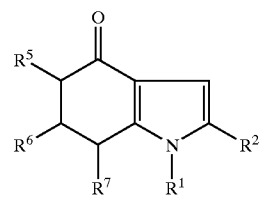

by refluxing in a polar hydrocarbon solvent having a boiling point of at least 150° C. and a dielectric constant of at least 10 in the presence of a catalyst to form a compound of formula IV

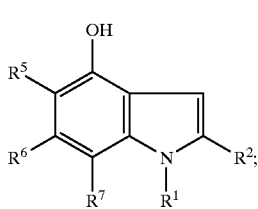

f) alkylating a compound of the formula IV

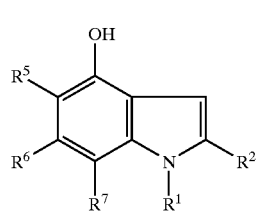

with an alkylating agent of the formula $XCH_2R^{4a}$ where X is a leaving group and $R^{4a}$ is $-CO_2R^{4b}$, $-SO_3R^{4b}$, $-P(O)(OR^{4b})_2$, or $-P(O)(OR^{4b})H$, where $R^{4b}$ is an acid protecting group to form a compound of formula III

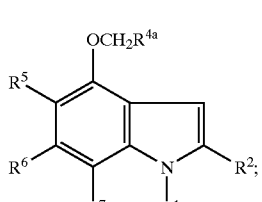

g) reacting a compound of formula III

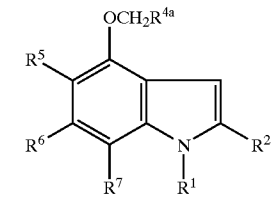

with oxalyl chloride and ammonia to form a compound of formula II

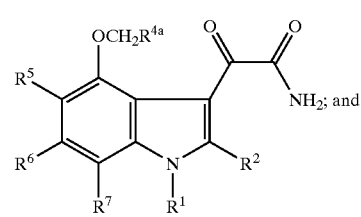

h) optionally hydrolyzing a compound of formula II

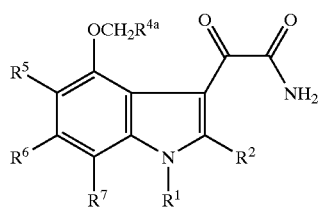

to form a compound of formula I; and i) optionally salifying a compound of formula I.

The synthesis methodology for making the 1H-indole-3-glyoxylamide sPLA$_2$ inhibitor starting material may be by any suitable means available to one skilled in the chemical arts. However, such methodology is not part of the present invention which is a method of use, specifically, a method of treating mammal afflicted or susceptible to cystic fibrosis.

The method of the invention is for treatment of a mammal, including a human, afflicted with cystic fibrosis, said method comprising administering to said human a therapeutically effective amount of the compound represented by formula (Ia), or a pharmaceutically acceptable salt or prodrug derivative thereof;

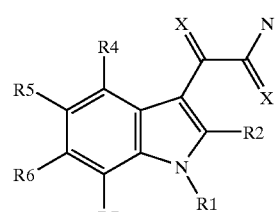

wherein;
both X are oxygen;
$R_1$ is selected from the group consisting of

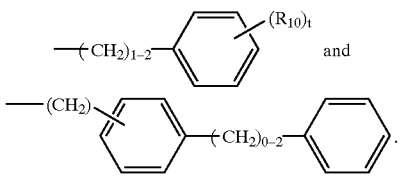

where
$R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, —($L_a$)-(acidic group); wherein —($L_a$)— is an acid linker; provided, the acid linker group, —($L_a$)—, for $R_4$ is selected from the group consisting of;

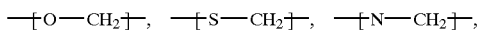

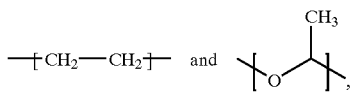

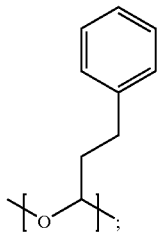

and provided, the acid linker, —($L_a$)—, for $R_5$ is selected from group consisting of;

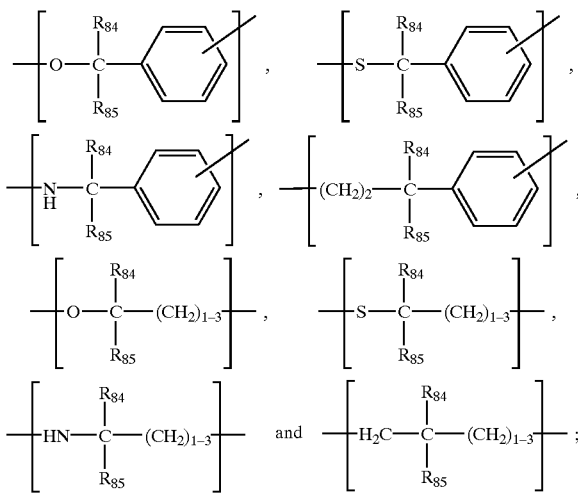

wherein
$R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)-(acidic group) and wherein the (acidic group) on the group —($L_a$)-(acidic group) of $R_4$ or $R_5$ is selected from —$CO_2H$, —$SO_3H$, or —$P(O)(OH)_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O—($C_1$–$C_6$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

Preferred for practicing the method of the invention are 1H-indole-3-glyoxylamide compounds and all corresponding pharmaceutically acceptable salts, solvates and prodrug derivatives thereof which are useful in the method of the invention include the following:

(A) [[3-(2-Amino-1,2-dioxoethyl)-2-methyl-1-(phenylmethyl)-1H-indol-4-yl]oxy]acetic acid,
(B) dl-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid
(G) [[3-(2-Amino-1,2-dioxoethyl)-1-[4(-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid,
(P) mixtures of (A) through (P) in any combination.

Particularly useful prodrugs of the compounds of formula (I) and named compounds (A) thru (O) are the simple aromatic and aliphatic esters, such as the methyl ester, ethyl ester, n-propyl ester, isopropyl ester, n-butyl ester, sec-butyl, tert-butyl ester, N,N-diethylglycolamido ester, and morpholino-N-ethyl ester. Methods of making ester prodrugs are disclosed in U.S. Pat. No. 5,654,326. Additional methods of prodrug synthesis are disclosed in U.S. Provisional Patent Application Serial No. 60/063280 filed Oct. 27, 1997 (titled, N,N-diethylglycolamido ester Prodrugs of Indole sPLA2 Inhibitors), the entire disclosure of which is incorporated herein by reference; U.S. Provisional Patent Application Serial No. 60/063646 filed Oct. 27, 1997 (titled, Morpholino-N-ethyl Ester Prodrugs of Indole sPLA2 Inhibitors), the entire disclosure of which is incorporated herein by reference; and U.S. Provisional Patent Application Serial No. 60/063284 filed Oct. 27, 1997 (titled, Isopropyl Ester Prodrugs of Indole sPLA$_2$ Inhibitors), the entire disclosure of which is incorporated herein by reference.

Most preferred in the practice of the method of the invention are the acid, sodium salt, methyl ester, and morpholino-N-ethyl ester forms of [[3-(2-Amino-1,2-dioxoethyl)-2-ethyl-1-(phenylmethyl)-1H-indol-4-yl]oxy] acetic acid as represented by the following formulae:

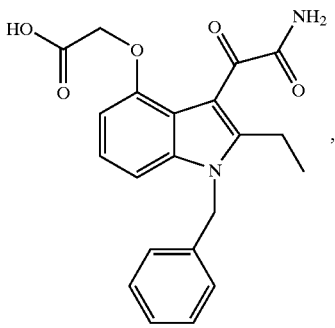

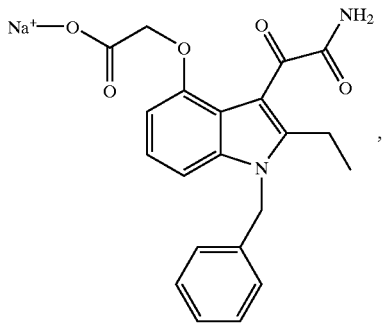

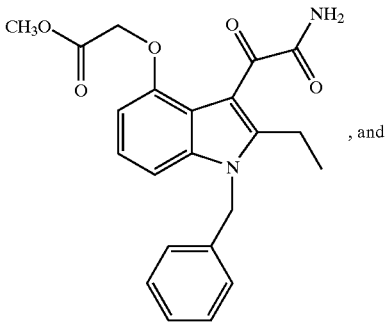

, and

Another highly preferred compound is the indole-3-glyoxylamide morpholino ethyl ester of represented by the formula:

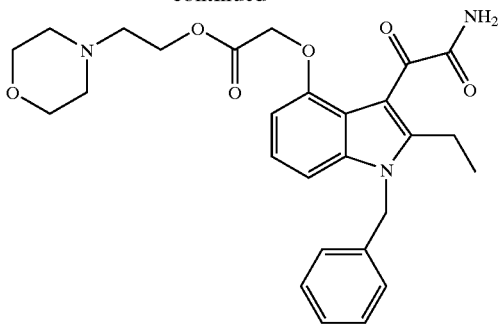

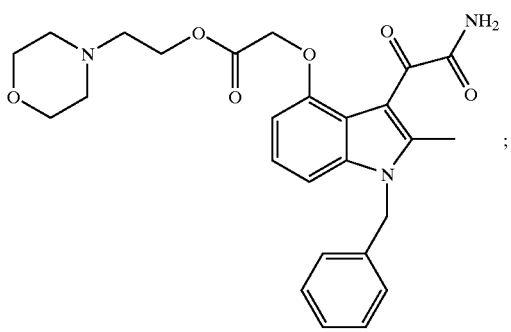

;

the preparation of which is further described in United States provisional patent application SNo. 60/063,646 filed Oct. 27, 1997. Synthesis methods for 1H-indole-3-glyoxylamide sPLA$_2$ inhibitors are additionally depicted in the following reaction scheme:

Reaction Scheme 1H-indole-3-glyoxylamide

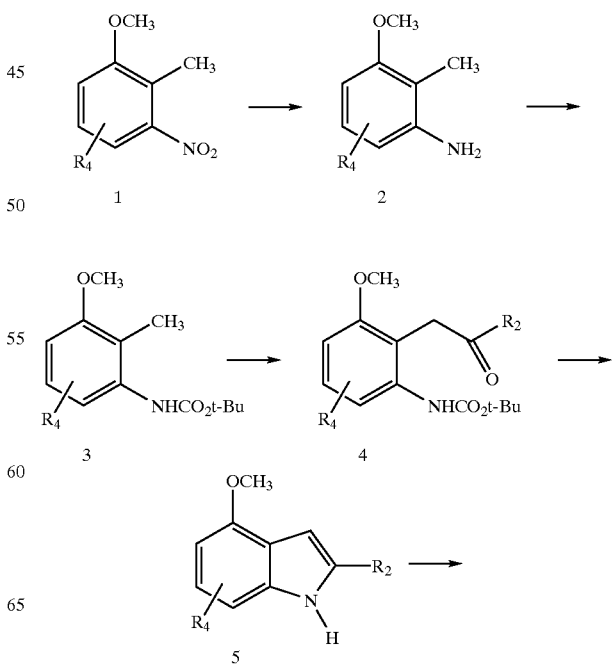

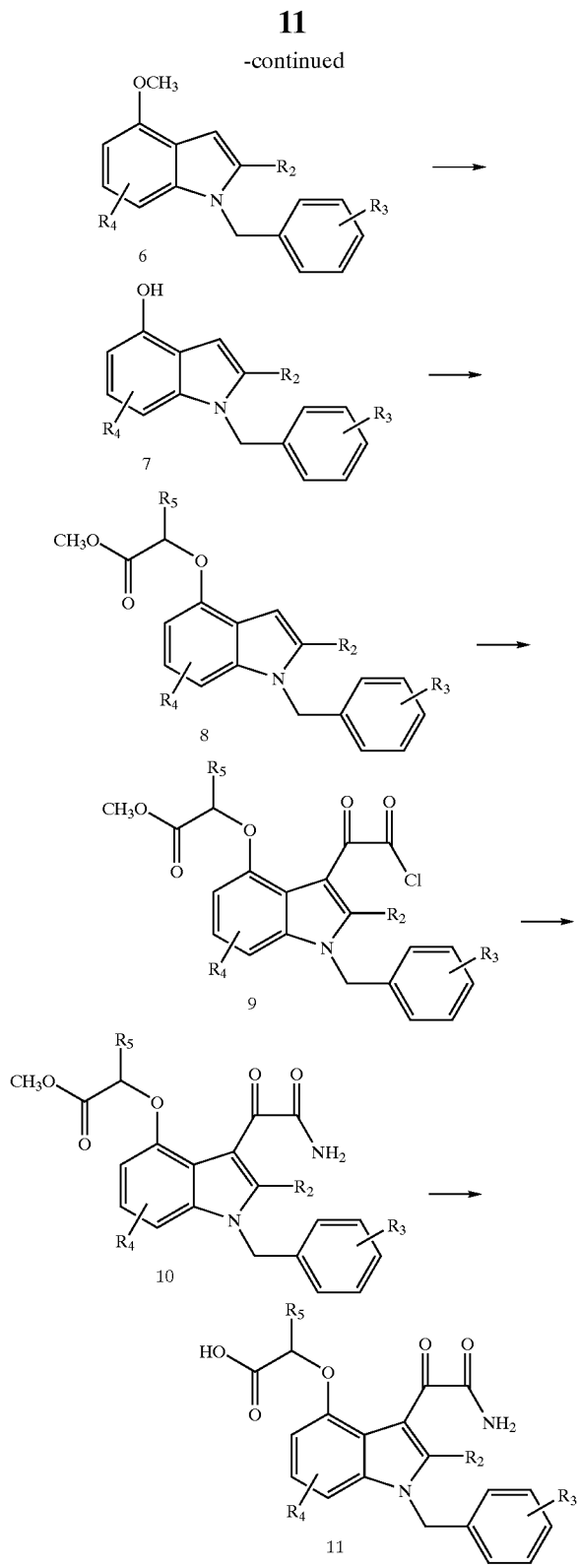

nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at −40 to −20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, Adv. Drug Res., 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The a-[(indol-4-yl)oxy]alkanoic acid ester, 8, is reacted with oxalyl chloride in methylene chloride to give 9, which is not purified but reacted directly with ammonia to give the glyoxamide 10. This product is hydrolyzed using 1N sodium hydroxide in MeOH. The final glyoxylamide, 11, is isolated either as the free carboxylic acid or as its sodium salt or in both forms.

The most preferred compound, [[3-(2-Amino-1,2-dioxoethyl)-2-ethyl-1-(phenylmethyl)-1H-indol-4-yl]oxy] acetic acid (as well as its sodium salt and methyl ester) useful in the practice of the method of the invention, may be prepared by the following procedure:

Preparation of [[3-(2-Amino-1,2-dioxoethyl)-2-ethyl-1-(phenylmethyl)-1H-indol-4-yl]oxy]acetic acid, a compound represented by the formula:

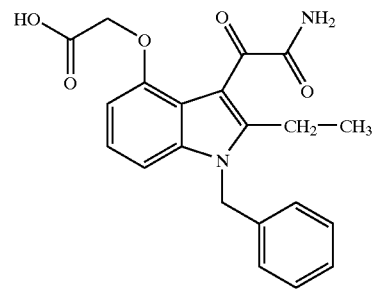

Part A. Preparation of 2-Ethyl-4-methoxy-1H-indole

A solution of 140 mL (0.18 mol) of 1.3M sec-butyl lithium in cyclohexane is added slowly to N-tert-butoxycarbonyl-3-methoxy-2-methylaniline (21.3 g, 0.09 mol) in 250 mL of THF keeping the temperature below −40° C. with a dry ice-ethanol bath. The bath is removed and the temperature allowed to rise to 0° C. and then the bath replaced. After the temperature has cooled to −60° C., 18.5 g (0.18 mmol) of N-methoxy-N-methylpropanamide in an equal volume of THF iss added dropwise. The reaction mixture is stirred 5 minutes, the cooling bath removed and stirred an additional 18 hours. It is then poured into a Explanation of Reaction Scheme To obtain the glyoxylamides substituted in the 4-position with an acidic function through an oxygen atom, the reactions outlined in scheme 1 are used (for conversions 1 through 5, see ref. Robin D. Clark, Joseph M. Muchowski, Lawrence E. Fisher, Lee A. Flippin, David B. Repke, Michel Souchet, *Synthesis,* 1991, 871–878, the disclosures of which are incorporated herein by reference). The ortho-mixture of 300 mL of ether and 400 mL of 0.5N HCl. The organic layer is separated, washing with water, brine, dried over $MgSO_4$, and concentrated at reduced pressure to give 25.5 g of a crude of 1-[2-(tert-butoxycarbonylamino)-6-methoxyphenyl]-2-butanone. This material is dissolved in 250 mL of methylene chloride and 50 mL of trifluoroacetic acid and stirred for a total of 17 hours. The mixture is concentrated at reduced pressure and ethyl acetate and water added to the remaining oil. The ethyl acetate is separated, washed with brine, dried ($MgSO_4$) and concentrated. The residue is chromatographed three times on silica eluting with 20% EtOAc/hexane to give 13.9 g of 2-ethyl-4-methoxy-1H-indole.

Analysis for $C_{11}H_{13}NO$:
Calculated: C, 75.40; H, 7.48; N, 7.99; Found: C, 74.41; H, 7.64; N, 7.97.

Part B. Preparation of 2-Ethyl-4-methoxy-1-(phenylmethyl)-1H-indole

2-Ethyl-4-methoxy-1H-indole (4.2 g, 24 mmol) is dissolved in 30 mL of DMF and 960 mg (24 mmol) of 60% NaH/mineral oil is added. After 1.5 hours, 2.9 mL (24 mmol) of benzyl bromide is added. After 4 hours, the mixture is diluted with water extracting twice with ethyl acetate. The combined ethyl acetate is washed with brine, dried ($MgSO_4$) and concentrated at reduced pressure. The residue is chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole

A solution of 3.1 g (11.7 mmol) of 2-ethyl-4-methoxy-1-(phenylmethyl)-1H-indole and 48.6 mL of 1M $BBr_3/CH_2Cl_2$ in 50 mL of methylene chloride is stirred at room temperature for 5 hours and concentrated at reduced pressure. The residue is dissolved in ethyl acetate, washed with brine and dried ($MgSO_4$). After concentrating at reduced pressure, the residue is chromatographed on silica gel eluting with 20% EtOAc/hexane to give 1.58 g (54% yield) of 2-ethyl-4-hydroxy-1-(phenylmethyl)-1H-indole, mp, 86–90 ° C.

Analysis for $C_{17}H_{17}NO$:
Calculated: C, 81.24; H, 6.82; N, 5.57; Found: C, 81.08; H, 6.92; N, 5.41.

Part D. Preparation of [[2-Ethyl-1-(phenylmethyl)-1H-indol-4-yl]oxy]acetic acid tert-butyl ester 2-Ethyl-4-hydroxy-1-(phenylmethyl)-1H-indole (5.82 g, 20 mmol) is added to 7.82 g (24 mmol) cesium carbonate in 25 mL DMF and the mixture is stirred at 35° C. for 30 minutes. After cooling to 20° C., a solution of tert-butyl bromoacetate (4.65 g, 23.8 mmol) in 5 mL DMF is added and stirring maintained until the reaction is judged complete by TLC analysis (several hours). The mixture is diluted with water and extracted with ethyl acetate. The ethyl acetate solution is washed with brine, dried ($MgSO_4$) and concentrated at reduced pressure to give 6.8 g of solid.

Mass spectrum: 365
Analyses for $C_{23}H_{27}NO_3$:
Calculated: C, 75.59; H, 7.75; N, 3.83; Found: C, 75.87; H, 7.48; N, 3.94.

Part E. Preparation of [[2-Ethyl-1-(phenylmethyl)-3-ureido-1H-indol-4-yl]oxy]acetic acid tert-butyl ester A solution of 2.3 g (6.3 mmol) [[2-ethyl-1-(phenylmethyl)-1H-indol-4-yl]oxy]acetic acid tert-butyl ester and 4.8 g (12.6 mmol) bis(2,2,2-trichloroethyl)-azodicarboxylate in diethyl ether is stirred for 24 hours at room temperature. The resulting solid is filtered and vacuum dried. This adduct (1 g, 1.3 mmol) is dissolved in 10 mL of THF and treated with zinc (1 g) and glacial acetic acid (0.5 mL). After stirring for 30 minutes at room temperature an excess of trimethylsilylisocyanate in 1 mL of THF is added and stirring is continued at room temperature for 18 hours. The mixture is diluted with water and extracted with ethyl acetate. The organic layer is washed with brine, dried over $MgSO_4$ and concentrated to dryness to give 0.385 g (69% yield) of the subtitled material. Mass spectrum: 423.

Analyses for $C_{24}H_{29}N_3O_4$:
Calculated: C, 68.07; H, 6.90; N, 9.92; Found: C, 67.92; H, 6.84; N, 9.70.

Part F. Preparation of [[3-(2-Amino-1,2-dioxoethyl)-2-ethyl-1-(phenylmethyl)-1H-indol-4-yl]oxy]acetic acid A mixture of 788 mg (2 mmol) of [3-(2-amino-1,2-dioxoethyl)-2-ethyl-1-(phenylmethyl)-1H-indol-4-yl]oxy]-acetic acid methyl ester, 10 mL of 1n NaOH and 30 mL of MeOH is heated to maintain reflux for 0.5 hour, stirred at room temperature for 0.5 hour and concentrated at reduced pressure. The residue is taken up in ethyl acetate and water, the aqueous layer separated and made acidic to pH 2–3 with 1N HCl. The precipitate is filtered and washed with ethyl acetate to give 559 mg (74% yield) of [[3-(2-amino-1,2-dioxoethyl)-2-ethyl-1-(phenylmethyl)-1H-indol-4-yl]oxy] acetic acid, mp, 230–234° C.

Analyses for $C_{21}H_{20}N_2O_5$:
Calculated: C, 65.96; H, 5.80; N, 7.33; Found: C, 66.95; H, 5.55; N, 6.99.

b) 1H-indole-3-hydrazide $sPLA_2$ inhibitors useful in practicing the method of the invention are described in U.S. Pat. No. 5,578,634; the entire disclosure of which is incorporated herein by reference. The method of the invention is for treatment of a mammal, including a human, afflicted with cystic fibrosis, said method comprising administering to said human a therapeutically effective amount of the described as 1H-indole-3-acetic acid hydrazides represented by the formula (Ib), and pharmaceutically acceptable salts, and prodrugs thereof;

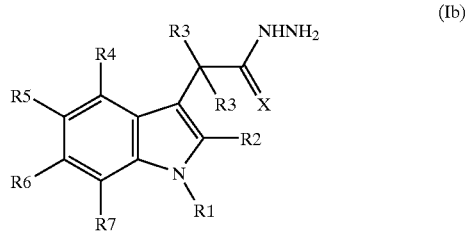
(Ib)

wherein;

X is oxygen or sulfur;

$R_1$ is selected from groups (i), (ii) and (iii) where;
(i) is $C_4$–$C_{20}$ alkyl, $C_4$–$C_{20}$ alkenyl, $C_4$–$C_{20}$ alkynyl, $C_4$–$C_{20}$ haloalkyl, $C_4$–$C_{12}$ cycloalkyl, or
(ii) is aryl or aryl substituted by halo, —CN, —CHO, —OH, —SH, $C_1$–$C_{10}$ alkylthio, $C_1$–$C_{10}$ alkoxy, $C_1$–$C_{10}$ alkyl, carboxyl, amino, or hydroxyamino;
(iii) is

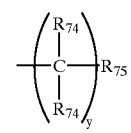

where
y is from 1 to 8, $R_{74}$ is, independently, hydrogen or $C_1$–$C_{10}$ alkyl, and $R_{75}$ is aryl or aryl substituted by halo, —CN, —CHO, —OH, nitro, phenyl, —SH, $C_1$–$C_{10}$ alkylthio, $C_1$–$C_{10}$ alkoxy, $C_1$–$C_{10}$ alkyl, amino, hydroxyamino or a substituted or unsubstituted 5- to 8-membered heterocyclic ring;

$R_2$ is halo, $C_1$–$C_3$ alkyl, ethenyl, $C_1$–$C_2$ alkylthio, $C_1$–$C_2$ alkoxy, —CHO, —CN;

each $R_3$ is independently hydrogen, $C_1$–$C_3$ alkyl, or halo;

$R_4$, $R_5$, $R_6$, and $R_7$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or any two adjacent hydrocarbyl groups in the set $R_4$, $R_5$, $R_6$, and $R_7$ combined with the ring carbon atoms to which they are attached to form a 5- or 6-membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazino, hydrazido, —$NH_2$, —$NO_2$, —$NR_{82}R_{83}$, and —C(O)$NR_{82}R_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5- to 8-membered heterocyclic ring; or a group having the formula;

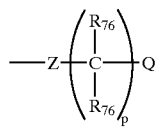

where, each $R_{76}$ is independently selected from hydrogen, $C_1$–$C_{10}$ alkyl, hydroxy, or both $R_{76}$ taken together are =O;

p is 1 to 8,

Z is a bond, —O—, —N($C_1$–$C_{10}$ alkyl)—, —NH, or —S—; and

Q is —CON($R_{82}R_{83}$), -5-tetrazolyl, —$SO_3H$,

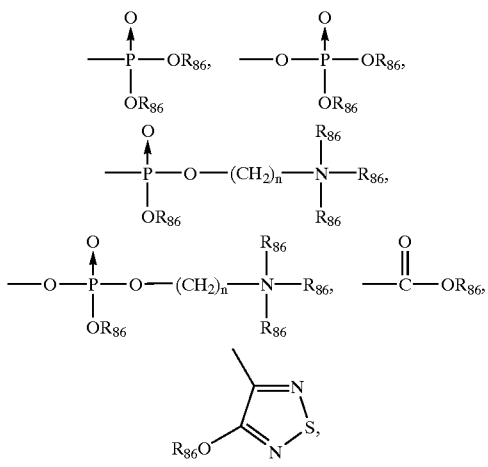

where $R_{86}$ is independently selected from hydrogen, a metal, or $C_1$–$C_{10}$ alkyl.

The synthesis of the 1H-indole-3-acetic acid hydrazides of structure (I) can be accomplished by known methods such as outlined in the following reaction schemes:

Scheme 1

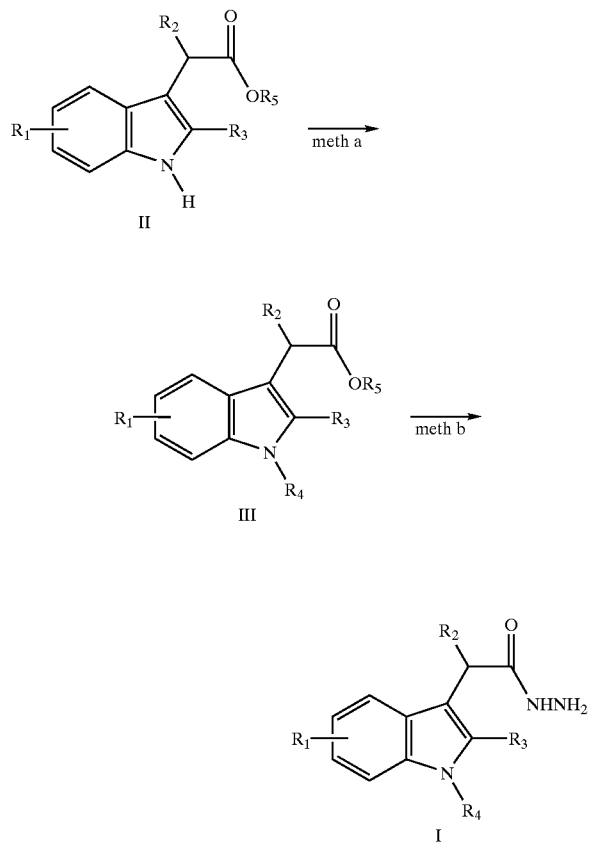

The 1H-indole-3-acetic acid ester can be readily alkylated by an alkyl halide or arylalkyl halide in a solvent such as N,N-dimethylformamide(DMF) in the presence of a base (meth a) to give the intermediate 1-alkyl-1H-indole-3-acetic acid esters, III. Bases such as potassium t-butoxide and sodium hydride were particularity useful. It is advantageous to react the indole, II, with the base to first form the salt of II and then add the alkylating agent. Most alkylations can be carried out at room temperature. Treatment of the 1-alkyl-1H-indole-3-acetic acid esters, III, with hydrazine or hydrazine hydrate in ethanol(meth b) gives the desired 1-alkyl-1H-indole-3-acetic acid hydrazides, I. This condensation to form I is usually carried out at the reflux temperature of the solvent for a period of 1 to 24 hours.

c) 1H-indole-3-acetamide sPLA$_2$ inhibitors and methods of making these inhibitors are set out in U.S. Pat. No. 5,684,034, the entire disclosure of which is incorporated herein by reference. The method of the invention is for treatment of a mammal, including a human, afflicted with cystic fibrosis, said method comprising administering to said human a therapeutically effective amount of the compound represented by (IIb), and pharmaceutically acceptable salts and prodrug derivatives thereof, (IIb)

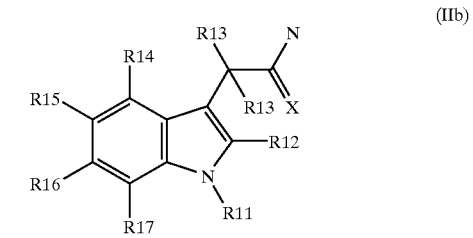

wherein;

X is oxygen or sulfur;

$R_{11}$ is selected from groups (i), (ii) (iii) and (iv) where;
- (i) is $C_6-C_{20}$ alkyl, $C_6-C_{20}$ alkenyl, $C_6-C_{20}$ alkynyl, $C_6-C_{20}$ haloalkyl, $C_4-C_{12}$ cycloalkyl, or
- (ii) is aryl or aryl substituted by halo, nitro, —CN, —CHO, OH, —SH, $C_1-C_{10}$ alkyl, $C_1-C_{10}$ alkylthio, $C_1-C_{10}$ alkoxyl, carboxyl, amino, or hydroxyamino; or
- (iii) is —$(CH_2)_n$—$(R_{80})$, or —(NH)—$(R_{81})$, where n is 1 to 8, and $R_{80}$ is a group recited in (i), and $R_{81}$ is selected from a group recited in (i) or (ii);
- (iv) is

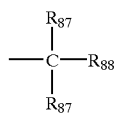

where
$R_{87}$ is hydrogen or $C_1-C_{10}$ alkyl, and $R_{88}$ is selected from the group; phenyl, naphthyl, indenyl, and biphenyl, unsubstituted or substituted by halo, —CN, —CHO, —OH, —SH, $C_1-C_{10}$ alkylthio, $C_1-C_{10}$ alkoxyl, phenyl, nitro, $C_1-C_{10}$ alkyl, $C_1-C_{10}$ haloalkyl, carboxyl, amino, hydroxyamino; or a substituted or unsubstituted 5 to 8 membered heterocyclic ring;

$R_{12}$ is halo, $C_1-C_2$ alkylthio, or $C_1-C_2$ alkoxy;

each $R^{13}$ is independently hydrogen, halo, or methyl;

$R_{14}$, $R_{15}$, $R_{16}$, and $R_{17}$ are each independently hydrogen, $C_1-C_{10}$ alkyl, $C_1-C_{10}$ alkenyl, $C_1-C_{10}$ alkynyl, $C_3-C_8$ cycloalkyl, aryl, aralkyl, or any two adjacent hydrocarbyl groups in the set $R_{14}$, $R_{15}$, $R_{16}$, and $R_{17}$, combine with the ring carbon atoms to which they are attached to form a 5 or 6 membered substituted or unsubstituted carbocyclic ring; or $C_1-C_{10}$ haloalkyl, $C_1-C_{10}$ alkoxy, $C_1-C_{10}$ haloalkoxy, $C_4-C_8$ cycloalkoxy, phenoxy, halo, hydroxy, carboxyl, —SH, —CN, $C_1-C_{10}$ alkylthio, arylthio, thioacetal, —C(O)O($C_1-C_{10}$ alkyl), hydrazide, hydrazino, hydrazido, —$NH_2$, —$NO_2$, —$NR_{82}R_{83}$, and —C(O)$NR_{82}R_{83}$, where, $R_{82}$ and $R_{83}$ are independently hydrogen, $C_1-C_{10}$ alkyl, $C_1-C_{10}$ hydroxyalkyl, or taken together with N, $R_{82}$ and $R_{83}$ form a 5- to 8-membered heterocyclic ring; or a group having the formula;

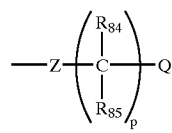

where,
$R_{84}$ and $R_{85}$ are each independently selected from hydrogen, $C_1-C_{10}$ alkyl, hydroxy, or $R_{84}$ and $R_{85}$ taken together are =O;

p is 1 to 5,

Z is a bond, —O—, —N($C_1-C_{10}$ alkyl)—, —NH—, or —S—; and

Q is —CON($R_{82}R_{83}$), -5-tetrazolyl, —$SO_3H$,

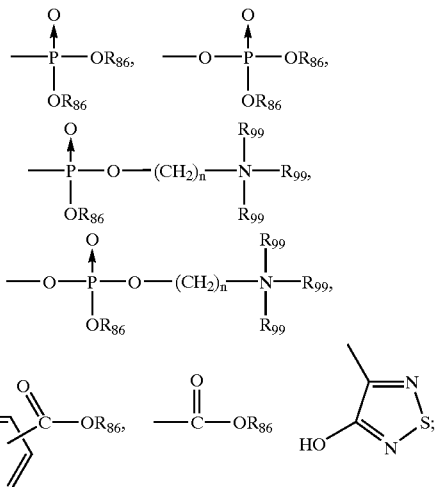

where
n is 1 to 8, $R_{86}$ is independently selected from hydrogen, a metal, or $C_1-C_{10}$ alkyl, and $R_{99}$ is selected from hydrogen or $C_1-C_{10}$ alkyl.

The synthesis of the 1H-indole-3-acetamides of structure (IIb) useful in the method of the invention can be accomplished by known methods. A procedure useful for the syntheses of these compounds is shown in the following reaction scheme:

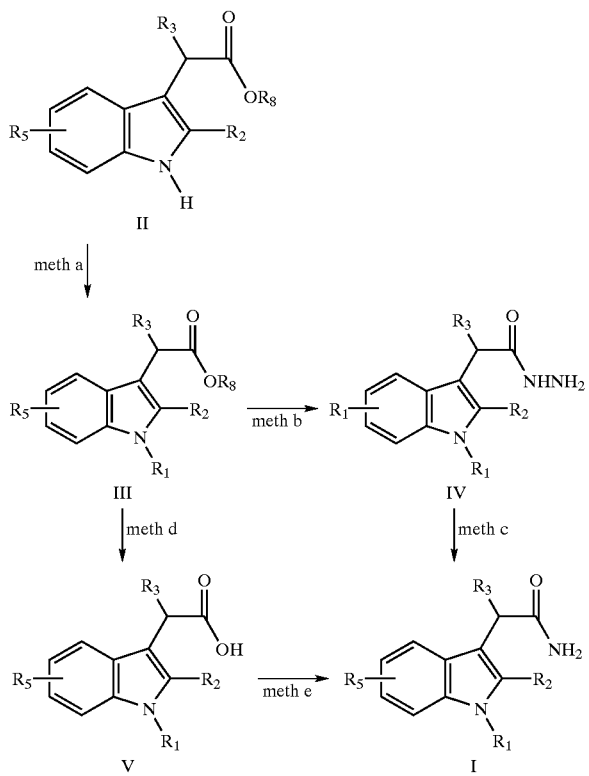

The 1H-indole-3-acetamide II may be alkylated by an alkyl halide or arylalkyl halide in a solvent such as N,N-dimethylformamide (DMF) in the presence of a base (method a) to give intermediate 1-alkyl-1H-indole-3-acetic acid esters, III. Bases such as potassium t-butoxide and sodium hydride are useful. It is advantageous to react the indole, II, with the base to first form the salt of II and then add alkylating agent. Treatment of the 1-alkyl-1H-indole-3-acetic acid esters, III, with hydrazine or hydrazine hydrate in ethanol (method b) gives the desired 1-alkyl-1H-indole-3-acetic acid hydrazides, IV. This condensation to form IV may be carried out at the reflux temperature of the solvent for a period of 1 to 24 hours. The acetic acid hydrazides, IV, are hydrogenated to give the acetamides, I, by heating with Raney nickel in ethanol (method c). The intermediate acetic acid esters, III, can be first hydrolyzed to the acetic acid derivatives, V (method d), which on treatment with an alkyl chloroformate followed by anhydrous ammonia, also give amides, I (method e).

d) 1H-indole-1-functional sPLA$_2$ inhibitors of the hydrazide, amide, or glyoxylamide types as described in U.S. Pat. No. 5,641,800, the entire disclosure of which is incorporated herein by reference. The method of the invention is for treatment of a mammal, including a human, afflicted with cystic fibrosis, said method comprising administering to said human a therapeutically effective amount of a 1H-indole-1-acetamide or a pharmaceutically acceptable salt, solvate or prodrug derivative thereof; wherein said compound is represented by the formula (Ic);

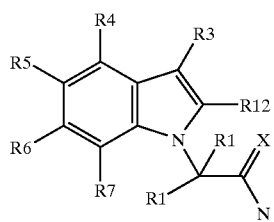

(Ic)

wherein for Formula (Ic);

X is oxygen or sulfur;

each $R_1$ is independently hydrogen, or $C_1$–$C_3$ alkyl;

$R_3$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_6$ and $R_7$ are independently selected from hydrogen, a non-interfering substituent, or the group, —($L_a$)-(acidic group); wherein —($L_a$)—, is an acid linker having an acid linker length of 1 to 10; provided, that at least one of $R_6$ and $R_7$ must be the group, —($L_a$)-(acidic group);

$R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

1H-indole-1-hydrazide compounds useful as sPLA$_2$ inhibitors in the practice of the method of the invention are as follows:

A 1H-indole-1-hydrazide compound or a pharmaceutically acceptable salt, solvate or prodrug derivative thereof;

wherein said compound is represented by the formula (IIc);

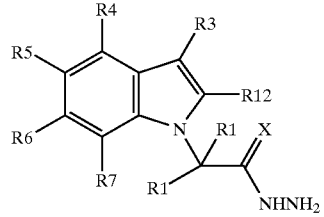

(IIc)

wherein for formula (IIc);

X is oxygen or sulfur;

each $R_1$ is independently hydrogen, or $C_1$–$C_3$ alkyl;

$R_3$ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituent; or
(c) is the group —($L_a$)—$R_{80}$; where, —($L_a$)— is a divalent linking group of 1 to 12 atoms and where $R^{80}$ is a group selected from (a) or (b);

$R^2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1† to 3 atoms other than hydrogen;

$R_6$ and $R_7$ are independently selected from hydrogen, a non-interfering substituent, or the group, —($L_a$)-(acidic group); wherein —($L_a$)—, is an acid linker having an acid linker length of 1 to 10; provided, that at least one of $R^6$ and $R_7$ must be the group, —($L_a$)-(acidic group);

$R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

e) Indolizine sPLA$_2$ inhibitors and their method of preparation are described in U.S. patent application Ser. No. 08/765,566, filed Jul. 20, 1995 (titled, "Synovial Phospholipase A2 Inhibitor Compounds Having an Indolizine Type Nucleus, Parmaceutical Formulations Containing Said compounds, and Therapeutic Methods of Using said Compounds"), the entire disclosure of which is incorporated herein by reference; and also in European Patent Publication No. 0772596, published May 14, 1997. The method of the invention is for treatment of a mammal, including a human, afflicted with cystic fibrosis, said method comprising administering to said human a therapeutically effective amount of 1H-indole-1-functional compound or a pharmaceutically acceptable salt, solvate or prodrug derivative thereof; wherein said compound is represented by the formula (Id);

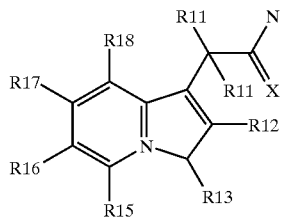

(I)

wherein;

X is oxygen or sulfur;

each $R_{11}$ is independently hydrogen, $C_1$–$C_3$ alkyl, or halo;

$R_{13}$ is selected from groups (a), (b) and (c) where;
- (a) is $C_7$–$C_{20}$ alkyl, $C_7$–$C_{20}$ alkenyl, $C_7$–$C_{20}$ alkynyl, carbocyclic radical, or heterocyclic radical, or
- (b) is a member of (a) substituted with one or more independently selected non-interfering substituents; or
- (c) is the group —($L_a$)—$R_{80}$; where, —($L_a$)— is a divalent linking group of 1 to 12 atoms and where $R_{80}$ is a group selected from (a) or (b);

$R_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_{17}$ and $R_{18}$ are independently selected from hydrogen, a non-interfering substituent, or the group, —($L_a$)-(acidic group); wherein —($L_a$)—, is an acid linker having an acid linker length of 1 to 10; provided, that at least one of $R_{17}$ and $R_{18}$ must be the group, —($L_a$)-(acidic group); and $R_{15}$ and $R_{16}$ are each independently selected from hydrogen, non-interfering substituent, carbocyclic radical, carbocyclic radical substituted with non-interfering substituents, heterocyclic radical, and heterocyclic radical substituted with non-interfering substituents.

Particularly preferred 1H-indole-1-functional compounds useful as sPLA$_2$ inhibitors in the practice of the method of the invention are as follows:

An indolizine-1-acetic acid hydrazide compound or a pharmaceutically acceptable salt, solvate or prodrug derivative thereof where said compound is represented by the formula (IId);

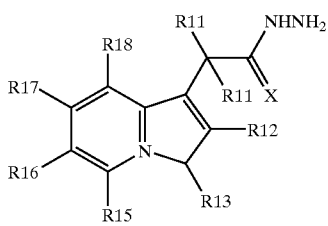

(IId)

Particularly preferred 1H-indole-1-functional compounds useful as sPLA$_2$ inhibitors in the practice of the method of the invention are as follows:

An indolizine-1-glyoxylamide compound or a pharmaceutically acceptable salt, solvate or prodrug derivative thereof; wherein said compound is represented by the formula (IIId);

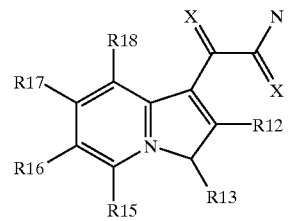

(IIId)

Another preferred 1H-indole-1-functional compounds useful as sPLA$_2$ inhibitors in the practice of the method of the invention are as follows:

An indolizine-3-acetamide compound or a pharmaceutically acceptable salt, solvate or prodrug derivative thereof; wherein said compound is represented by the formula (IVd), as set out below:

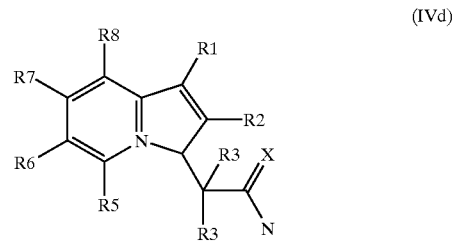

(IVd)

wherein;

X is selected from oxygen or sulfur;

each $R_3$ is independently hydrogen, $C_1$–$C_3$ alkyl, or halo;

$R_1$ is selected from groups (a), (b) and (c) where;
- (a) is $C_7$–$C_{20}$ alkyl, $C_7$–$C_{20}$ alkenyl, $C_7$–$C_{20}$ alkynyl, carbocyclic radical, or heterocyclic radical, or
- (b) is a member of (a) substituted with one or more independently selected non-interfering substituents; or
- (c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_5$ and $R_6$ are independently selected from hydrogen, a non-interfering substituent, or the group, —($L_a$)-(acidic group); wherein —($L_a$)—, is an acid linker having an acid linker length of 1 to 10; provided, that at least one of $R_5$ and $R_6$ must be the group, —($L_a$)-(acidic group);

$R_7$ and $R_8$ are each independently selected from hydrogen, non-interfering substituent, carbocyclic radical, carbocyclic radical substituted with non-interfering substituents, heterocyclic radical, and heterocyclic radical substituted with non-interfering substituents.

Particularly preferred 1H-indole-1-functional compounds useful as sPLA$_2$ inhibitors in the practice of the method of the invention are as follows:

An indolizine-3-hydrazide compound or a pharmaceutically acceptable salt, solvate or prodrug derivative thereof; wherein said compound is represented by the formula (Vd), as set out below:

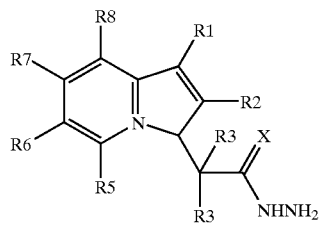

(Vd)

Particularly preferred 1H-indole-1-functional compounds useful as sPLA$_2$ inhibitors in the practice of the method of the invention are as follows:

An indolizine-3-glyoxylamide compound or a pharmaceutically acceptable salt, solvate or prodrug derivative thereof; wherein said compound is represented by the formula (VId), as set out below:

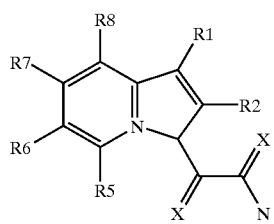

(VId)

Particularly preferred 1H-indole-1-functional compounds useful as sPLA$_2$ inhibitors in the practice of the method of the invention are as follows:

An indolizine-1-acetamide functional compound or a pharmaceutically acceptable salt, solvate or prodrug derivative thereof; wherein said compound is selected from the group represented by the following formulae:

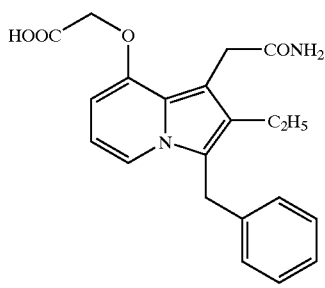

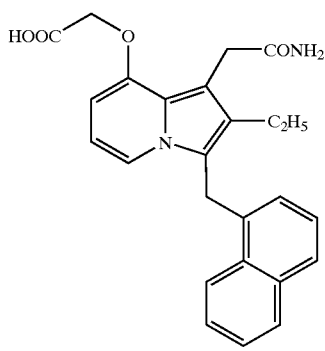

-continued

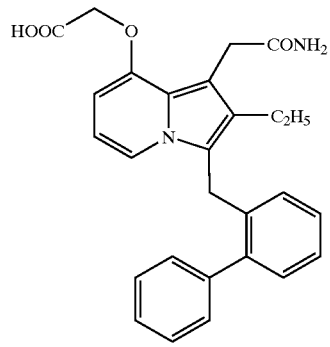

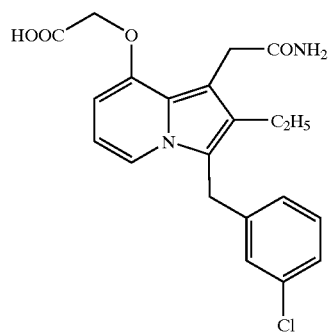

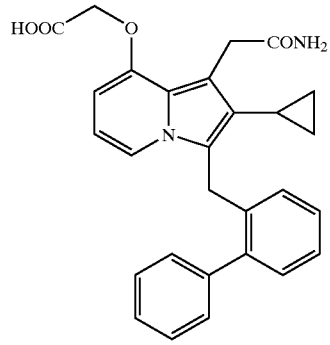

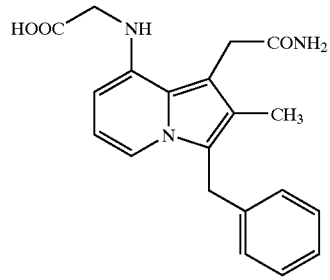

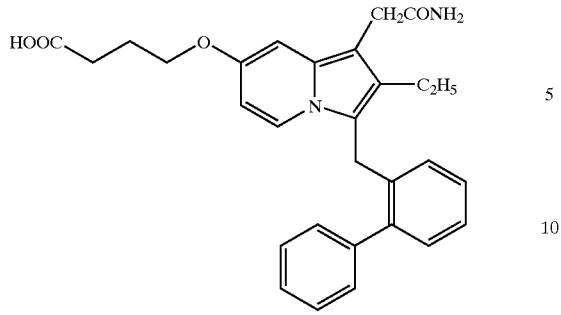

and mixtures of the above compounds.

Other particularly preferred 1H-indole-1-functional compounds useful as sPLA$_2$ inhibitors in the practice of the method of the invention are as follows:

An indolizine-1-glyoxylamide functional compound and a pharmaceutically acceptable salt, solvate or prodrug derivative thereof; wherein said compound is selected from the group represented by the following formulae:

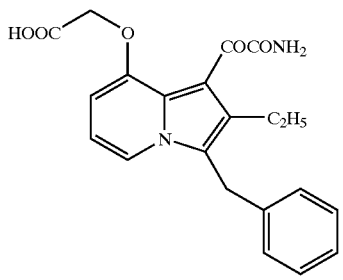

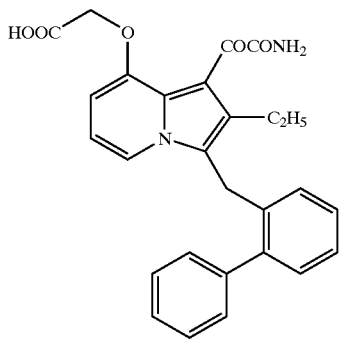

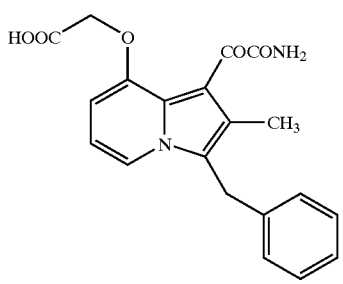

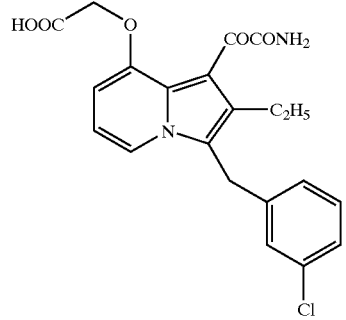

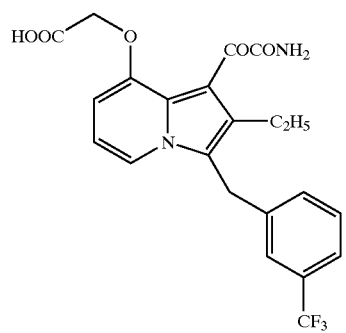

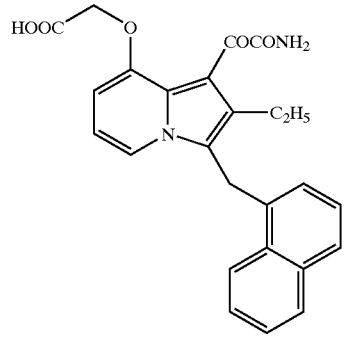

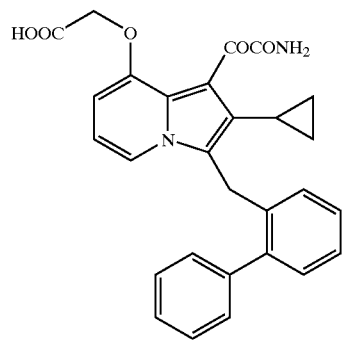

-continued
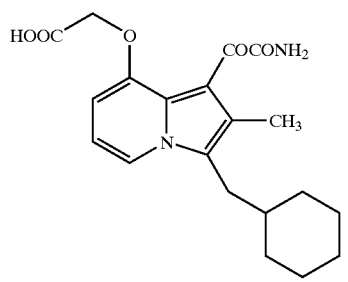
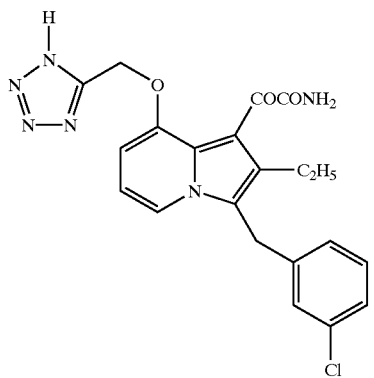
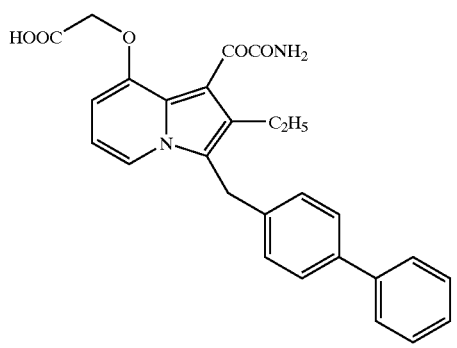
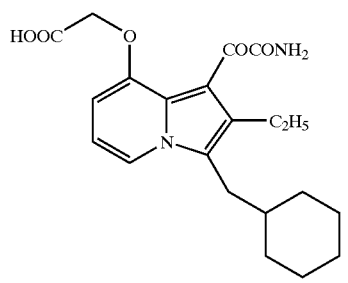
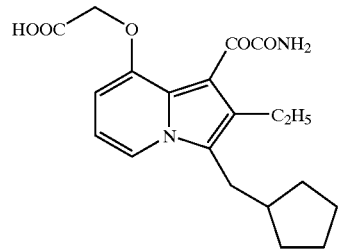
-continued
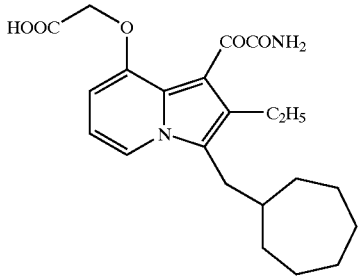
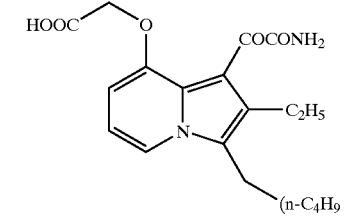
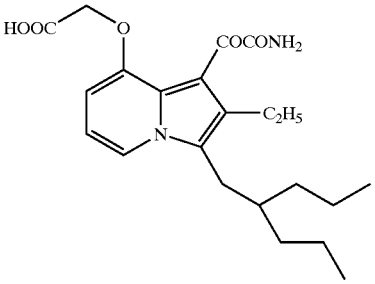
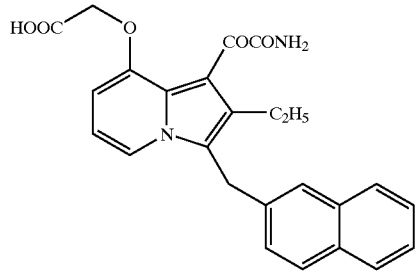
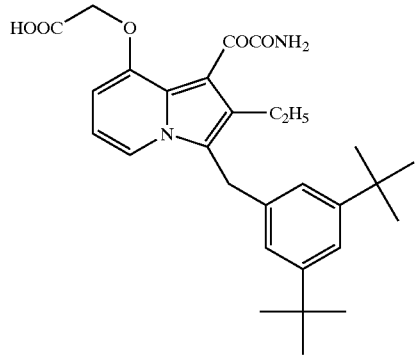
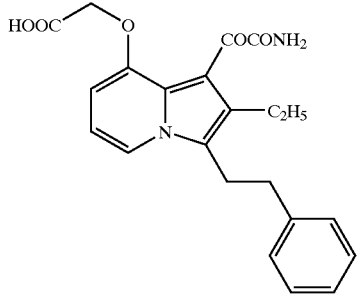

-continued
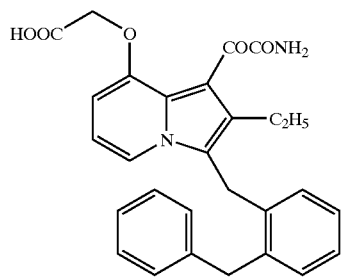
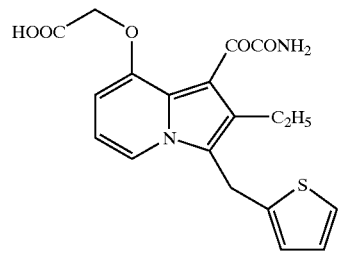
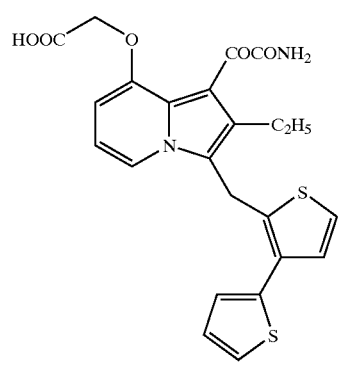
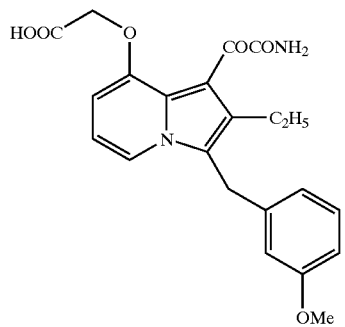
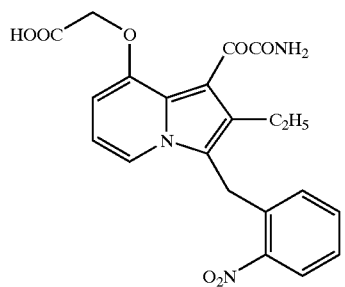
-continued
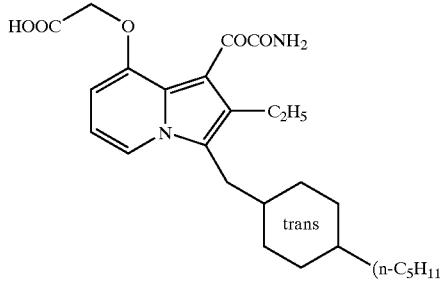
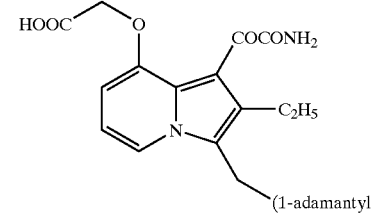
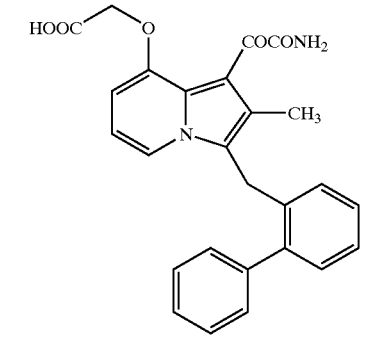
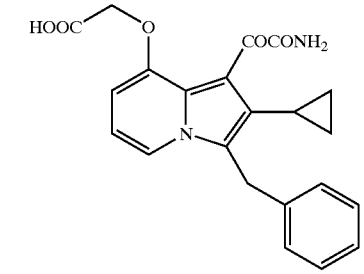
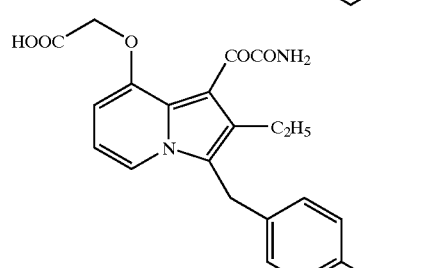
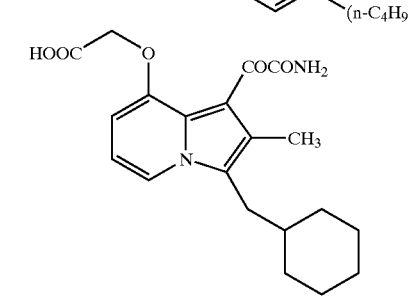

-continued
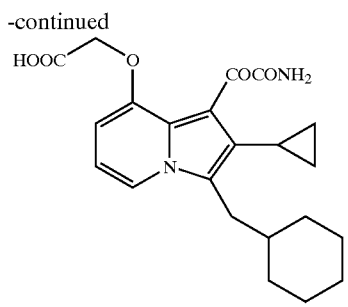
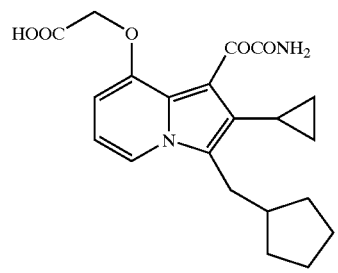
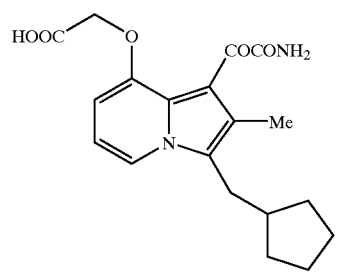
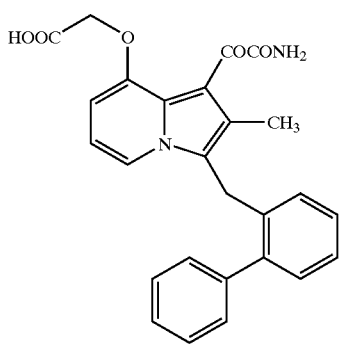
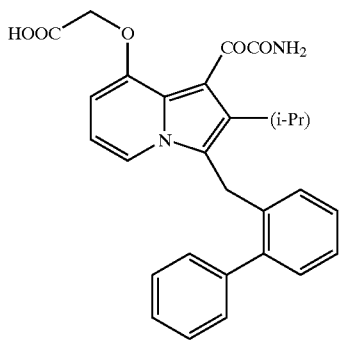
-continued
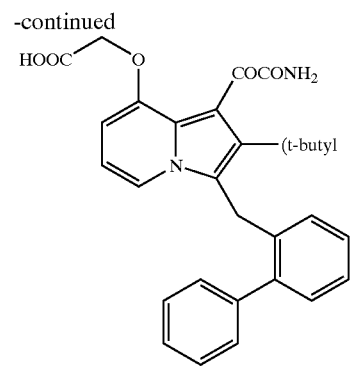
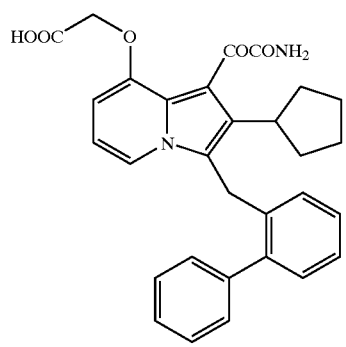
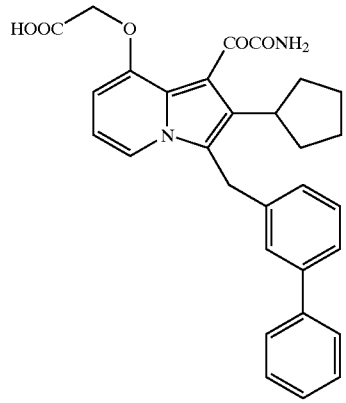
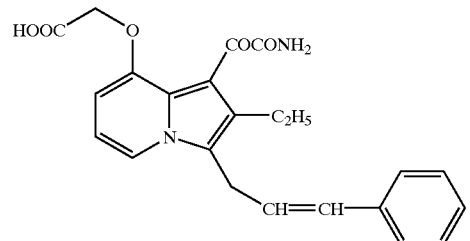
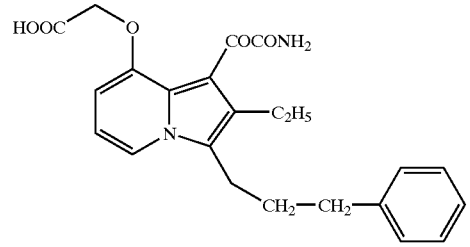

-continued
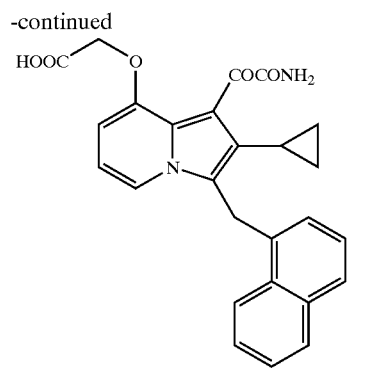
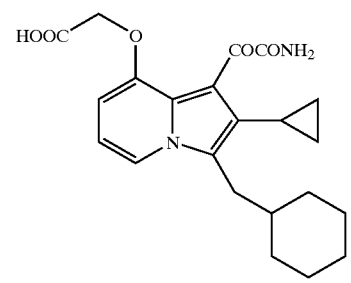
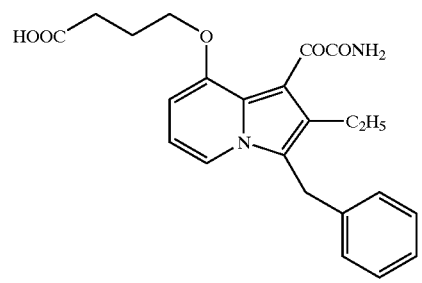
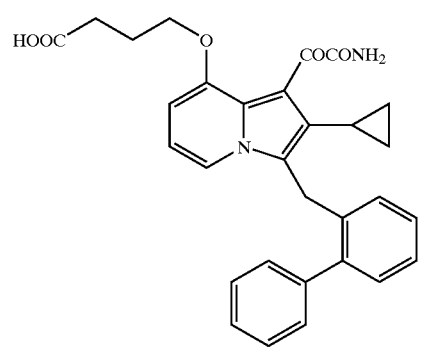
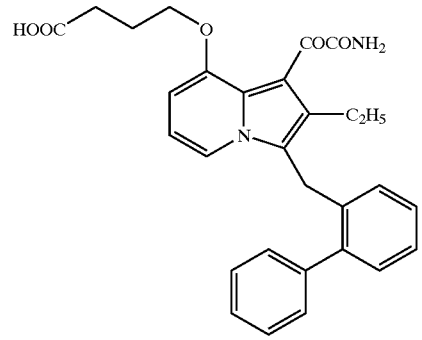
-continued
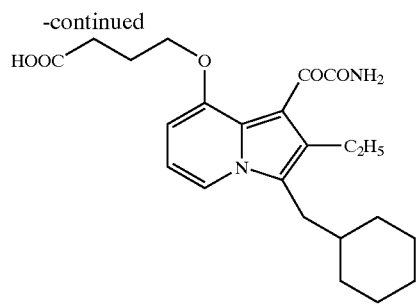
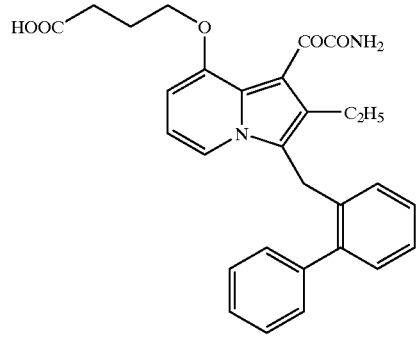
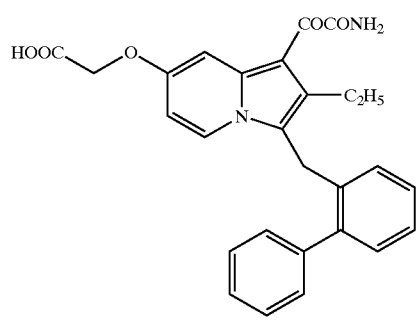
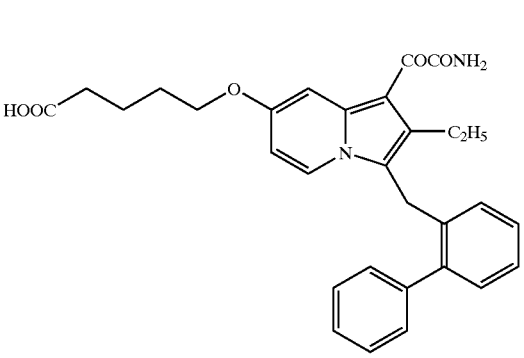
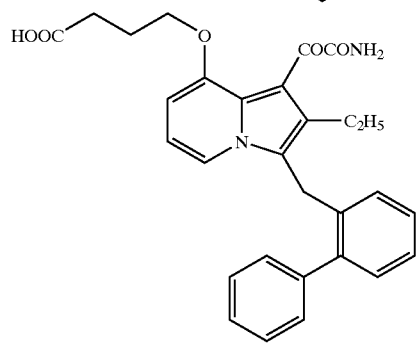

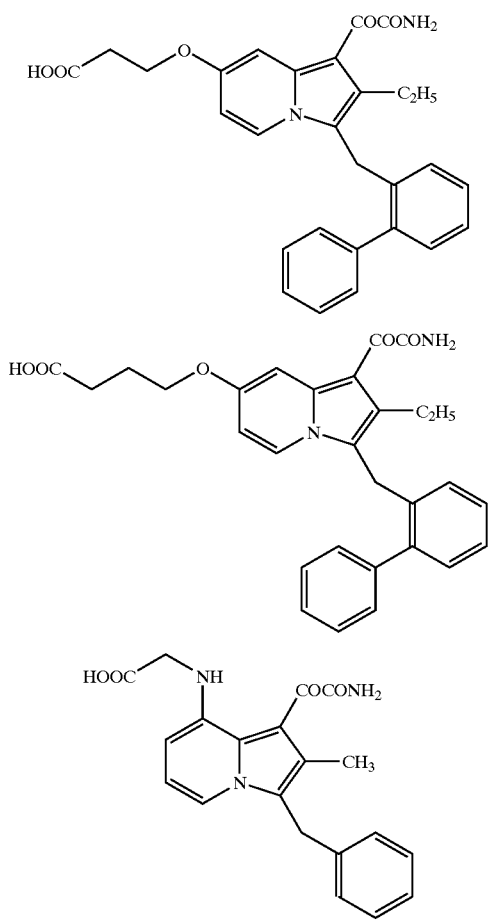
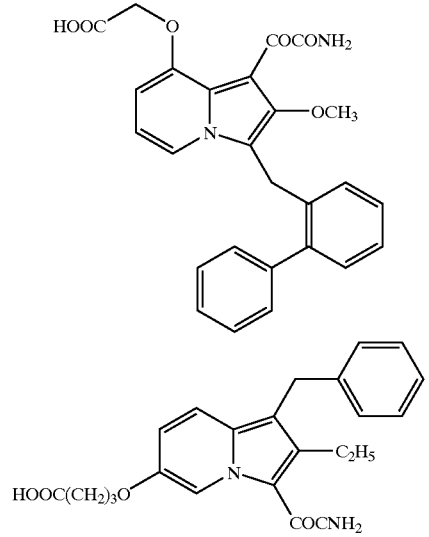
and mixtures of the above compounds.
The indolizine compounds may be made by one of more of the following reaction schemes:
The following abbreviations are used throughout the synthesis Schemes:
Bn benzyl
THF tetrahydrofuran
LAH lithium aluminum hydride
LDA lithium diiopropyl amine
DBU 1,8-diazabicyclo 5.4.0]undec-7-une
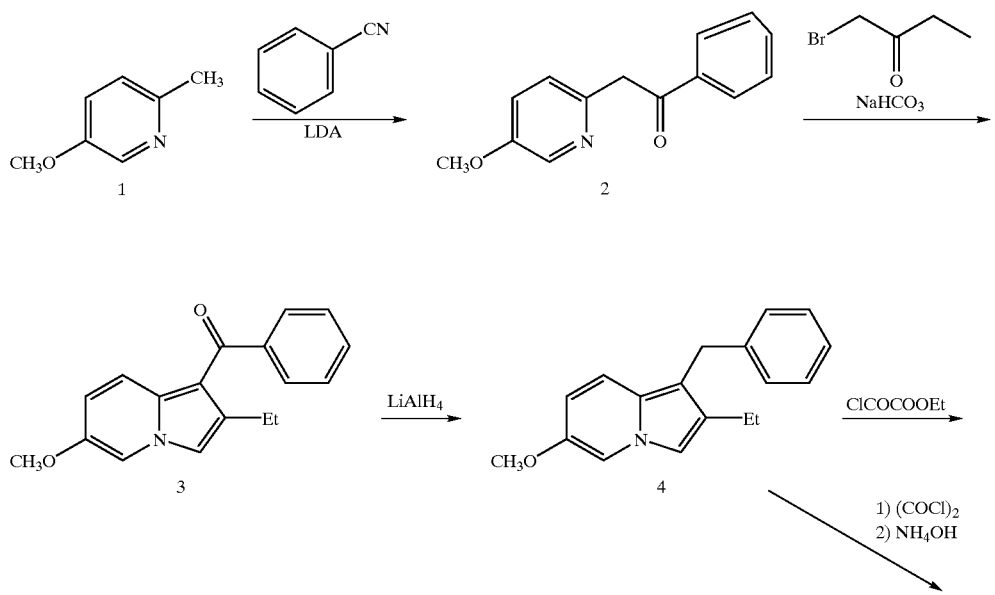

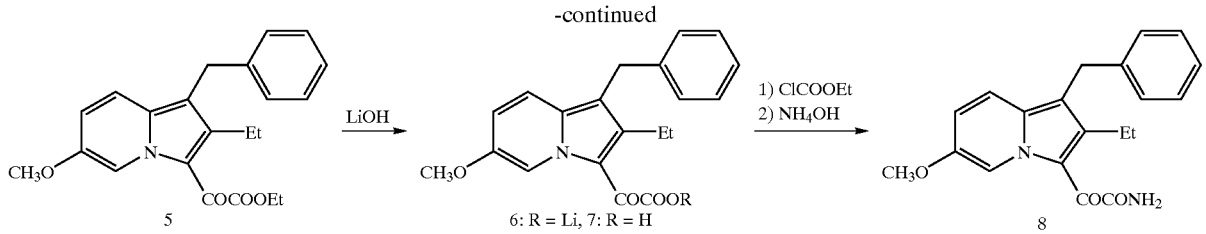

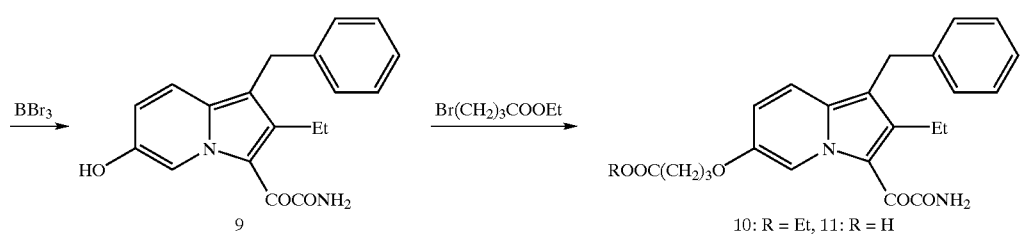

The anion of 2-methyl-5-methoxypyridine is formed in THF using lithium diisopropyl amide and reacted with benzonitrile to produce 2. Alkylation of the nitrogen of 2† by 1-bromo-2-butanone followed by base catalyzed cyclization forms 3 which is reduced by LAH to 4. Sequential treatment of 4 with oxalyl chloride and ammonia gives 8. Alternatively, 4 is acylated with ethyl oxalyl chloride to give 5 which is converted to 6 with lithium hydroxide and then to 8 by sequential treatment with ethyl chloroformate and ammonium hydroxide. Demethylation of 8 by $BBr_3$ yields 9 which is O-alkylated using base and ethyl 4-bromobutyrate to form 10. Hydrolysis of 10 by aqueous base produces 11.

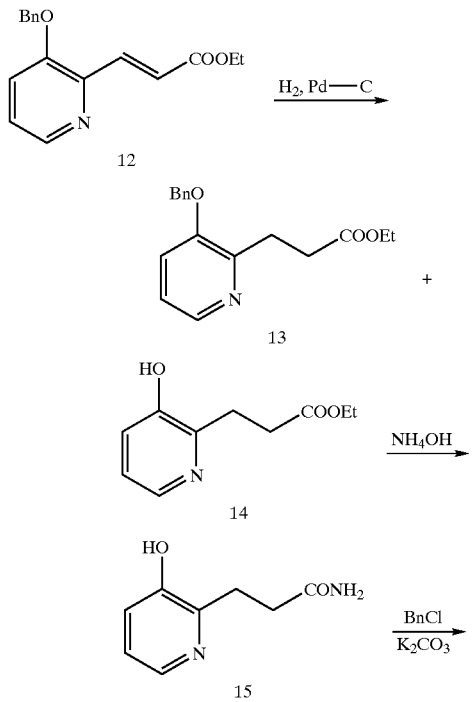

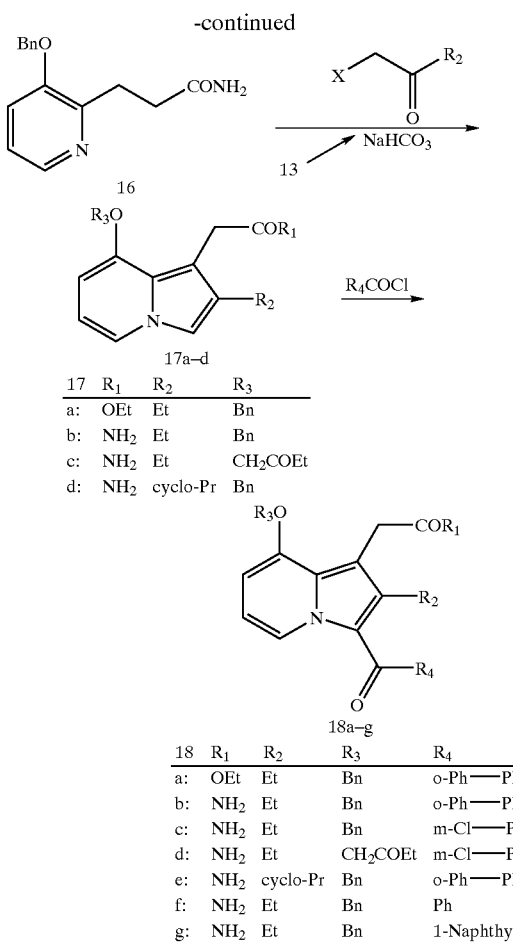

| 17 | $R_1$ | $R_2$ | $R_3$ |
|---|---|---|---|
| a: | OEt | Et | Bn |
| b: | $NH_2$ | Et | Bn |
| c: | $NH_2$ | Et | $CH_2COEt$ |
| d: | $NH_2$ | cyclo-Pr | Bn |

| 18 | $R_1$ | $R_2$ | $R_3$ | $R_4$ |
|---|---|---|---|---|
| a: | OEt | Et | Bn | o-Ph—Ph |
| b: | $NH_2$ | Et | Bn | o-Ph—Ph |
| c: | $NH_2$ | Et | Bn | m-Cl—Ph |
| d: | $NH_2$ | Et | $CH_2COEt$ | m-Cl—Ph |
| e: | $NH_2$ | cyclo-Pr | Bn | o-Ph—Ph |
| f: | $NH_2$ | Et | Bn | Ph |
| g: | $NH_2$ | Et | Bn | 1-Naphthyl |

Compound 12 (N. Desidiri, A. Galli, I. Sestili, and M. L. Stein, Arch. Pharm. (Weinheim) 325, 29, (1992)) is reduced by hydrogen in the presence of Pd/C to 14 which gives 15 on ammonolysis using ammonium hydroxide. O-alkylation of 15 using benzyl chloride and base affords 16. Alkylation of the nitrogen atom of 13 or 16 by 1-bromo-2-ketones followed by base catalyzed cyclization yields indolizines 17 which are acylated by aroyl halides to form 18.

Scheme 2e-Part 2

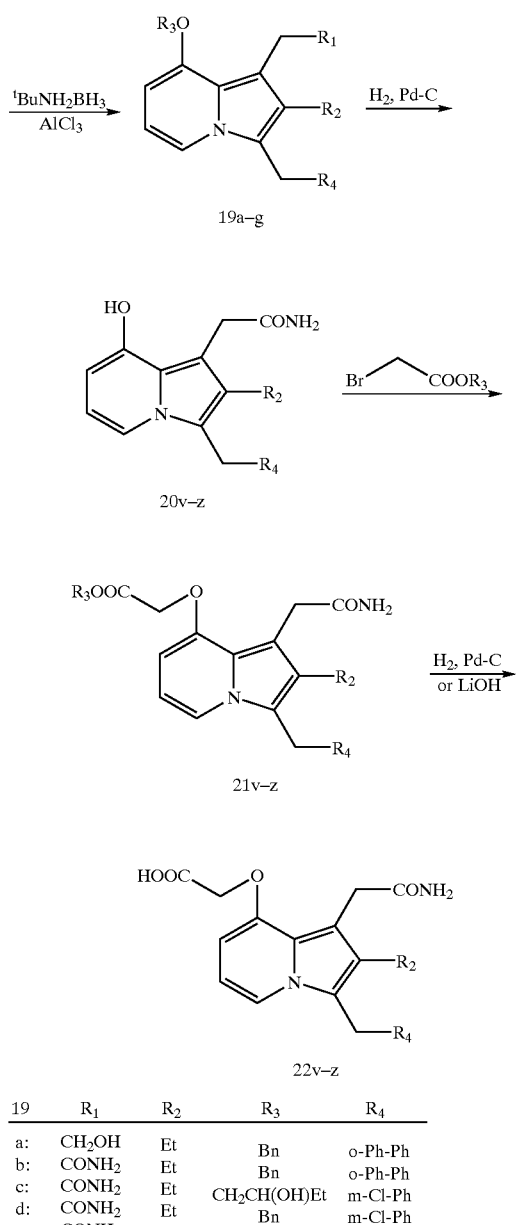

| 19 | R₁ | R₂ | R₃ | R₄ |
|---|---|---|---|---|
| a: | CH₂OH | Et | Bn | o-Ph-Ph |
| b: | CONH₂ | Et | Bn | o-Ph-Ph |
| c: | CONH₂ | Et | CH₂CH(OH)Et | m-Cl-Ph |
| d: | CONH₂ | Et | Bn | m-Cl-Ph |
| e: | CONH₂ | cyclo-Pr | Bn | o-Ph-Ph |
| f: | CONH₂ | Et | Bn | Ph |
| g: | CONH₂ | Et | Bn | 1-Naphthyl |

| 20–22 | R₂ | R₃ | R₄ |
|---|---|---|---|
| v: | Et | Et | Ph |
| w: | Et | Me | 1-Naphthyl |
| x: | Et | Bn | o-Ph-Ph |
| y: | Et | Bn | m-Cl-Ph |
| z: | cyclo-Pr | Me | o-Ph-Ph |

Reduction of 18 by tert-butylamine-borohydride and aluminum chloride yields 19 which is reduced by hydrogen in the presence of Pd/C to give 20. O-alkylation of 20 by benzyl bromoacetate and base forms 21 which is converted to the acid 22 by debenzylation using hydrogen in the presence of Pd/C.

Scheme 3e-Part 1

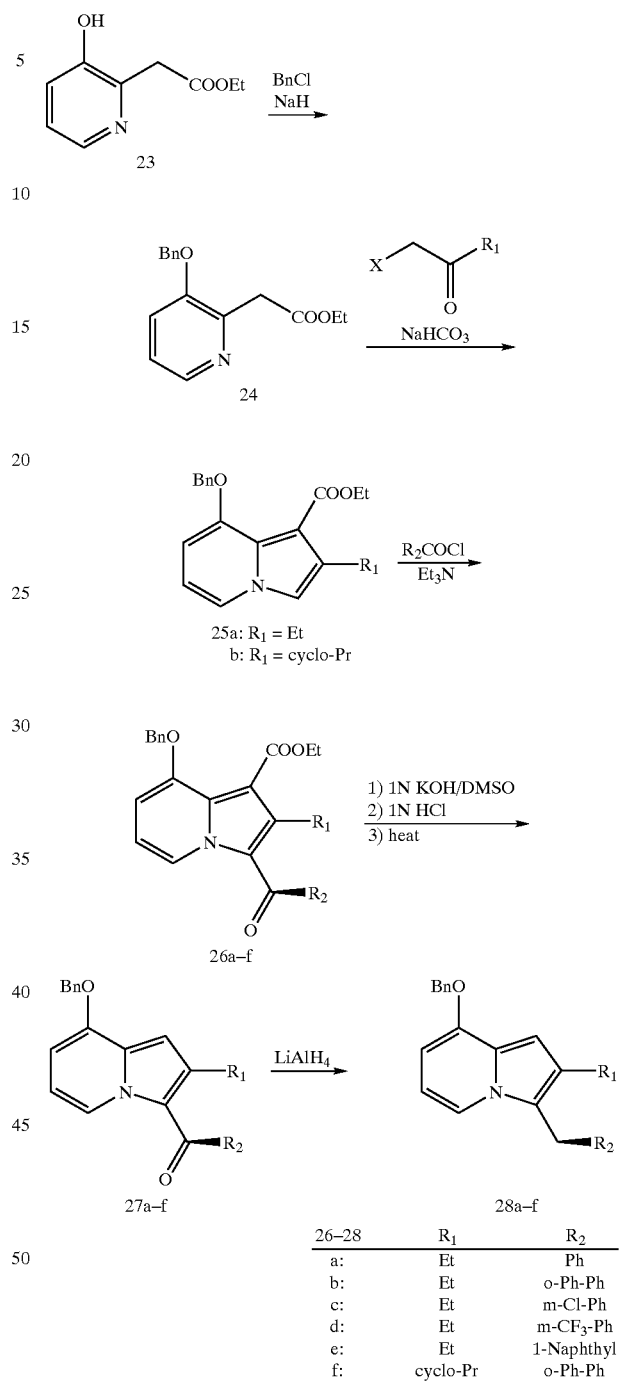

| 26–28 | R₁ | R₂ |
|---|---|---|
| a: | Et | Ph |
| b: | Et | o-Ph-Ph |
| c: | Et | m-Cl-Ph |
| d: | Et | m-CF₃-Ph |
| e: | Et | 1-Naphthyl |
| f: | cyclo-Pr | o-Ph-Ph |

Compound 23 (N. Desideri F. Manna, M. L. Stein, G. Bile, W. Filippeelli, and E. Marmo, Eur. J. Med. Chem. Chim. Ther., 18, 295, (1983)) is O-alkylated using sodium hydride and benzyl chloride to give 24. N-alkylation of 24 by 1-bromo-2-butanone or chloromethylcyclopropyl ketone and subsequent base catalyzed cyclization gives 25 which is acylated by aroyl halide to give 26. Hydrolysis of the ester function of 26 followed by acidification forms an acid which is thermally decarboxylated to give 27. Reduction of the ketone function of 27 by LAH yields indolizines 28.

Scheme 3e-Part 2

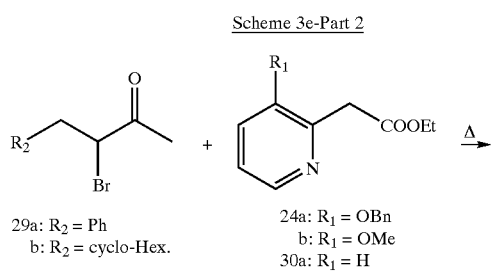

29a: $R_2$ = Ph
b: $R_2$ = cyclo-Hex.

24a: $R_1$ = OBn
b: $R_1$ = OMe
30a: $R_1$ = H

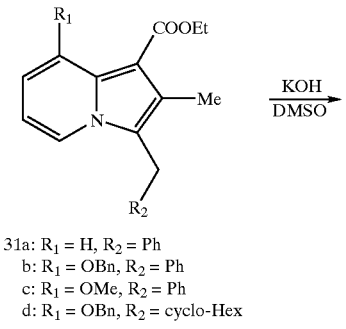

31a: $R_1$ = H, $R_2$ = Ph
b: $R_1$ = OBn, $R_2$ = Ph
c: $R_1$ = OMe, $R_2$ = Ph
d: $R_1$ = OBn, $R_2$ = cyclo-Hex

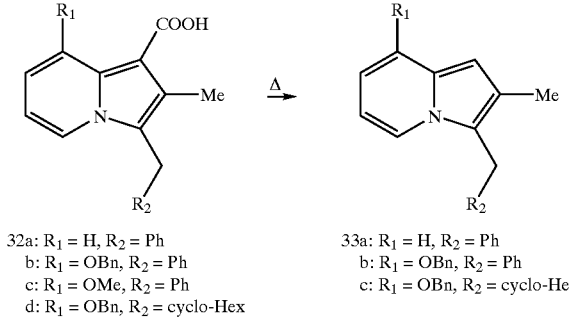

32a: $R_1$ = H, $R_2$ = Ph
b: $R_1$ = OBn, $R_2$ = Ph
c: $R_1$ = OMe, $R_2$ = Ph
d: $R_1$ = OBn, $R_2$ = cyclo-Hex 33a: $R_1$ = H, $R_2$ = Ph
b: $R_1$ = OBn, $R_2$ = Ph
c: $R_1$ = OBn, $R_2$ = cyclo-Hex Heating a mixture of 3-bromo-4-phenyl-butan-2-one or 3-bromo-4-cyclohexyl-butan-2-one and ethyl pyridine-2-acetate, or a substituted derivative, in the presence of base yields indolizine 31. Treatment of 31 with aqueous base in DMSO at elevated temperature followed by acidification gives 32 which is thermally decarboxylated to 33.

Scheme 4e-Part 1

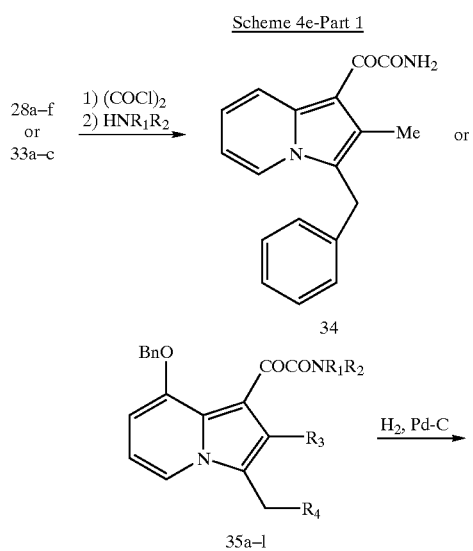

-continued

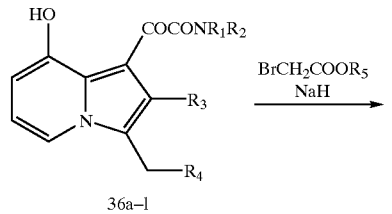

36a-l

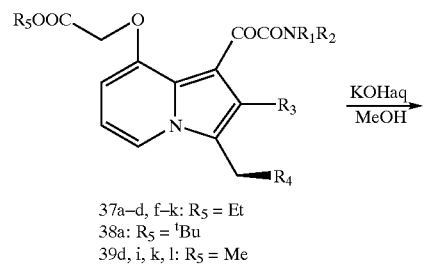

37a-d, f-k: $R_5$ = Et
38a: $R_5$ = $^t$Bu
39d, i, k, l: $R_5$ = Me

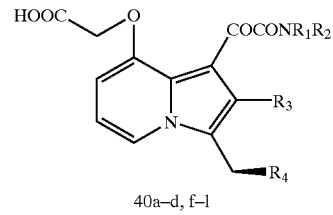

40a-d, f-l

| 35-40 | $R_1$ | $R_2$ | $R_3$ | $R_4$ |
|---|---|---|---|---|
| a: | H | H | Et | Ph |
| b: | H | Me | Et | Ph |
| c: | Me | Me | Et | Ph |
| d: | H | H | Et | o-Ph-Ph |
| e: | H | Me | Et | o-Ph-Ph |
| f: | Me | Me | Et | o-Ph-Ph |
| g: | H | H | Me | Ph |
| h: | H | H | Et | m-Cl-Ph |
| i: | H | H | Et | m-CF$_3$-Ph |
| j: | H | H | Et | 1-Naphthyl |
| k: | H | H | cyclo-Pr | o-Ph-Ph |
| l: | H | H | Me | cyclo-Hex |

Sequential treatment of 28 or 33 with oxalyl chloride and ammonium hydroxide forms 35 which is debenzylated by hydrogen in the presence of Pd/C to give 36. Indolizines 36 are O-alkylated using sodium hydride and bromoacetic acid esters to form 37, 38, or 39 which are converted to indolizines 40 by hydrolysis with aqueous base followed by acidification.

Scheme 4e-Part 2

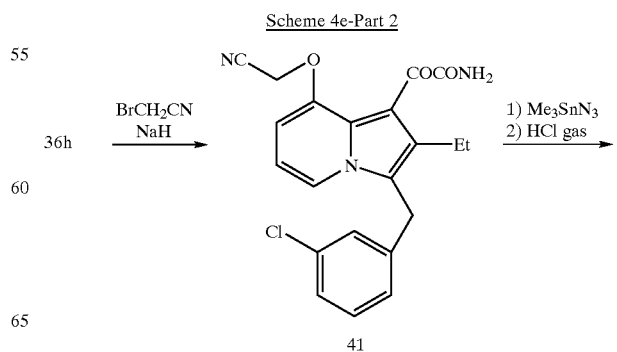

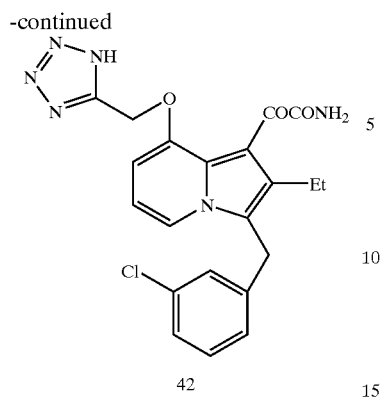
The O-alkylation of 36h produces nitrite 41 which is converted to 42 on reaction with trialkyltin azide.
Scheme 5e
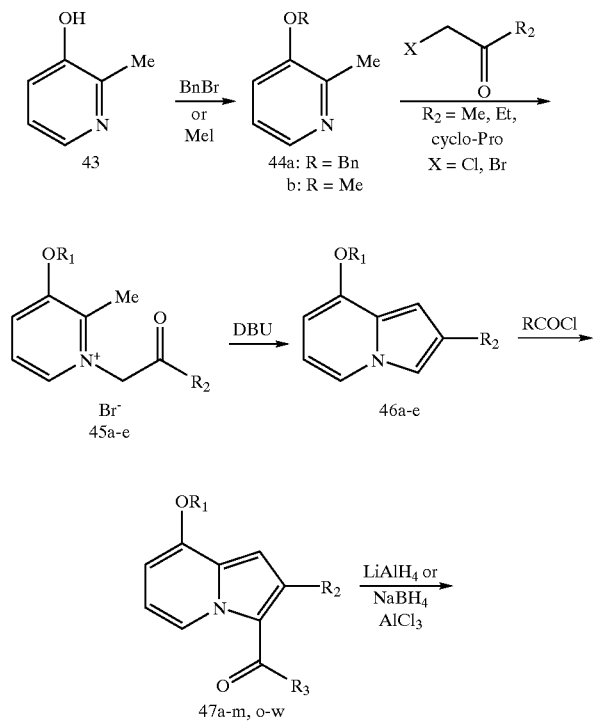
| 45, 46 | R₁ | R₂ | 47–52 | R₁ | R₂ | R₃ |
|---|---|---|---|---|---|---|
| a: | Bn | Et | a–o | Bn | Et | a–o (see below) |
| b: | Me | Et | p | Bn | Me | 1-adamantyl |
| c: | Bn | Me | q | Bn | Me | o-biphenyl |
| d: | Me | cyclo-Pro | r | Bn | cycloPro | phenyl |
| e: | Bn | cyclo-Pro | s | Me | Et | p-n-C₄H₉—Ph |
| | | | t | Bn | Me | cyclo-Hex |
| | | | u | Me | cycloPro | cyclo-Hex |
| | | | v | Bn | cycloPro | cyclopentyl |
| | | | w | Bn | Me | cyclolpentyl |

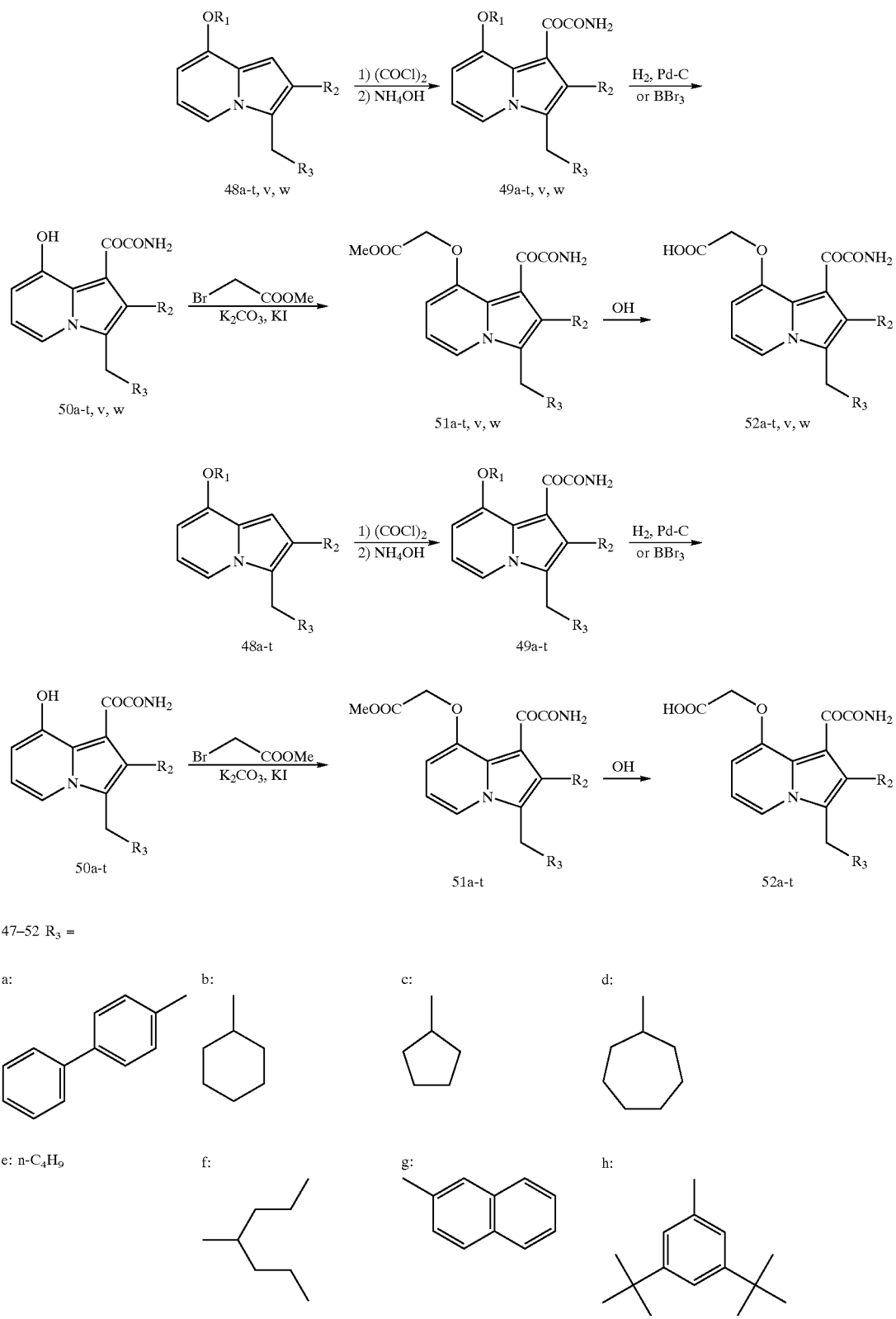

Scheme 5e

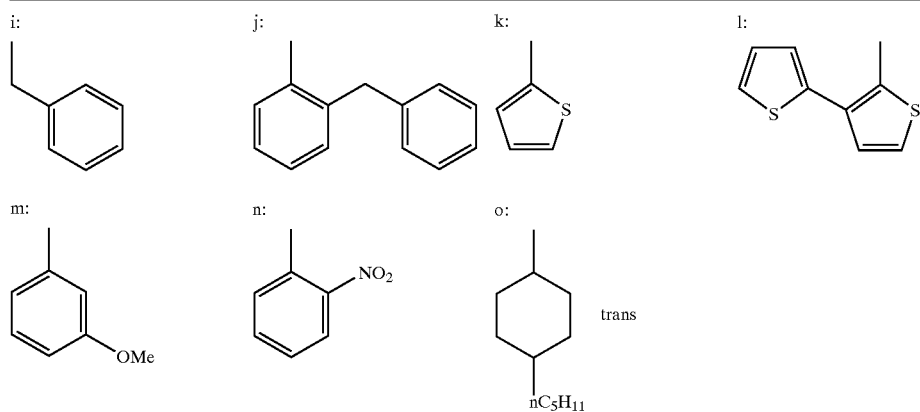

The hydroxypyridine is O-alkylated to give 44 which is heated with 2-haloketones to produce 45. Treatment of 45 with base causes cyclization to 46 which on heating with acid chlorides yields acylindolizines 47 which are reduced by aluminum hydride to the corresponding alkylindolizines 48. Sequential treatment of 48 with oxalyl chloride and then ammonia gives 49. Cleavage of the ether functionality of 49 yields 50. The oxyacetic ester derivatives 51 are formed by O-alkylation of 50 and then hydrolyzed to the oxyacetic acids 52.

Scheme 6e — Part 1

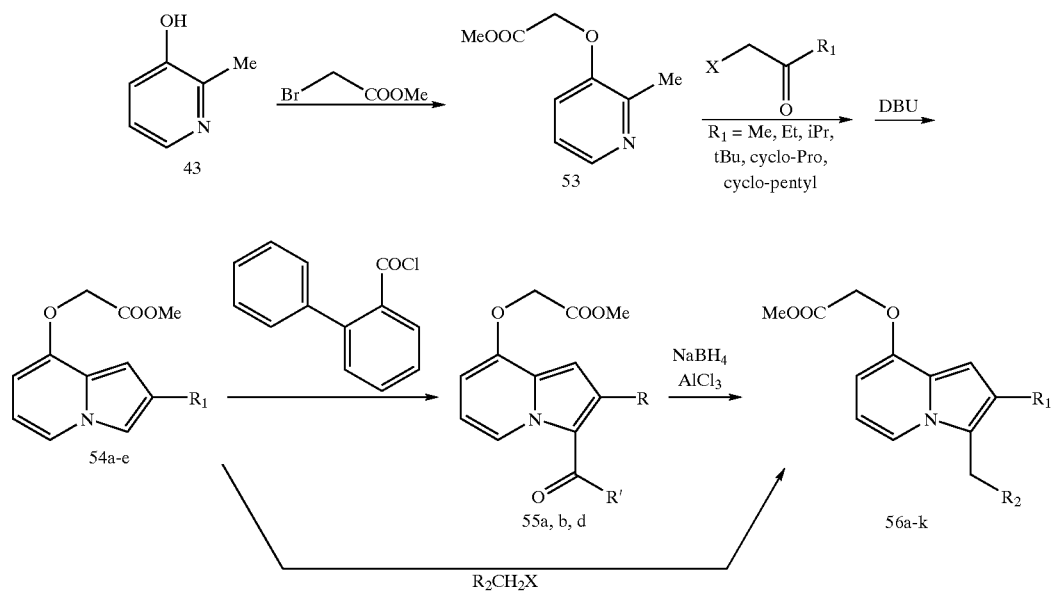

| 54, 55 | $R_1$ | $R_2$ |
|---|---|---|
| a: | Me | o-biphenyl |
| b: | Et | o-biphenyl |
| c: | iPro | o-biphenyl |
| d: | cyclo-Pro | cyclohexyl |
| e: | tBu | o-biphenyl |
| f: | cyclopenty | o-biphenyll |

Scheme 6e — Part 1

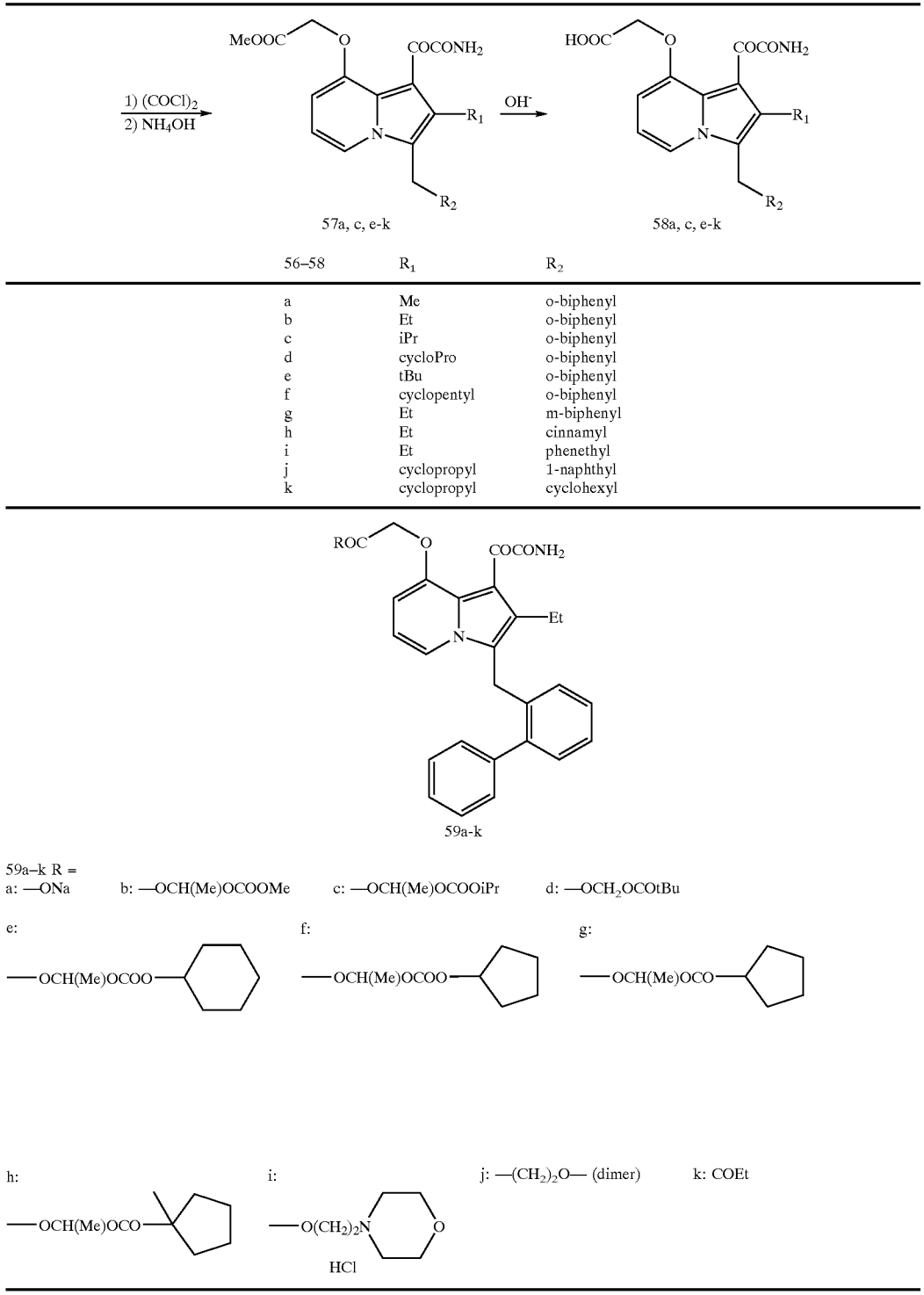

| 56–58 | $R_1$ | $R_2$ |
|---|---|---|
| a | Me | o-biphenyl |
| b | Et | o-biphenyl |
| c | iPr | o-biphenyl |
| d | cycloPro | o-biphenyl |
| e | tBu | o-biphenyl |
| f | cyclopentyl | o-biphenyl |
| g | Et | m-biphenyl |
| h | Et | cinnamyl |
| i | Et | phenethyl |
| j | cyclopropyl | 1-naphthyl |
| k | cyclopropyl | cyclohexyl |

59a–k R =
a: —ONa   b: —OCH(Me)OCOOMe   c: —OCH(Me)OCOOiPr   d: —OCH$_2$OCOtBu e: —OCH(Me)OCOO-cyclohexyl   f: —OCH(Me)OCOO-cyclopentyl   g: —OCH(Me)OCO-cyclopentyl h: —OCH(Me)OCO-(1-methylcyclopentyl)   i: —O(CH$_2$)$_2$N-morpholine·HCl   j: —(CH$_2$)$_2$O— (dimer)   k: COEt Pyridine 43 is O-alkylated to produce 53. Heating 53 with 2-haloketones gives intermediate N-alkylated pyridinium compounds which are cyclized to 54 on treatment with base. Heating 54 with acyl chlorides gives the acylindolizines 55 which are reduced to the alkylindolizines 56 by sodium borohydride-aluminum chloride. Alternatively, 56 are produced by C-alkylation of 54 using alkyl halides. Sequential treatment of 56 with oxalyl chloride and then ammonia gives 57 which are hydrolyzed to produce 58. Compound 58b is converted to its sodium salt 59a which yields 59b–k on reaction with the appropriate alkyl halide.

Scheme 6e - Part 2

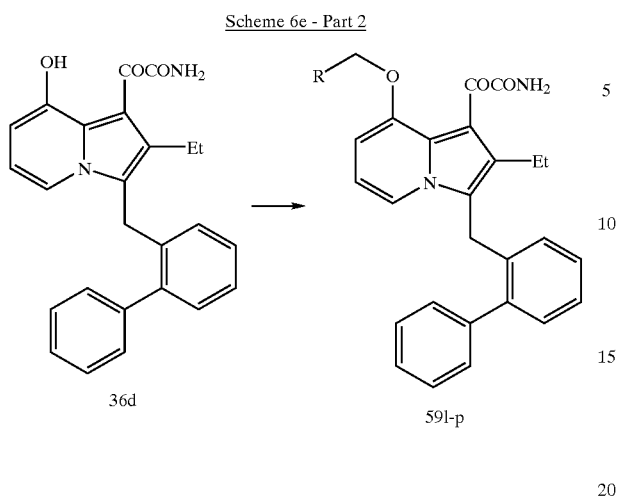

36d → 59l-p 59l-p R = l: tetrazole-NTr; m: tetrazole-H; n: 2-pyridyl; o: 4-pyridyl; p: 2-quinolyl

Compound 36b is O-alkylated to give 59l-p.

Scheme 7e

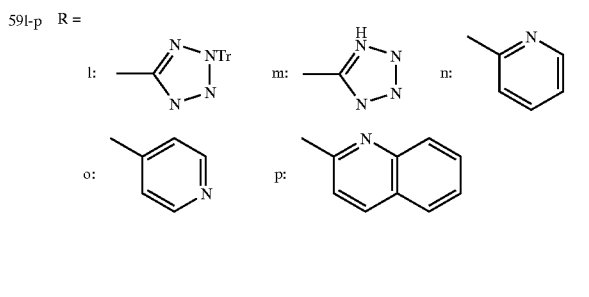

60 + haloketone (R₁ = Et, cyclo-Pro; X = Cl, Br) → DBU →

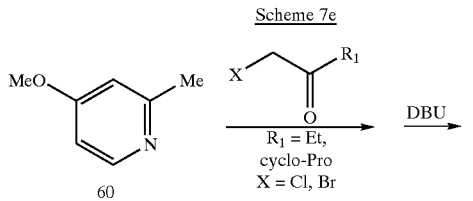

61a: R₁ = Et
b: R₁ = cycloPro

R₂COCl →

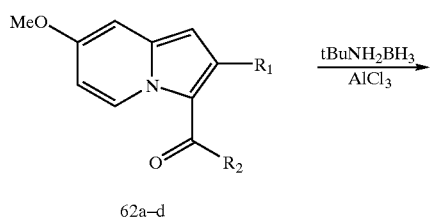

62a-d tBuNH₂BH₃ / AlCl₃ →

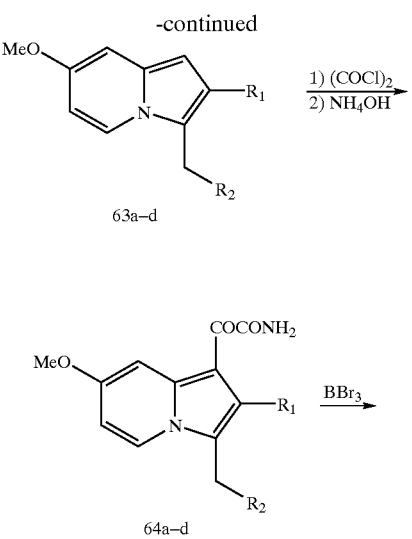

63a-d 1) (COCl)₂
2) NH₄OH →

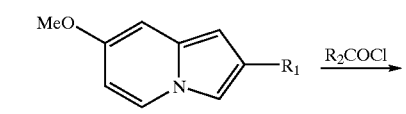

64a-d

BBr₃ →

65a-d

Br(CH₂)₃COOEt / NaH →

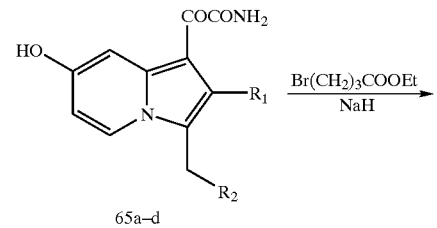

66a-d → LiOH → 67a-d

| 62–67 | R1 | R2 |
|---|---|---|
| a: | Et | Ph |
| b: | cyclo Pro | o-Ph-Ph |
| c: | Et | o-Ph-Ph |
| d: | Et | cyclohexyl |

Pyridine 60 is N-alkylated by 2-haloketones to produce intermediate pyridinium compounds which are cyclized by base to give 61. Reaction of 61 with acyl chlorides produces 62 which are reduced to 63 by tert butylamine-borane and aluminum chloride. Sequential treatment of 63 with oxalyl chloride and then ammonia yields 64 which are O-demethylated by BBr₃ to give 65. The sodium salt of 65 is reacted with ethyl 4-bromobutyrate to give 66 which is hydrolyzed to the acid 67.

Scheme 8e
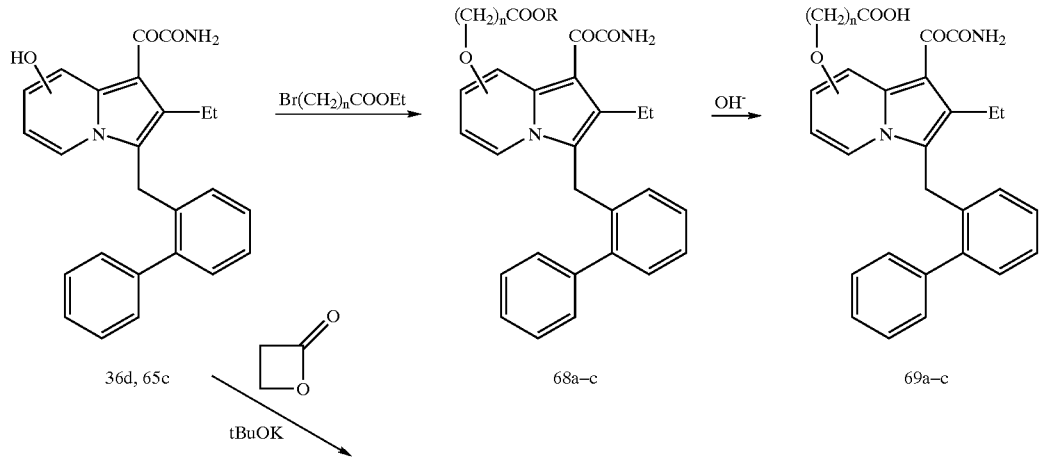
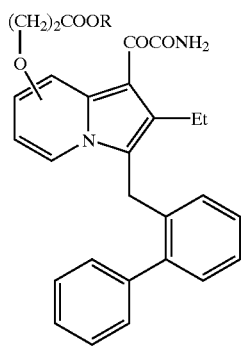
| 68–69 | n | position |
|---|---|---|
| a: | 3 | 8- |
| b: | 1 | 7- |
| c: | 4 | 7- |
70a: 8-, R = H
b: 7-, R = H
c: 8-, R = Me
Compounds 36d and 65c are O-alkylated by omega-bromocarboxylic esters to give 68 which are hydrolyzed to the acids 69. Compounds 36d and 65c produce 70 on treatment with propiolactone and base.
Scheme 9e
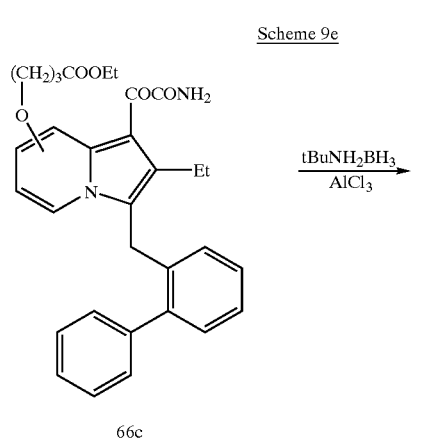
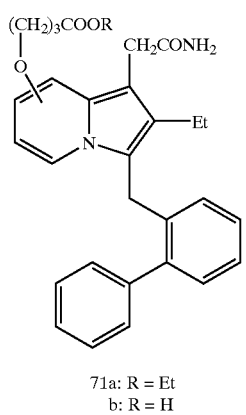
71a: R = Et
b: R = H
Compounds 66 are reduced to 71 by tert-butylamine-borane and aluminum chloride.

Scheme 10e
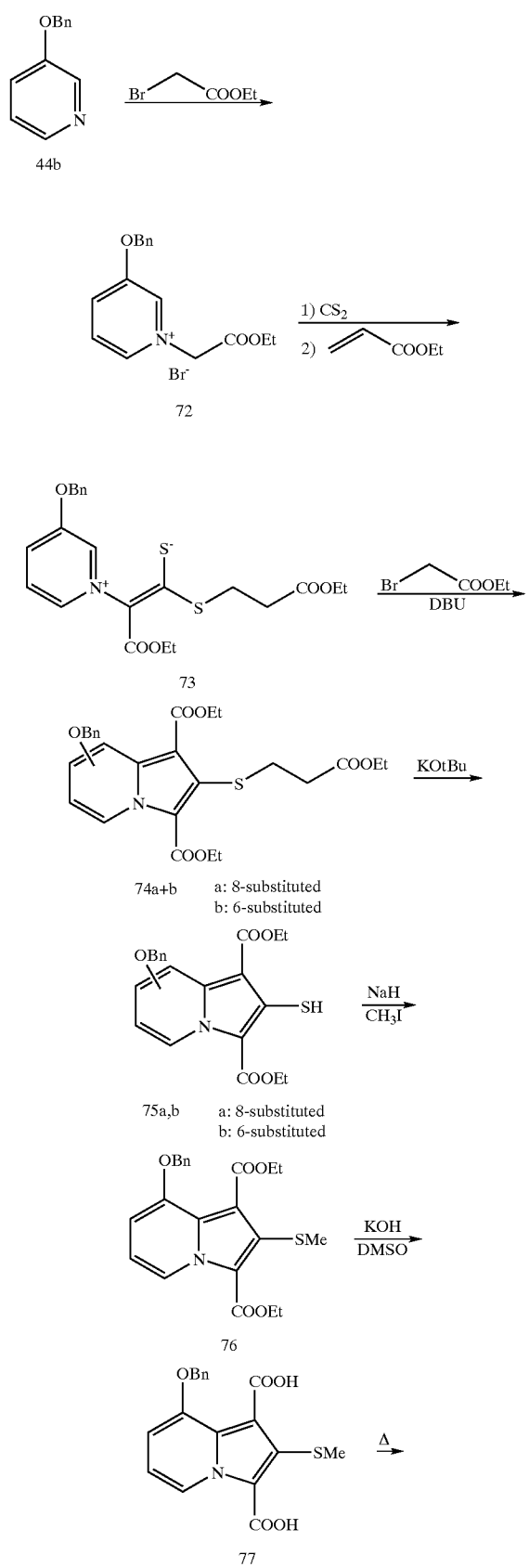
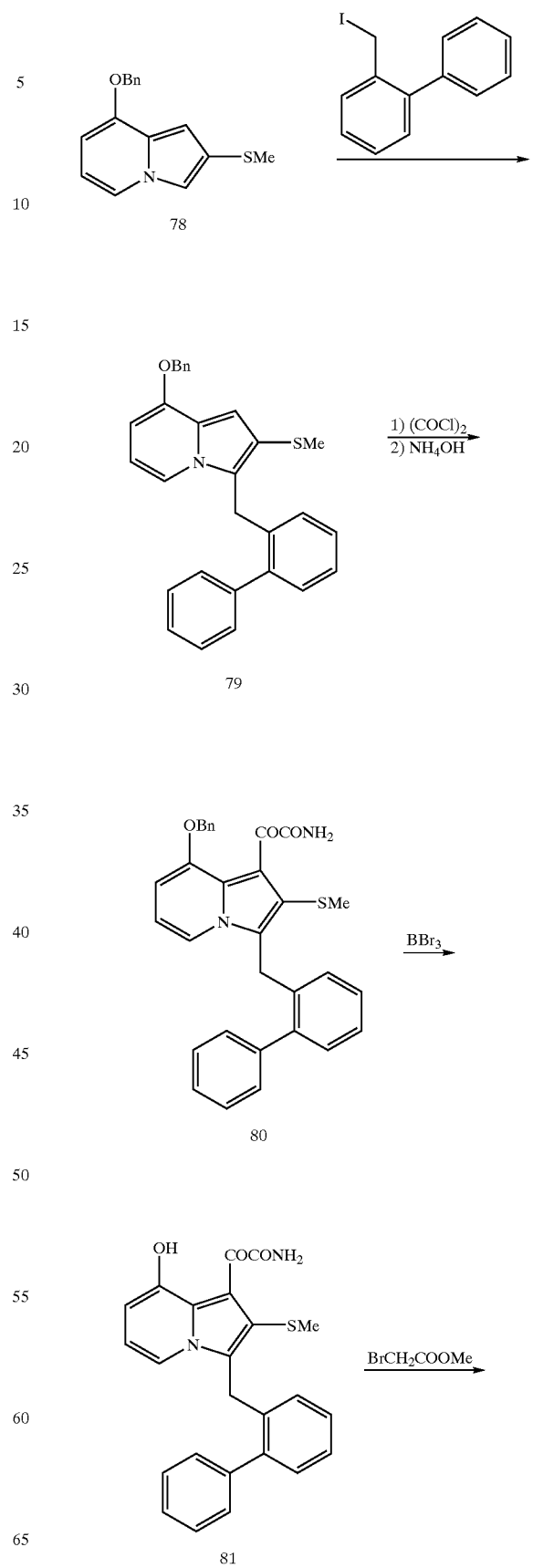

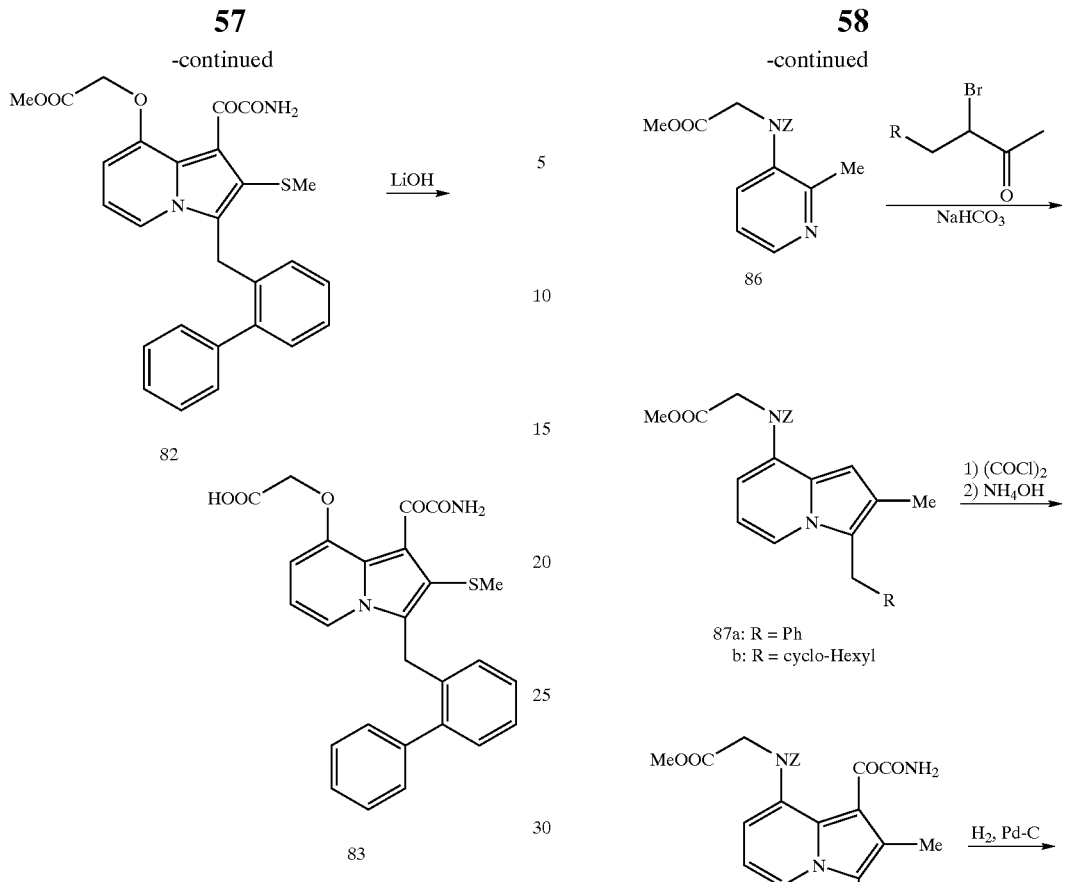

Pyridine 44b reacts with ethyl bromoacetate to produce 72 which is treated with CS$_2$ and base and then with ethyl acrylate to form 73. Reaction of 73 with base and ethyl bromoacetate yields a mixture of regioisomers 74a+b, 6- and 8-benzyloxy compounds. Base treatment of 74a+b eliminates ethyl acrylate to form 75 which is separated from the isomer of 6-benzyloxy derivative and S-alkylated to give 76. Hydrolysis of 76 forms 77 which is thermally decarboxylated to yield 78. Compound 78 is C-alkylated to form 79 which on sequential treatment with oxalyl chloride and then ammonia forms 80. Ether cleavage of 80 gives 81 whose sodium salt is alkylated by methyl bromoacetate to form 82 which are hydrolyzed to acids 83.

Scheme 11e-Part 1

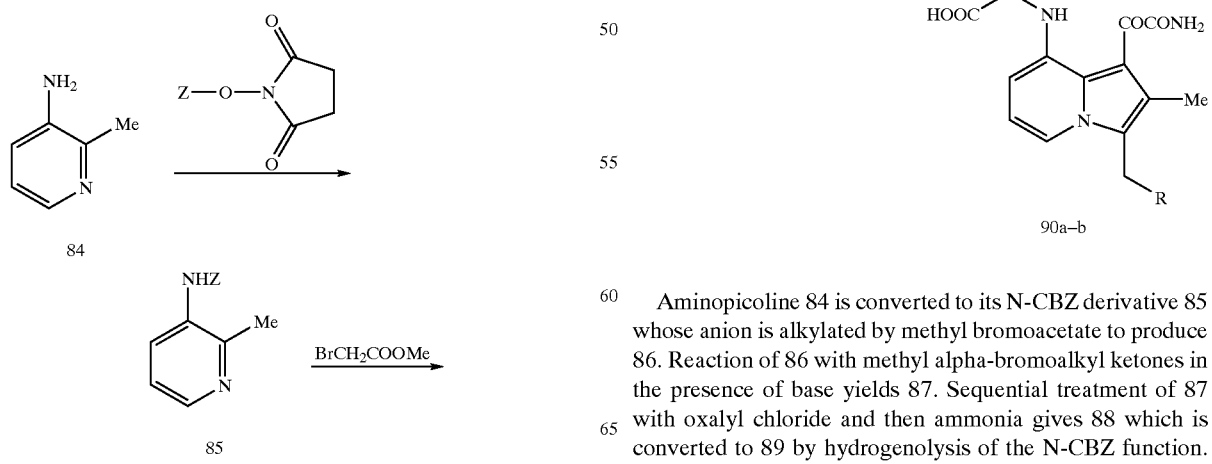

Aminopicoline 84 is converted to its N-CBZ derivative 85 whose anion is alkylated by methyl bromoacetate to produce 86. Reaction of 86 with methyl alpha-bromoalkyl ketones in the presence of base yields 87. Sequential treatment of 87 with oxalyl chloride and then ammonia gives 88 which is converted to 89 by hydrogenolysis of the N-CBZ function. Hydrolysis of 89 yields acids 90.

Scheme 11e-Part 2
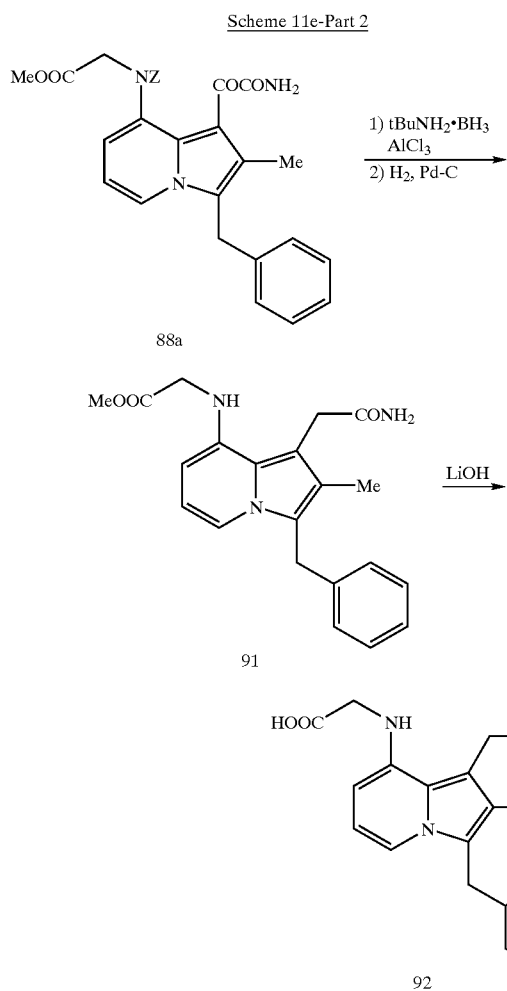
Compounds 88 are reduced by tert-butylamine-borane and aluminum chloride to 91 which are hydrolyzed to acids 92.
Scheme 12e
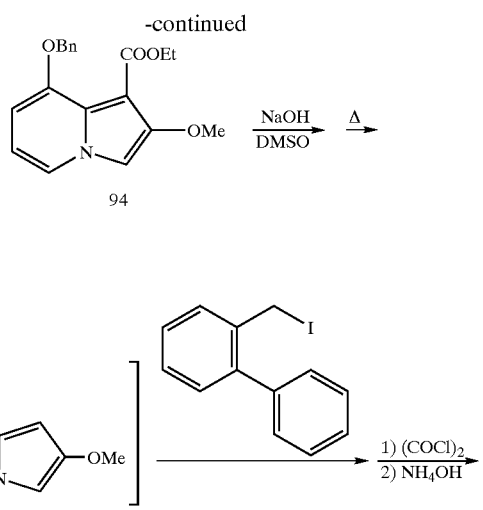
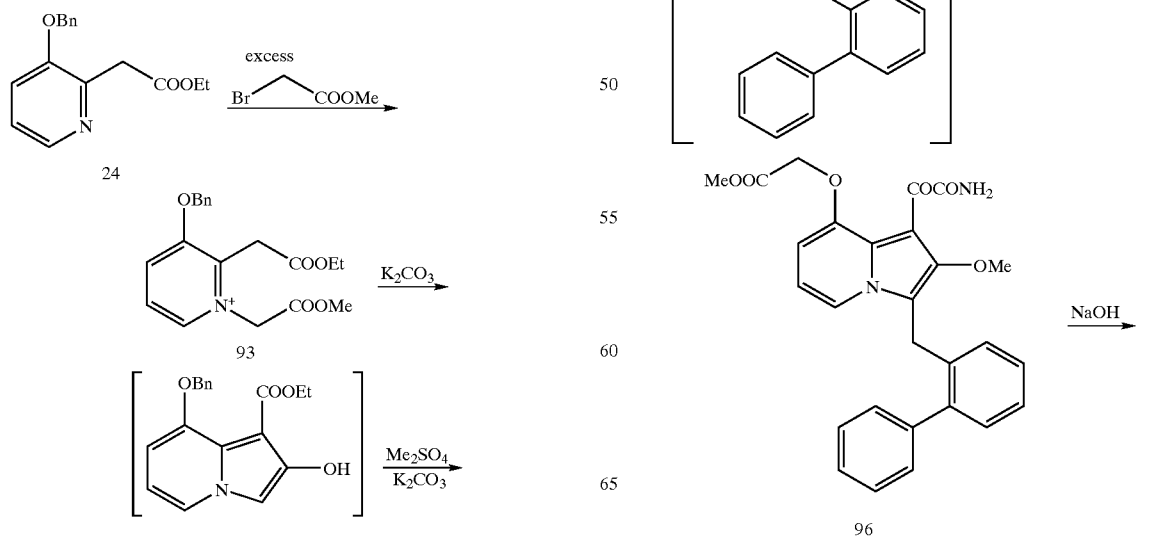

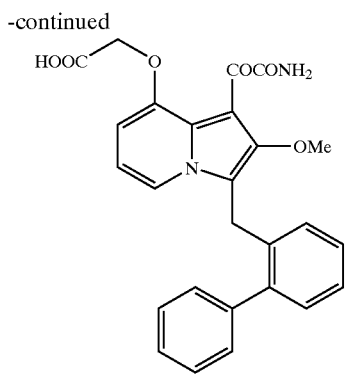

97

Pyridine 24 is N-alkylated by methyl bromoacetate, cyclized with base, and o-methylated using dimethysulfate to give 94. Hydrolysis of the ester function of 94 followed by thermal decarboxylation yields 2-methoxy-8-benzyloxyindolizine which is C-alkylated at position 3 and then reacted sequentially with oxalyl chloride and ammonia to produce 95. Hydrogenolysis of the 8-benzyloxy group followed by O-alkylation gives 96 which is hydrolyzed to 97.

f) Indene sPLA$_2$ inhibitors as described in U.S. patent application Ser. No. 08/776,618 filed Jul. 20 1995, (titled, Synovial Phospholipase A2 Inhibitor Compounds having an Indene Type Nucleus, Pharmaceutical Formulations Containing said Compounds, and Therapeutic Methods of Using Said Compounds"), the entire disclosure of which is incorporated herein by reference, are useful in practicing the method of the invention.

The method of the invention is for treatment of a mammal, including a human, afflicted with cystic fibrosis, said method comprising administering to said human a therapeutically effective amount of an indene-1-acetamide compound or a pharmaceutically acceptable salt, solvate or prodrug derivative thereof; wherein said compound is represented by the formula (If);

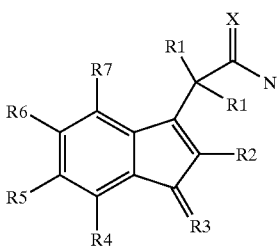

(If)

wherein;

X is oxygen or sulfur;

each $R_1$ is independently hydrogen, $C_1$–$C_3$ alkyl, or halo;

$R_3$ is selected from groups (a), (b) and (c) where;
   (a) is $C_7$–$C_{20}$ alkyl, $C_7$–$C_{20}$ alkenyl, $C_7$–$C_{20}$ alkynyl, carbocyclic radical, or heterocyclic radical, or
   (b) is a member of (a) substituted with one or more independently selected non-interfering substituents; or
   (c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_1$–$C_3$ cycloalkyl, $C_3$–$C_4$ cycloalkenyl, —O—($C_1$–$C_2$ alkyl), —S— ($C_1$–$C_2$ alkyl), or a non-interfering substituent having a total of 1 to 3 atoms other than hydrogen;

$R_6$ and $R_7$ are independently selected from hydrogen, a non-interfering substituent, or the group, —($L_a$)-(acidic group); wherein —($L_a$)—, is an acid linker having an acid linker length of 1 to 10; provided, that at least one of $R_6$ and $R_7$ must be the group, —($L_a$)-(acidic group); and $R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

Suitable indene compounds also include the following: An indene-1-acetic acid hydrazide compound or a pharmaceutically acceptable salt, solvate or prodrug derivative thereof; wherein said compound is represented by the formula (IIf);

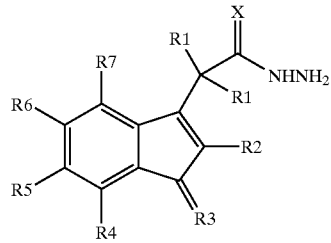

(IIf)

wherein:

X is oxygen or sulfur;

each $R_1$ is independently hydrogen, $C_1$–$C_3$ alkyl, or halo;

$R_3$ is selected from groups (a), (b) and (c) where;
   (a) is $C_7$–$C_{20}$ alkyl, $C_7$–$C_{20}$ alkenyl, $C_7$–$C_{20}$ alkynyl, carbocyclic radical, or heterocyclic radical, or
   (b) is a member of (a) substituted with one or more independently selected non-interfering substituents; or
   (c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_6$ and $R_7$ are independently selected from hydrogen, a non-interfering substituent, or the group, —($L_a$)-(acidic group); wherein —($L_a$)—, is an acid linker having an acid linker length of 1 to 10; provided, that at least one of $R_6$ and $R_7$ must be the group, —($L_a$)-(acidic group); and $R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

Suitable indene compounds for use in the method of the invention also include the following:

An indene-1-glyoxylamide compound or a pharmaceutically acceptable salt, solvate or prodrug derivative thereof; wherein said compound is represented by the formula (IIIf);

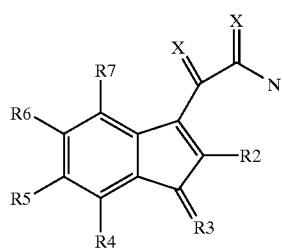

(IIIf)

X is oxygen or sulfur;

R₃ is selected from groups (a), (b) and (c) where;
(a) is $C_7$–$C_{20}$ alkyl, $C_7$–$C_{20}$ alkenyl, $C_7$–$C_{20}$ alkynyl, carbocyclic radical, or heterocyclic radical, or
(b) is a member of (a) substituted with one or more independently selected non-interfering substituents; or
(c) is the group —(L)—$R_{80}$; where, —(L)— is a divalent linking group of 1 to 12 atoms and where $R_{80}$ is a group selected from (a) or (b);

$R_2$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), —S—($C_1$–$C_2$ alkyl), or a non-interfering substituent having a total of 1 to 3 atoms other than hydrogen;

$R_6$ and $R_7$ are independently selected from hydrogen, a non-interfering substituent, or the group, —($L_a$)-(acidic group); wherein —($L_a$)—, is an acid linker having an acid linker length of 1 to 10; provided, that at least one of $R_6$ and $R_7$ must be the group, —($L_a$)-(acidic group);

$R_4$ and $R_5$ are each independently selected from hydrogen, non-interfering substituent, carbocyclic radical, carbocyclic radical substituted with non-interfering substituents, heterocyclic radical, and heterocyclic radical substituted with non-interfering substituents.

The method of making the indene compounds is as follows:

Scheme-1f

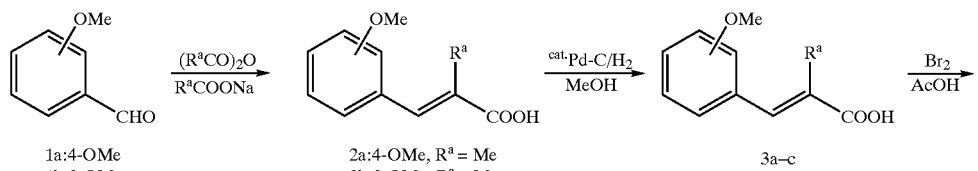

1a: 4-OMe
1b: 3-OMe

2a: 4-OMe, $R^a$ = Me
2b: 3-OMe, $R^a$ = Me
2c: 3-OMe, $R^a$ = Et

3a–c

PPA or TFA

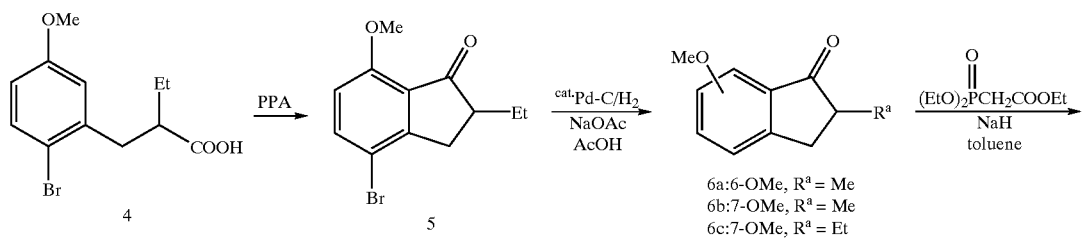

6a: 6-OMe, $R^a$ = Me
6b: 7-OMe, $R^a$ = Me
6c: 7-OMe, $R^a$ = Et

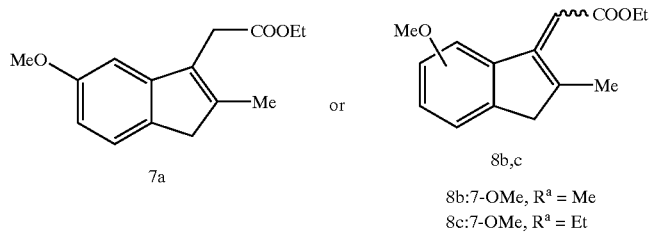

7a 8b,c
8b: 7-OMe, $R^a$ = Me
8c: 7-OMe, $R^a$ = Et

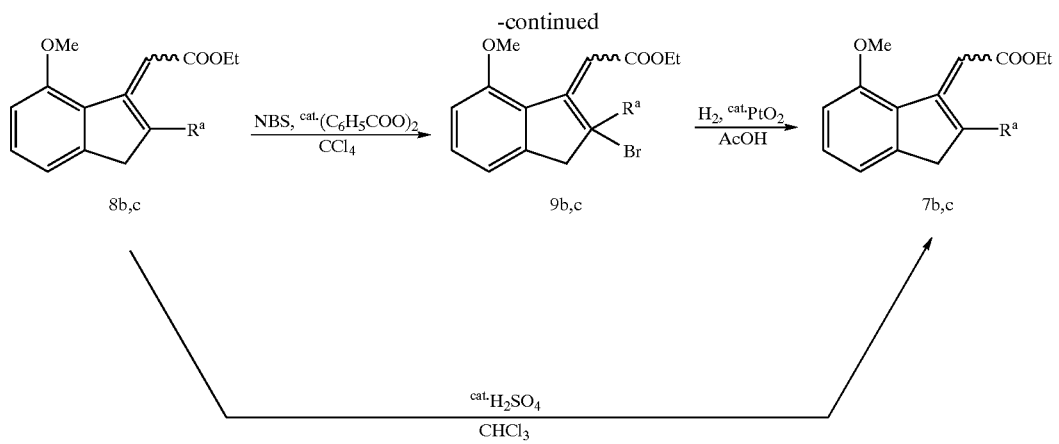

A mixture of an anisaldehyde 1, propionic anhydride, and sodium propionate is heated to produce 2 which is reduced by hydrogen in the presence of Pd/C to give 3. Acid cyclization of 3 yields 6. Alternatively, the aromatic position para to the methoxy group of 3 is blocked by bromination to give 4 which is cyclized to 5 by acid and then debrominated using hydrogen and Pd/C to give 6. Reaction of 6 with the anion of triethyl phosphonoacetate produces 7 and/or 8. Radical bromination of 8 gives 9, which on reduction with hydrogen in the presence of $PtO_2$ yields 7. Alternatively, treatment of 8 with acid gives 7.

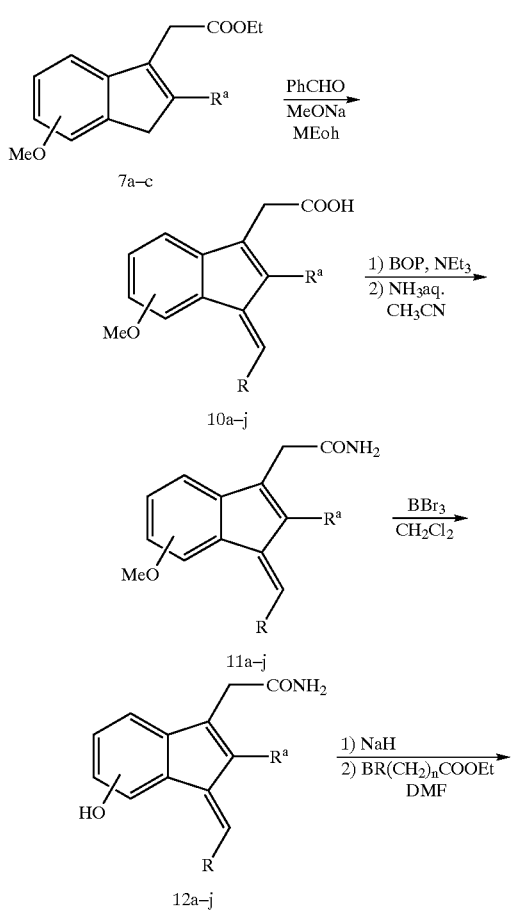

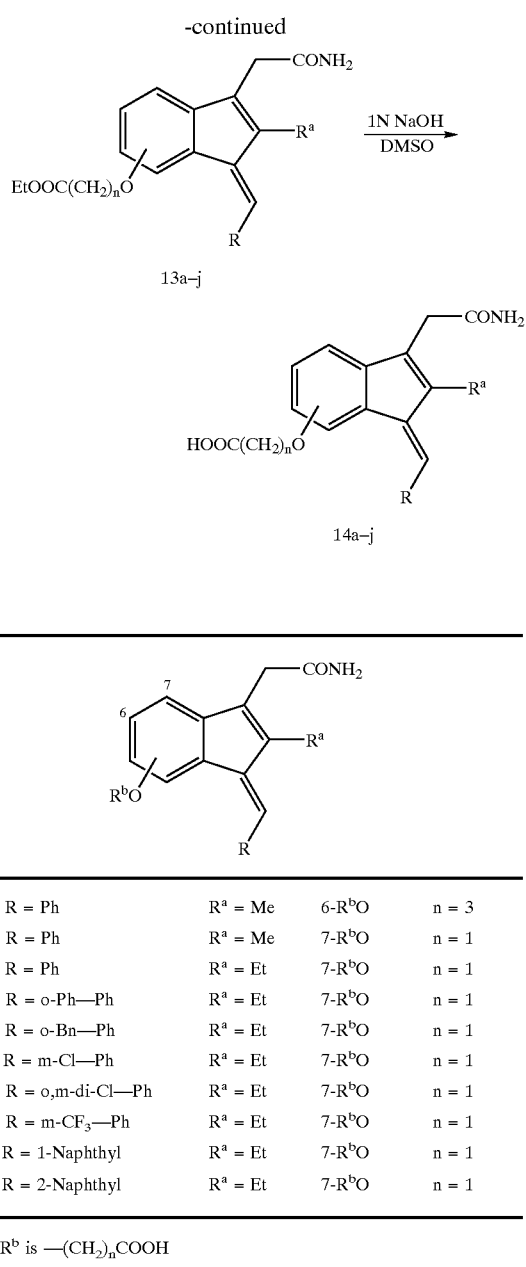

| | | | |
|---|---|---|---|
| a: R = Ph | $R^a$ = Me | 6-$R^b$O | n = 3 |
| b: R = Ph | $R^a$ = Me | 7-$R^b$O | n = 1 |
| c: R = Ph | $R^a$ = Et | 7-$R^b$O | n = 1 |
| d: R = o-Ph—Ph | $R^a$ = Et | 7-$R^b$O | n = 1 |
| e: R = o-Bn—Ph | $R^a$ = Et | 7-$R^b$O | n = 1 |
| f: R = m-Cl—Ph | $R^a$ = Et | 7-$R^b$O | n = 1 |
| g: R = o,m-di-Cl—Ph | $R^a$ = Et | 7-$R^b$O | n = 1 |
| h: R = m-$CF_3$—Ph | $R^a$ = Et | 7-$R^b$O | n = 1 |
| i: R = 1-Naphthyl | $R^a$ = Et | 7-$R^b$O | n = 1 |
| j: R = 2-Naphthyl | $R^a$ = Et | 7-$R^b$O | n = 1 | where $R^b$ is —$(CH_2)_n$COOH

Compound 7 is condensed with benzaldehyde and its derivatives in the presence of base to give 10. Indenes 10 are converted to an active ester using benzotriazo-1-yloxytris(dimethylamino)hexafluorophosphonate and then reacted with ammonium hydroxide to form 11. Demethylation of 11 with $BBr_3$ forms 12 which is O-alkylated using sodium hydride and an omega-bromoalkanoic acid ester to produce 13. Aqueous base hydrolysis of 13 yields 14.

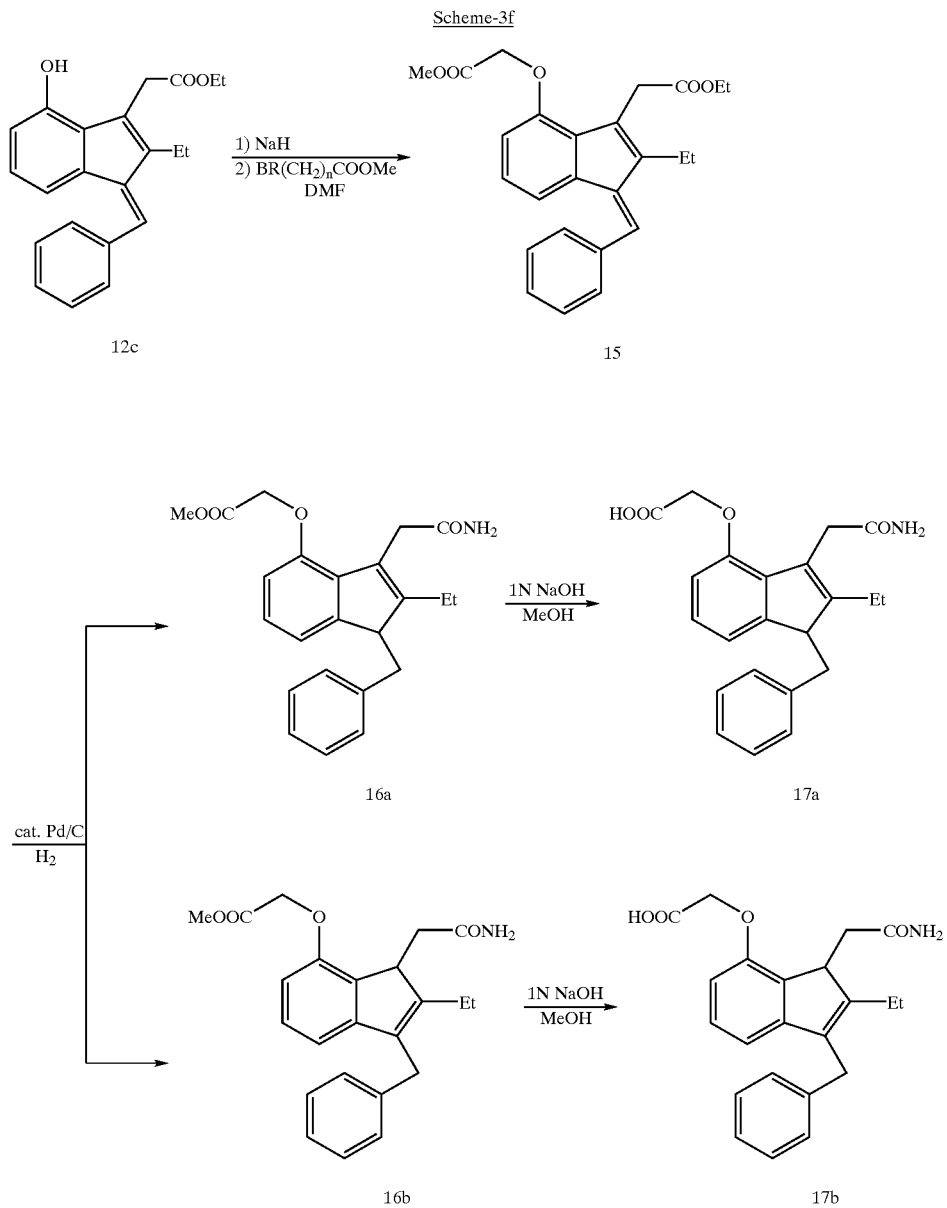

Scheme-3f

Compound 12c is O-alkylated using sodium hydride and methylbromoacetate to product 15 which is reduced by hydrogen in the presence of Pd/C to give a mixture of isomers 16a and 16b. Aqueous base hydrolysis of 16a and 16b gives 17a and 17b respectively.

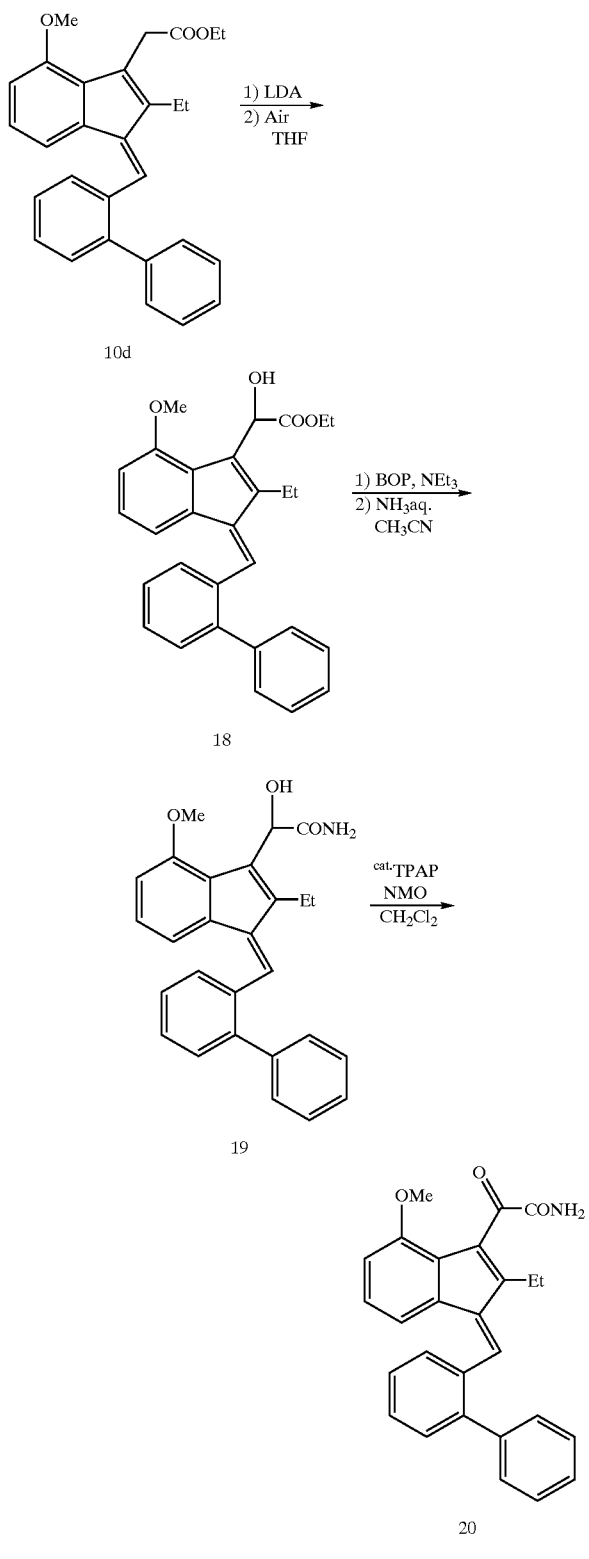

Compound 10d is treated with lithium diisopropylamine, then air is bubbled into the solution to give 18. The indene 18 is converted to an active ester using benzotriazo-1-yloxytris(dimethylamino)hexafluorophosphonate and then reacted with ammonium hydroxide to form the hydroxy acetamide 19. Compound 19 is oxidized to 20 using N-methylmorpholine N-oxide in the presence of tetrapropylammonium perruthenate.

g) Carbazole and tetrahydrocarbazole sPLA$_2$ inhibitors and methods of making these compounds are set out in U.S. patent application Ser. No. 09/063,066 filed Apr. 21, 1998 (titled, "Substituted Carbazoles and 1,2,3,4-Tetrahydrocarbazoles"), the entire disclosure of which is incorporated herein by reference. The method of the invention includes treatment of a mammal with these compounds.

The method of the invention is for treatment of a mammal, including a human, afflicted with cystic fibrosis, said method comprising administering to said human a therapeutically effective amount carbazole or tetrahydrocarbazole represented by the following:

A compound of the formula (Ie)

(Ie)

wherein;

A is phenyl or pyridyl wherein the nitrogen is at the 5-, 6-, 7- or 8-position;

one of B or D is nitrogen and the other is carbon;

Z is cyclohexenyl, phenyl, pyridyl, wherein the nitrogen is at the 1-, 2-, or 3-position, or a 6-membered heterocyclic ring having one heteroatom selected from the group consisting of sulfur or oxygen at the 1-, 2- or 3-position, and nitrogen at the 1-, 2-, 3- or 4-position;

=== is a double or single bond;

$R_{20}$ is selected from groups (a), (b) and (c) where;

(a) is —($C_5$–$C_{20}$)alkyl, —($C_5$–$C_{20}$)alkenyl, ($C_5$–$C_{20}$) alkynyl, carbocyclic radicals, or heterocyclic radicals, or (b) is a member of (a) substituted with one or more independently selected non-interfering substituents; or (c) is the group —(L)—$R_{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) and carbon, hydrogen, and oxygen only; and where $R_{80}$ is a group selected from (a) or (b);

$R^{21}$ is a non-interfering substituent;

$R^{1'}$ is —NHNH$_2$, —NH$_2$ or —CONH$_2$;

$R^{2'}$ is selected from the group consisting of —OH, and —O(CH$_2$)$_t$R5' where $R^{5'}$ is H, —CN, —NH$_2$, —CONH$_2$, —CONR$^9$R$^{10}$ —NHSO$_2$R$^{15}$; —CONHSO$_2$R$^{15}$, where R$^{15}$ is —(C$_1$–C$_6$)alkyl or —CF$_3$; phenyl or phenyl substituted with —CO$_2$H or —CO$_2$(C$_1$–C$_4$)alkyl; and —(L$_a$)-(acidic group), wherein —(L$_a$)— is an acid linker having an acid linker length of 1 to 7 and t is 1–5;

$R^{3'}$ is selected from non-interfering substituent, carbocyclic radicals, carbocyclic radicals substituted with non-interfering substituents, heterocyclic radicals, and heterocyclic radicals substituted with non-interfering substituents; or a pharmaceutically acceptable racemate, solvate, tautomer, optical isomer, prodrug derivative or salt thereof;

provided that; when $R^{3'}$ is H, $R^{20}$ is benzyl and m is 1 or 2; $R^{2'}$ cannot be —O(CH$_2$)$_m$H; and provided that when D is nitrogen, the heteroatom of Z is selected from the group consisting of sulfur or oxygen at the 1-, 2- or 3-position and nitrogen at the 1-, 2-, 3- or 4-position.

Preferred in the practice of the method of the invention are compounds represented by the formula (IIe):

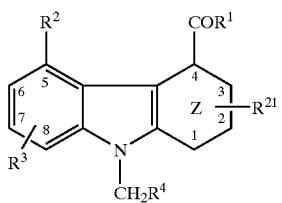

(IIe)

wherein;

Z is cyclohexenyl, or phenyl;

$R^{21}$ is a non-interfering substituent;

$R^1$ is —NHNH$_2$ or —NH$_2$;

$R^2$ is selected from the group consisting of —OH and —O(CH$_2$)$_m{}^{R5}$ where $R^5$ is H, —CO$_2$H, —CONH$_2$, —CO$_2$(C$_1$–C$_4$ alkyl);

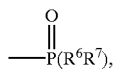

where $R^6$ and $R^7$ are each independently —OH or —O(C$_1$–C$_4$)alkyl; —SO$_3$H, —SO$_3$(C$_1$–C$_4$ alkyl), tetrazolyl, —CN, —NH$_2$, —NHSO$_2$R15; —CONHSO$_2$R15, where $R^{15}$ is —(C$_1$–C$_6$)alkyl or —CF$_3$, phenyl or phenyl substituted with —CO$_2$H or —CO$_2$(C$_1$–C$_4$)alkyl where m is 1–3;

$R^3$ is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo, or —CF$_3$; —CH$_2$OSi(C$_1$–C$_6$) alkyl, furyl, thiophenyl, —(C$_1$–C$_6$)hydroxyalkyl; or —(CH$_2$)$_n$R$^8$ where $R^8$ is H, —CONH$_2$, —NR$^9$R$^{10}$, —CN or phenyl where $R^9$ and $R^{10}$ are independently —(C$_1$–C$_4$)alkyl or -phenyl(C$_1$–C$_4$)alkyl and n is 1 to 8;

$R^4$ is H, —(C$_5$–C$_{14}$)alkyl, —(C$_3$–Cl$_4$)cycloalkyl, pyridyl, phenyl or phenyl substituted with —(C$_1$–C$_6$)alkyl, halo, —CF$_3$, —OCF$_3$, —(C$_1$–C$_4$)alkoxy, —CN, —(C$_1$–C$_4$)alkylthio, phenyl(C$_1$–C$_4$)alkyl, —(C$_1$–C$_4$) alkylphenyl, phenyl, phenoxy or naphthyl;

or a pharmaceutically acceptable racemate, solvate, tautomer, optical isomer, prodrug derivative or salt, thereof.

Preferred specific compounds including all salts and pro-drug derivatives thereof, for practicing the method of the invention are as follows:

9-benzyl-5,7-dimethoxy-1,2,3,4-tetrahydrocarbazole-4-carboxylic acid hydrazide;

9-benzyl-5,7-dimethoxy-1,2,3,4-tetrahydrocarbazole-4-carboxamide;

[9-benzyl-4-carbamoyl-7-methoxy-1,2,3,4-tetrahydrocarbazol-5-yl]oxyacetic acid sodium salt;

[9-benzyl-4-carbamoyl-7-methoxycarbazol-5-yl]oxyacetic acid;

methyl [9-benzyl-4-carbamoyl-7-methoxycarbazol-5-yl] oxyacetic acid;

9-benzyl-7-methoxy-5-cyanomethyloxy-1,2,3,4-tetrahydrocarbazole-4-carboxamide;

9-benzyl-7-methoxy-5-(1H-tetrazol-5-yl-methyl)oxy)-1,2,3,4-tetrahydrocarbazole-4-carboxamide;

{9-[(phenyl)methyl]-5-carbamoyl-2-methyl-carbazol-4-yl}oxyacetic acid;

{9-[(3-fluorophenyl)methyl]-5-carbamoyl-2-methyl-carbazol-4-yl}oxyacetic acid;

{9-[(3-methylphenyl)methyl]-5-carbamoyl-2-methyl-carbazol-4-yl}oxyacetic acid;

{9-[(phenyl)methyl]-5-carbamoyl-2-(4-trifluoromethylphenyl)-carbazol-4-yl}oxyacetic acid;

9-benzyl-5-(2-methanesulfonamido)ethyloxy-7-methoxy-1,2,3,4-tetrahydrocarbazole-4-carboxamide;

9-benzyl-4-(2-methanesulfonamido)ethyloxy-2-methoxycarbazole-5-carboxamide;

9-benzyl-4-(2-trifluoromethanesulfonamido)ethyloxy-2-methoxycarbazole-5-carboxamide;

9-benzyl-5-methanesulfonamidoylmethyloxy-7-methoxy-1,2,3,4-tetrahydrocarbazole-4-carboxamide;

9-benzyl-4-methanesulfonamidoylmethyloxy-carbazole-5-carboxamide;

[5-carbamoyl-2-pentyl-9-(phenylmethyl)carbazol-4-yl] oxyacetic acid;

[5-carbamoyl-2-(1-methylethyl)-9-(phenylmethyl)carbazol-4-yl]oxyacetic acid;

[5-carbamoyl-9-(phenylmethyl)-2-[(tri(-1-methylethyl) silyl)oxymethyl]carbazol-4-yl]oxyacetic acid;

[5-carbamoyl-2-phenyl-9-(phenylmethyl)carbazol-4-yl] oxyacetic acid[5-carbamoyl-2-(4-chlorophenyl)-9-(phenylmethyl)carbazol-4-yl]oxyacetic acid;

[5-carbamoyl-2-(2-furyl)-9-(phenylmethyl)carbazol-4-yl] oxyacetic acid;

[5-carbamoyl-9-(phenylmethyl)-2-[(tri(-1-methylethyl) silyl)oxymethyl]carbazol-4-yl]oxyacetic acid, lithium salt;

{9-[(phenyl)methyl]-5-carbamoylcarbazol-4-yl}oxyacetic acid;

{9-[(3-fluorophenyl)methyl]-5-carbamoylcarbazol-4-yl}oxyacetic acid;

{9-[(3-phenoxyphenyl)methyl]-5-carbamoylcarbazol-4-yl}oxyacetic acid;

{9-[(2-Fluorophenyl)methyl]-5-carbamoylcarbazol-4-yl}oxyacetic acid;

{9-[(2-trifluoromethylphenyl)methyl]-5-carbamoylcarbazol-4-yl}oxyacetic acid;

{9-[(2-benzylphenyl)methyl]-5-carbamoylcarbazol-4-yl}oxyacetic acid;

{9-[(3-trifluoromethylphenyl)methyl]-5-carbamoylcarbazol-4-yl}oxyacetic acid;

{9-[(1-naphthyl)methyl]-5-carbamoylcarbazol-4-yl}oxyacetic acid;

{9-[(2-cyanophenyl)methyl]-5-carbamoylcarbazol-4-yl}oxyacetic acid;

{9-[(3-cyanophenyl)methyl]-5-carbamoylcarbazol-4-yl}oxyacetic acid;

{9-[(2-methylphenyl)methyl]-5-carbamoylcarbazol-4-yl}oxyacetic acid;

{9-[(3-methylphenyl)methyl]-5-carbamoylcarbazol-4-yl}oxyacetic acid;

{9-[(3,5-dimethylphenyl)methyl]-5-carbamoylcarbazol-4-yl}oxyacetic acid;

{9-[(3-iodophenyl)methyl]-5-carbamoylcarbazol-4-yl}oxyacetic acid;

{9-[(2-Chlorophenyl)methyl]-5-carbamoylcarbazol-4-yl}oxyacetic acid;
{9-[(2,3-difluorophenyl)methyl]-5-carbamoylcarbazol-4-yl}oxyacetic acid;
{9-[(2,6-difluorophenyl)methyl]-5-carbamoylcarbazol-4-yl}oxyacetic acid;
{9-[(2,6-dichlorophenyl)methyl]-5-carbamoylcarbazol-4-yl}oxyacetic acid;
{9-[(3-trifluoromethoxyphenyl)methyl]-5-carbamoylcarbazol-4-yl}oxyacetic acid;
{9-[(2-biphenyl)methyl]-5-carbamoylcarbazol-4-yl}oxyacetic acid;
{9-[(2-Biphenyl)methyl]-5-carbamoylcarbazol-4-yl}oxyacetic acid;
the {9-[(2-Biphenyl)methyl]-5-carbamoylcarbazol-4-yl}oxyacetic acid;
[9-Benzyl-4-carbamoyl-1,2,3,4-tetrahydrocarbaole-5-yl]oxyacetic acid;
{9-[(2-Pyridyl)methyl]-5-carbamoylcarbazol-4-yl}oxyacetic acid;
{9-[(3-Pyridyl)methyl]-5-carbamoylcarbazol-4-yl}oxyacetic acid;
[9-benzyl-4-carbamoyl-8-methyl-1,2,3,4-tetrahydrocarbazol-5-yl]oxyacetic acid;
[9-benzyl-5-carbamoyl-1-methylcarbazol-4-yl]oxyacetic acid;
[9-benzyl-4-carbamoyl-8-fluoro-1,2,3,4-tetrahydrocarbazol-5-yl]oxyacetic acid;
[9-benzyl-5-carbamoyl-1-fluorocarbazol-4-yl]oxyacetic acid;
[9-benzyl-4-carbamoyl-8-chloro-1,2,3,4-tetrahydrocarbazol-5-yl]oxyacetic acid;
[9-benzyl-5-carbamoyl-1-chlorocarbazol-4-yl]oxyacetic acid;
[9-[(Cyclohexyl)methyl]-5-carbamoylcarbazol-4-yl]oxyacetic acid;
[9-[(Cyclopentyl)methyl]-5-carbamoylcarbazol-4-yl]oxyacetic acid;
5-carbamoyl-9-(phenylmethyl)-2-[[(propen-3-yl)oxy]methyl]carbazol-4-yl]oxyacetic acid;
[5-carbamoyl-9-(phenylmethyl)-2-[(propyloxy)methyl]carbazol-4-yl]oxyacetic acid;
9-benzyl-7-methoxy-5-((carboxamidomethyl)oxy)-1,2,3,4-tetrahydrocarbazole-4-carboxamide;
9-benzyl-7-methoxy-5-cyanomethyloxy-carbazole-4-carboxamide;
9-benzyl-7-methoxy-5-((1H-tetrazol-5-yl-methyl)oxy)-carbazole-4-carboxamide;
9-benzyl-7-methoxy-5-((carboxamidomethyl)oxy)-carbazole-4-carboxamide; and
[9-Benzyl-4-carbamoyl-1,2,3,4-tetrahydrocarbaole-5-yl]oxyacetic acid or a pharmaceutically acceptable racemate, solvate, tautomer, optical isomer, prodrug derivative or salt, thereof.

Other desireable carbazole compounds suitable for practicing the method of thein invention are selected from those represented by the formula (XXX):

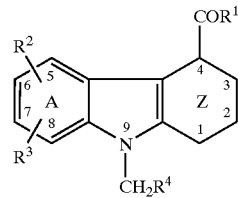

(XXX)

wherein:
R¹ is —NHNH₂, or —NH₂;
R² is selected from the group consisting of —OH and —O(CH₂)$_m$R⁵ where
R⁵ is H, —CO₂H, —CO₂(C1–C4 alkyl);

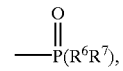

where
R⁶ and R⁷ are each independently —OH or —O(C₁–C₄)alkyl; —SO₃H, —SO₃(C₁–C₄ alkyl), tetrazolyl, —CN, —NH₂, —NHSO₂R¹⁵; —CONHSO₂R¹⁵, where R¹⁵ is —(C₁–C₆)alkyl or —CF₃, phenyl or phenyl substituted with —CO2H or —CO₂(C₁–C₄)alkyl where m is 1–3;
R³ is H, —O(C₁–C₄)alkyl, halo, —(C₁–C₆)alkyl, phenyl, —(C₁–C₄)alkylphenyl; phenyl substituted with —(C₁–C₆)alkyl, halo, or —CF₃; —CH₂OSi(C₁–C₆)alkyl, furyl, thiophenyl, —(C₁–C₆) hydroxyalkyl; or —(CH₂)$_n$R⁸ where R⁸ is H, —CONH₂, —NR⁹R¹⁰, —CN or phenyl where R⁹ and R¹⁰ are independently —(C₁–C₄)alkyl or -phenyl(C₁–C₄)alkyl and n is 1 to 8;
R⁴ is H, —(C₅–C₁₄)alkyl, —(C₃–C₁₄)cycloalkyl, pyridyl, phenyl or phenyl substituted with —(C₁–C₆) alkyl, halo, —CF₃, —OCF₃, —(C₁–C₄)alkoxy, —CN, —(C₁–C₄)alkylthio, phenyl(C1–C₄)alkyl, —(C₁–C₄)alkylphenyl, phenyl, phenoxy or naphthyl;
A is phenyl or pyridyl wherein the nitrogen is at the 5-, 6-, 7- or 8-position;
Z is cyclohexenyl, phenyl, pyridyl wherein the nitrogen is at the 1-, 2- or 3-position or a 6-membered heterocyclic ring having one heteroatom selected from the group consisting of sulfur or oxygen at the 1-, 2- or 3-position and nitrogen at the 1-, 2-, 3- or 4-position, or
wherein one carbon on the heterocyclic ring is optionally substituted with =O;
or a pharmaceutically acceptable racemate, solvate, tautomer, optical isomer, prodrug derivative or salt thereof;
provided that one of A or Z is a heterocyclic ring.

Further desirable specific compounds suitable for the method of the invention are selected from the following: (R,S)-(9-benzyl-4-carbamoyl-1-oxo-3-thia-1,2,3,4-tetrahydrocarbazol-5-yl)oxyacetic acid; (R,S)-(9-benzyl-4-carbamoyl-1-oxo-3-thia-1,2,3,4-tetrahydrocarbazol-5-yl)oxyacetic acid; [N-benzyl-1-carbamoyl-1-aza-1,2,3,4-tetrahydrocarbazol-8-yl]oxyacetic acid; 4-methoxy-6-methoxycarbonyl-10-phenylmethyl-6,7,8,9-tetrahydropyrido[1,2-a]indole; (4-carboxamido-9-phenylmethyl-4,5-dihydrothiopyrano[3,4-b]indol-5-yl)oxyacetic acid; 3,4-dihydro-4-carboxamidol-5-methoxy-9- phenylmethylpyrano[3,4-b]indole; 2-[(2,9 bis-benzyl-4-carbamoyl-1,2,3,4-tetrahydro-beta-carbolin-5-yl)oxy]acetic acid or a pharmaceutically acceptable racemate, solvate, tautomer, optical isomer, prodrug derivative or salt thereof.

Particularly preferred compounds for the treatment of cystic fibrosis are represented by the formulae (Xe) and (XIe) below:

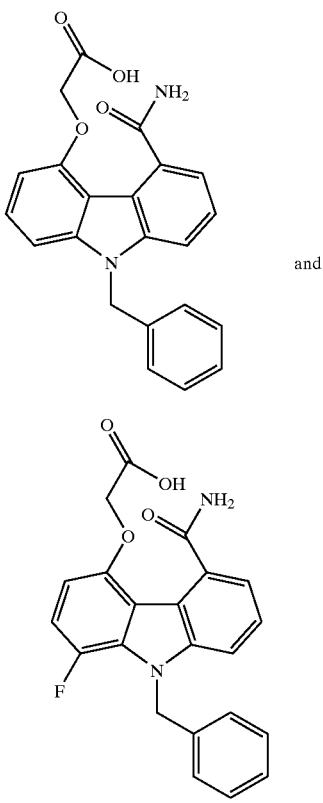

For all of the above compounds of the carbazole or tetrahydrocarbazole type it is advantageous to use them in their (i)acid form, or (ii) pharmaceutically acceptable (e.g., Na, K) form, or (iii) and prodrugs derivatives (e.g., methyl ester, ethyl ester, n-butyl ester, morpholino ethyl ester).

Prodrugs are derivatives of sPLA$_2$ inhibitors used in the method of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Specific preferred prodrugs are ester prodrugs inclusive of methyl ester, ethyl ester, n-propyl ester, isopropyl ester, n-butyl ester, sec-butyl, tert-butyl ester, N,N-diethylglycolamido ester, and morpholino-N-ethyl ester. Methods of making ester prodrugs are disclosed in U.S. Pat. No. 5,654,326. Additional methods of prodrug synthesis are disclosed in U.S. Provisional Patent Application Serial No. 60/063280 filed Oct. 27, 1997 (titled, N,N-diethylglycolamido ester Prodrugs of Indole sPLA2 Inhibitors), the entire disclosure of which is incorporated herein by reference; U.S. Provisional Patent Application Serial No. 60/063646 filed Oct. 27, 1997 (titled, Morpholino-N-ethyl Ester Prodrugs of Indole sPLA2 Inhibitors), the entire disclosure of which is incorporated herein by reference; and U.S. Provisional Patent Application Serial No. 60/063284 filed Oct. 27, 1997 (titled, Isopropyl Ester Prodrugs of Indole sPLA$_2$ Inhibitors), the entire disclosure of which is incorporated herein by reference.

Carbazole and tetrahydrocarbazole sPLA$_2$ inhibitor compounds useful for practicing the method of the invention may be made by the following general methods:

The compounds of formula Ie where Z is cyclohexene are prepared according to the following reaction Schemes Ig(a) and (c).

Scheme Ig(a)

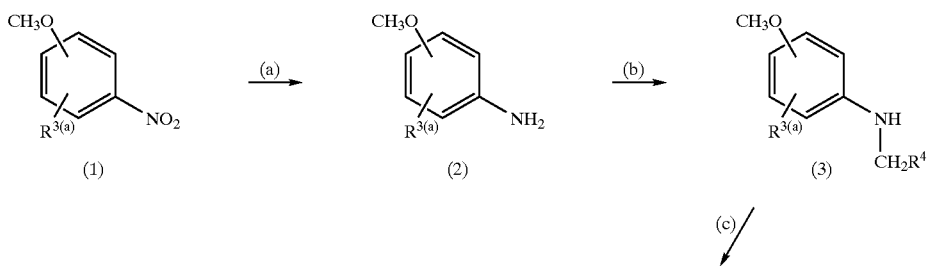

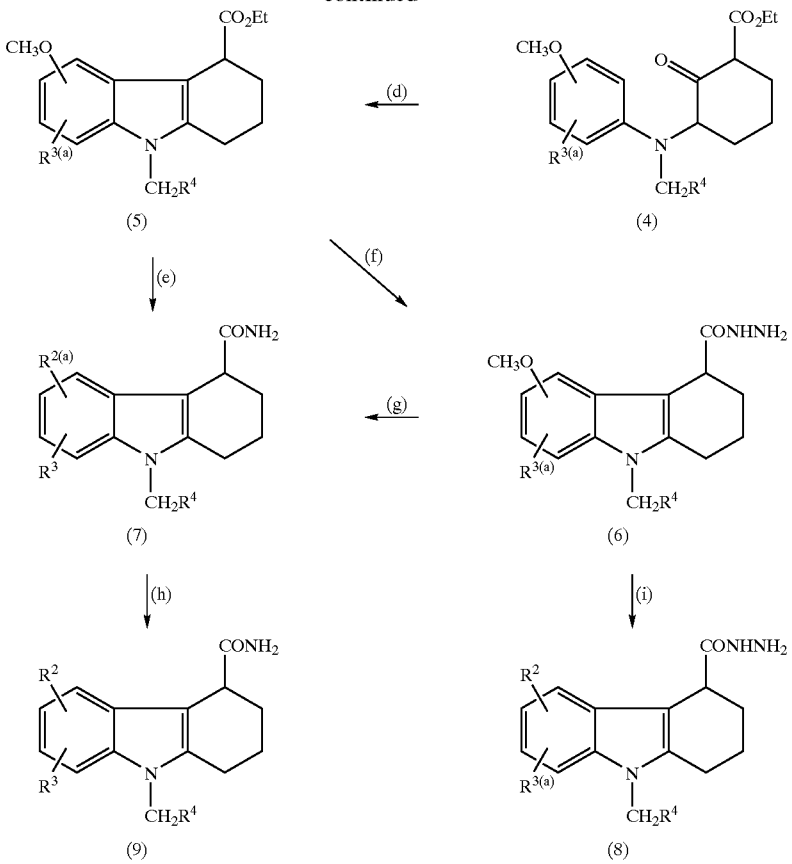

wherein;
R¹ is —NH₂, R³(a) is H, —O(C₁–C₄)alkyl, halo, —(C₁–C₆)alkyl, phenyl, —(C₁–C₄)alkylphenyl; phenyl substituted with —(C₁–C₆)alkyl, halo, or —CF₃; —CH₂OSi(C₁–C₆)alkyl, furyl, thiophenyl, —(C₁–C₆) hydroxyalkyl, —(C₁–C₆)alkoxy(C₁–C₆)alkyl, —(C₁–C₆)alkoxy(C₁–C₆)alkenyl; or —(CH₂)ₙR⁸ where R⁸ is H, —CONH₂, —NR⁹R¹⁰, —CN or phenyl where R⁹ and R¹⁰ are independently hydrogen, —CF₃, phenyl, —(C₁–C₄)alkyl, —(C₁–C₄)alkylphenyl or -phenyl(C₁–C₄)alkyl and n is 1 to 8;

when R¹ is —NHNH₂, R³(a) is H, —O(C₁–C₄)alkyl, halo, —(C₁–C₆)alkyl, phenyl, —(C₁–C₄)alkylphenyl; phenyl substituted with —(C₁–C₆)alkyl, halo or —CF₃; —CH₂OSi(C₁–C₆)alkyl, furyl, thiophenyl, —(C₁–C₆) hydroxyalkyl, —(C₁–C₆)alkoxy(C₁–C₆)alkyl, —(C₁–C₆)alkoxy(C₁–C₆)alkenyl; or —(CH₂)ₙR⁸ where R⁸ is H, —NR⁹R¹⁰, —CN or phenyl where R⁹ and R¹⁰ are independently hydrogen, —CF₃, phenyl, —(C₁–C₄)alkyl, —(C₁–C₄)alkylphenyl or -phenyl (C₁–C₄)alkyl and n is 1 to 8;

R²(a) is —OCH₃ or —OH.

An appropriately substituted nitrobenzene (1) can be reduced to the aniline (2) by treatment with a reducing agent, such as hydrogen in the presence of Pd/C, preferably at room temperature.

Compound (2) is N-alkylated at temperatures of from about 0 to 20° C. using an alkylating agent such as an appropriately substituted aldehyde and sodium cyanoborohydride to form (3). Alternately, an appropriately substituted benzyl halide may be used for the first alkylation step. The resulting intermediate is further N-alkylated by treatment with 2-carbethoxy-6-bromocyclohexanone, preferably at temperatures of about 80 ° C. to yield (4) or by treatment with potassium hexamethyldisilazide and the bromoketoester.

The product (4) is cyclized to the tetrahydrocarbazole (5) by refluxing with ZnCl₂ in benzene for from about 1 to 2 days, preferably at 80° C. (Ref 1). Compound (5) is converted to the hydrazide (6) by treatment with hydrazine at temperatures of about 100° C., or to the amide (7) by reacting with methylchloroaluminum amide in benzene. (Ref 2) Alternatively, (7) may be produced by treatment of (6) with Raney nickel active catalyst.

It will be readily appreciated that when R³(a) is:

conversion to the amide will also be achieved in this procedure.

Compounds (6) and (7) may be dealkylated, preferably at 0° C. to room temperature, with a dealkylating agent, such as boron tribromide or sodium thioethoxide, to give compound (7) where R²(a) is —OH, which may then be further converted to compound (9), by realkylating with a base, such as sodium hydride, and an alkylating agent, such as Br(CH₂)ₘR⁵, where R⁵ is the carboxylate or phosphonic diester or nitrile as defined above. Conversion of R² to the carboxylic acid may be accomplished by treatment with an aqueous base. When R² is nitrile, conversion to the tetrazole may be achieved by reacting with tri-butyl tin azide or conversion to the carboxamide may be achieved by reacting with basic hydrogen peroxide. When $R^2$ is the phosphonic diester, conversion to the acid may be achieved by reacting with a dealkylating agent such as trimethylsilyl bromide. The monoester may be accomplished by reacting the diester with an aqueous base.

When $R^2$ and $R^3$ are both methoxy, selective demethylation can be achieved by treating with sodium ethanethiolate in dimethylformamide at 100° C.

Ref 1 Julia, M.; Lenzi, J. Preparation d'acides tetrahydro-1,2,3,4-carbazole-1 ou -4. *Bull.Soc.Chim.France,* 1962, 2262–2263.

Ref 2 Levin, J. I.; Turos, E.; Weinreb, S. M. An alternative procedure for the aluminum-mediated conversion of esters to amides. *Syn.Comm.,* 1982, 12, 989–993.

An alternative synthesis of intermediate (5) is shown in Scheme I(b), as follows.

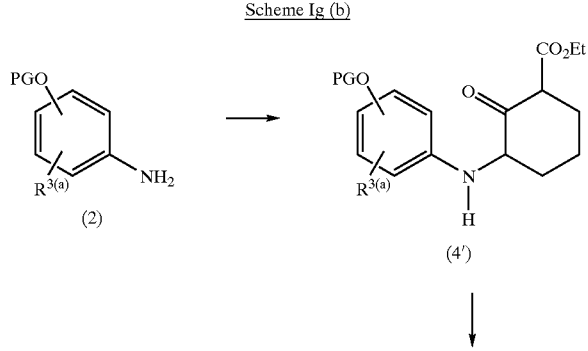

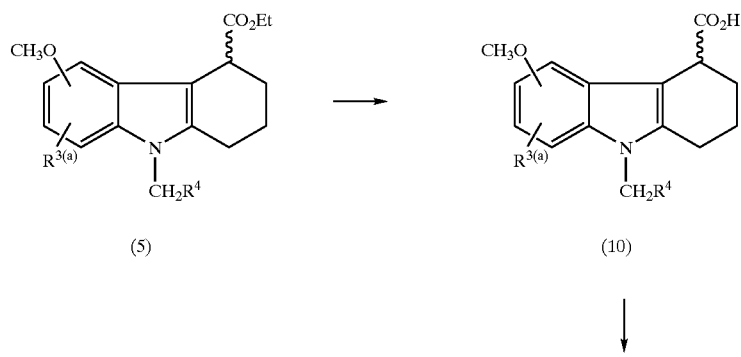

where

PG is a protecting group;

$R^{3a}$ is as defined in Scheme 1, above.

The aniline (2) is N-alkylated with 2-carbethoxy-6-bromocyclohexanone in dimethyl formamide in the presence of sodium bicarbonate for 8–24 hours at 50° C. Preferred protecting groups include methyl, carbonate, and silyl groups, such as t-butyldimethylsilyl. The reaction product (4') is cyclized to (5') using the $ZnCl_2$ in benzene conditions described in Scheme I(a), above. N-alkylation of (5') to yield (5) is accomplished by treatment with sodium hydride and the appropriate alkyl halide in dimethylformamide at room temperature for 4–8 hours.

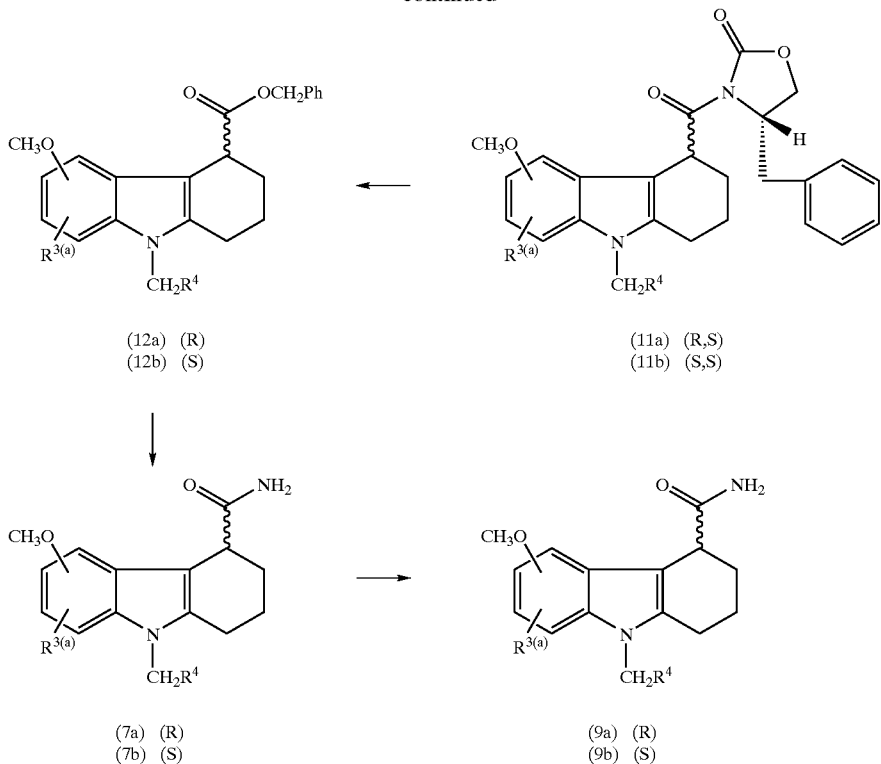

(12a) (R)
(12b) (S)

(11a) (R,S)
(11b) (S,S)

(7a) (R)
(7b) (S)

(9a) (R)
(9b) (S)

$R^{3(a)}$ is as defined in Scheme Ig.

As discussed in Scheme I above, carbazole (5) is hydrolyzed to the carboxylic acid (10) by treatment with an aqueous base, preferably at room temperature to about 100° C. The intermediate is then converted to an acid chloride utilizing, for example, oxalyl chloride and dimethylformamide, and then further reacted with a lithium salt of (S) or (R)-4-alkyl-2-oxazolidine at a temperature of about −75° C., to give (11a) and (11b), which are separable by chromatography.

The diastereomers are converted to the corresponding enantiomeric benzyl esters (12) by brief treatment at temperatures of about 0° C. to room temperature with lithium benzyl oxide. (Ref 3) The esters (12) are then converted to (7) preferably by treatment with methylchloroaluminum amide (Ref 2, above) or, alternately, by hydrogenation using, for example, hydrogen and palladium on carbon, as described above, to make the acid and then reacting with an acyl azide, such as diphenylphosphoryl azide followed by treatment with ammonia. Using the procedure described above in Scheme I, compound (9a) or (9b) may be accomplished.

Ref 3 Evans, D. A.; Ennis, M. D.; Mathre, D. J. Asymmetric alkylation reactions of chiral imide enolates. A practical approach to the enantioselective synthesis of alpha-substituted carboxylic acid derivatives. *J.Am.Chem.Soc.*, 1982, 104, 1737–1738.

Compounds of formula Ie where Z is phenyl can be prepared as follows in Schemes III(a)–(f), below.

Scheme III (a)

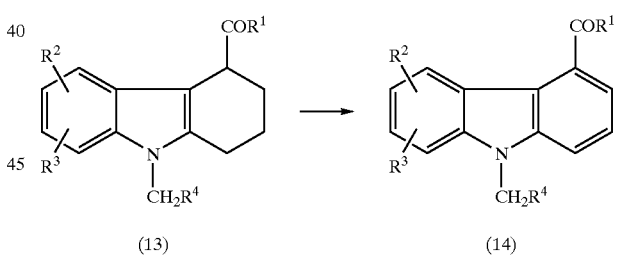

(13)    (14)

A 1,2,3,4-tetrahydrocarbazole-4-carboxamide or 4-carboxhydrazide (13) is dehydrogenated by refluxing in a solvent such as carbitol in the presence of Pd/C to produce the carbazole-4-carboxamide. Alternately, treatment of (13) with DDQ in an appropriate solvent such as dioxane yields carbozole (14).

Depending on the substituent pattern oxidation as described above may result in de-alkylation of the nitrogen. For example when $R^3$ is substituted at the 8-position with methyl, oxidation results in dealkylation of the nitrogen which may be realkylated by treatment with sodium hydride and the appropriate alkyl halide as described in Scheme I(a)above to prepare the deired product (14).

Scheme III (b)

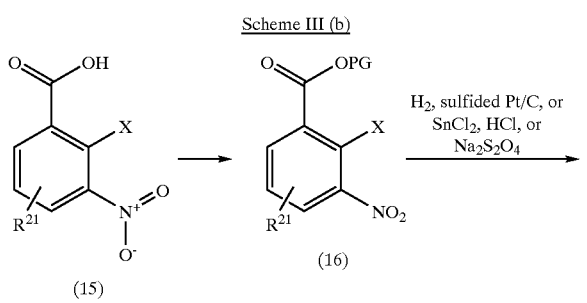

(15) → (16)

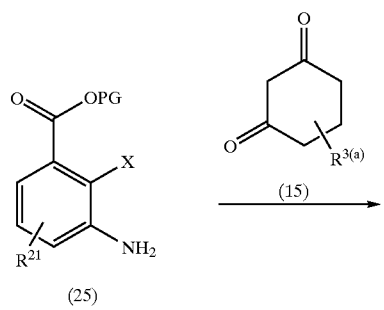

(25) + (15) →

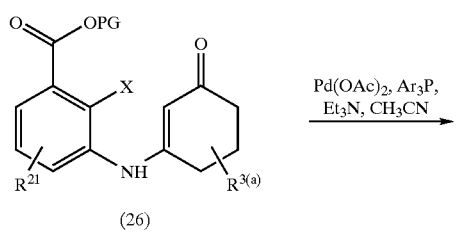

(26)

Pd(OAc)$_2$, Ar$_3$P, Et$_3$N, CH$_3$CN

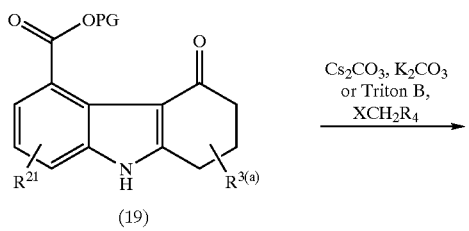

(19)

Cs$_2$CO$_3$, K$_2$CO$_3$ or Triton B, XCH$_2$R$^4$

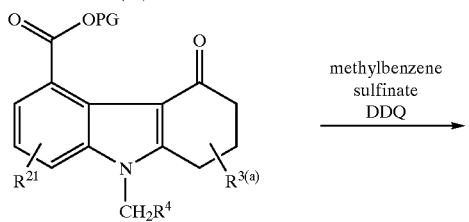

(20)

methylbenzene sulfinate DDQ

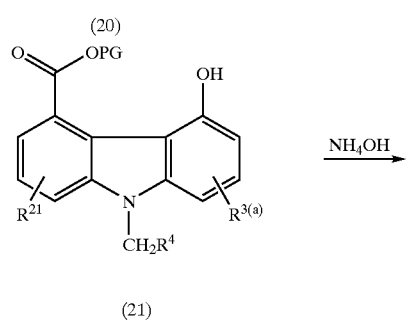

(21)

NH$_4$OH

-continued

(22) → XR, K$_2$CO$_3$

(23) → 1.) NaOH  2.) Salification (24)

R$^{3(a)}$ is as defined in Scheme I (a) above
PG is an acid protecting group
X is halo Benzoic acid derivative (16) where X is preferably chlorine, bromine or iodine and the protecting group is preferably —CH$_3$, are reduced to the corresponding aniline (25) with a reducing agent, such as stannous chloride in the presence of acid under the general conditions of Sakamoto et al, *Chem Pharm. Bull.* 35 (5), 1823–1828 (1987).

Alternatively, reduction with sodium dithionite in the presence of a base, such as sodium carbonate in a noninterfering solvent, such as water, ethanol, and/or tetrahydrofuran affords starting material (16).

Alternatively, reduction by hydrogenation over a sulfided platinum catalyst supported on carbon with hydrogen at 1 to 60 atmospheres in a noninterfering solvent, preferably ethyl acetate, to form a starting material (16).

The reactions are conducted at temperatures from about 0 to 100° C. preferably at ambient temperature, and are substantially complete in about 1 to 48 hours depending on conditions.

The aniline (25) and dione (15) are condensed under dehydrating conditions, for example, using the general procedure of Iida, et al., (Ref 5), with or without a noninterfering solvent, such as toluene, benzene, or methylene chloride, under dehydrating conditions at a temperature about 10 to 150° C. The water formed in the process can be removed by distillation, azetropic removal via a Dean-Stark apparatus, or the addition of a drying agent, such as molecular sieves, magnesium sulfate, calcium carbonate, sodium sulfate, and the like.

The process can be performed with or without a catalytic amount of an acid, such a p-toluenesulfonic acid or methanesulfonic acid. Other examples of suitable catalysts include hydrochloric acid, phenylsulfonic acid, calcium chloride, and acetic acid.

Examples of other suitable solvents include tetrahydrofuran, ethyl acetate, methanol, ethanol, 1,1,2,2-tetrachloroethane, chlorobenzene, bromobenzene, xylenes, and carbotetrachloride.

The condensation of the instant process is preferably carried out neat, at a temperature about 100 to 150° C. with the resultant water removed by distillation via a stream of inert gas, such as, nitrogen or argon.

The reaction is substantially complete in about 30 minutes to 24 hours.

Intermediate (26) may then be readily cyclized in the presence of a palladium catalyst, such as Pd(OAc)$_2$ or Pd(PPh$_3$)$_4$ and the like, a phosphine, preferably a trialkyl- or triarylphosphine, such as triphenylphosphine, tri-o-tolylphosphine, or tricyclohexylphosphine, and the like, a base, such as, sodium bicarbonate, triethylamine, or diisopropylethylamine, in a noninterfering solvent, such as, acetonitrile, triethylamine, or toluene at a temperature about 25 to 200° C. to form (19).

Examples of other suitable solvents include tetrahydrofuran, benzene, dimethylsulfoxide, or dimethylformamide.

Examples of other suitable palladium catalysts include Pd(PPh$_3$)Cl$_2$, Pd(OCOCF$_3$)$_2$, [(CH$_3$C$_6$H$_4$)$_3$P]$_2$PdCl$_2$, [(CH$_3$CH$_2$)$_3$P]$_2$PdCl$_2$, [(C$_6$H$_{11}$)$_3$P]$_2$PdCl$_2$, and [(C$_6$H$_5$)$_3$P]$_2$PdBr$_2$.

Examples of other suitable phosphines include triisopropylphosphine, triethylphosphine, tricyclopentylphosphine, 1,2-bis(diphenylphosphino)ethane, 1,3-bis(diphenylphosphino)propane, and 1,4-bis(diphenylphosphino)butane.

Examples of other suitable bases include tripropyl amine, 2,2,6,6-tetramethylpiperidine, 1,5-diazabicyclo[2.2.2]octane (DABCO), 1,8-diazabicyclo[5.4.0]undec-7-ene (DBU), 1,5-diazabicyclo[4.3.0]non-5-ene, (DBN) sodium carbonate, potassium carbonate, and potassium bicarbonate.

The cyclization of the instant process is preferably carried out with palladium(II)acetate as catalyst in the presence of either triphenylphosphine, tri-o-tolylphosphine, 1,3-bis(diphenylphosphino)propane, or tricyclohexylphosphine in acetonitrile as solvent and triethylamine as base at a temperature about 50 to 150° C. The reaction is substantially complete in about 1 hour to 14 days.

Alternatively, a preferred process for cyclization consists of the reaction of intermediate (26) with a palladacycle catalyst such as trans-di($\mu$-acetato)-bis[o-(di-o-tolylphosphino)benzyl]dipalladium (II) in a solvent such as dimethylacetamide (DMAC) at 120–140° C. in the presence of a base such as sodium acetate.

Intermediate (19) may be alkylated with an alkylating agent XCH$_2$R$^4$, where X is halo in the presence of a base to form (20). Suitable bases include potassium carbonate, sodium carbonate, lithium carbonate, cesium carbonate, sodium bicarbonate, potassium bicarbonate, potassium hydroxide, sodium hydroxide, sodium hydride, potassium hydride, lithium hydride, and Triton B (N-benzyltrimethylammonium hydroxide).

The reaction may or may not be carried out in the presence of a crown ether. Potassium carbonate and Triton B are preferred. The amount of alkylating agent is not critical, however, the reaction is best accomplished using an excess of alkyl halide relative to the starting material.

A catalytic amount of an iodide, such as sodium iodide or lithium iodide may or may not be added to the reaction mixture. The reaction is preferably carried out in an organic solvent, such as, acetone, dimethylformamide, dimethylsulfoxide, or acetonitrile. Other suitable solvents include tetrahydrofuran, methyl ethyl ketone, and t-butyl methyl ether.

The reaction is conducted at temperatures from about −10 to 100° C. preferably at ambient temperature, and is substantially complete in about 1 to 48 hours depending on conditions. Optionally, a phase transfer reagent such as tetrabutylammonium bromide or tetrabutylammonium chloride may be employed.

Intermediate (20) May by dehydrogenated by oxidation with 2,3-dichloro-5,6-dicyano-1,4-benzoquinone in a noninterfering solvent to form (21).

Suitable solvents include methylene chloride, chloroform, carbon tetrachloride, diethyl ether, methyl ethyl ketone, and t-butyl methyl ether. Toluene, benzene, dioxane, and tetrahydrofuran are preferred solvents. The reaction is carried out at a temperature about 0 to 120° C. Temperatures from 50 to 120° C. are preferred. The reaction is substantially complete in about 1 to 48 hours depending on conditions.

Intermediate (21) may be aminated with ammonia in the presence of a noninterfering solvent to form a(22). Ammonia may be in the form of ammonia gas or an ammonium salt, such as ammonium hydroxide, ammonium acetate, ammonium trifluoroacetate, ammonium chloride, and the like. Suitable solvents include ethanol, methanol, propanol, butanol, tetrahydrofuran, dioxane, and water. A mixture of concentrated aqueous ammonium hydroxide and tetrahydrofuran or methanol is preferred for the instant process. The reaction is carried out at a temperature about 20 to 100° C. Temperatures from 50 to 60° C. are preferred. The reaction is substantially complete in about 1 to 48 hours depending on conditions.

Alkylation of (22) is achieved by treatment with an alkylating agent of the formula XCH$_2$R$^9$ where X is halo and R$^{70}$ is —CO$_2$R$^{71}$, —SO$_3$R$^{71}$, —P(O)(OR$^{71}$)$_2$, or —P(O)(O(R$^{71}$)H, where R$^{71}$ is an acid protecting group or a prodrug function, in the presence of a base in a noninterfering solvent to form (23). Methyl bromoacetate and t-butyl bromoacetate are the preferred alkylating agents.

Suitable bases include potassium carbonate, sodium carbonate, lithium carbonate, cesium carbonate, sodium bicarbonate, potassium bicarbonate, potassium hydroxide, sodium hydroxide, sodium hydride, potassium hydride, lithium hydride, and Triton B (N-benzyltrimethylammonium hydroxide). The reaction may or may not be carried out in the presence of a crown ether. Cesium carbonate and Triton B are preferred.

The amount of alkylating agent is not critical, however, the reaction is best accomplished using an excess of alkyl halide relative to the starting material. The reaction is preferably carried out in an organic solvent, such as, acetone, dimethylformamide, dimethylsulfoxide, or acetonitrile. Other suitable solvents include tetrahydrofuran, methyl ethyl ketone, and t-butyl methyl ether.

The reaction is conducted at temperatures from about −10 to 100° C. preferably at ambient temperature, and is substantially complete in about 1 to 48 hours depending on conditions. Optionally, a phase transfer reagent such as tetrabutylammonium bromide or tetrabutylammonium chloride may be employed.

Intermediate (23) may be optionally hydrolyzed with a base or acid to form desired product (24) and optionally salified.

Hydrolysis of (23) is achieved using a base such as sodium hydroxide, potassium hydroxide, lithium hydroxide, aqueous potassium carbonate, aqueous sodium carbonate, aqueous lithium carbonate, aqueous potassium bicarbonate, aqueous sodium bicarbonate, aqueous lithium bicarbonate, preferably sodium hydroxide and a lower alcohol solvent, such as, methanol, ethanol, isopropanol, and the like. Other suitable solvents include acetone, tetrahydrofuran, and dioxane.

Alternatively, the acid protecting group may be removed by organic and inorganic acids, such as trifluoroacetic acid and hydrochloric acid with or without a noninterferring solvent. Suitable solvents include methylene chloride, tetrahydrofuran, dioxane, and acetone. The t-butyl esters are preferably removed by neat trifluoroacetic acid.

The reaction is conducted at temperatures from about −10 to 100° C. preferably at ambient temperature, and is substantially complete in about 1 to 48 hours depending on conditions.

The starting material (16) is prepared by esterifying compound (15) with a alkyl halide=XPG; where X is halo and PG is an acid protecting group, in the presence of a base, preferably potassium carbonate or sodium cabonate, in a noninterferring solvent, preferably dimethylformamide or dimethylsulfoxide. The preferred alkyl halide is methyl iodide. The reaction is conducted at temperatures from about 0 to 100° C. preferably at ambient temperature, and is substantially complete in about 1 to 48 hours depending on conditions.

Alternatively the starting material (16) may be prepared by condensation with an alcohol HOPG, where PG is an acid protecting group, in the presence of a dehydrating catalyst such as, dicyclohexylcarbodiimide (DCC) or carbonyl diimidazole.

In addition, U.S. Pat. No. 4,885,338 and Jpn. Kokai Tokkyo Koho 05286912, November 1993 Hesei teach a method for preparing 2-fluoro-5-methoxyaniline derivatives.

Scheme IIIg(c)

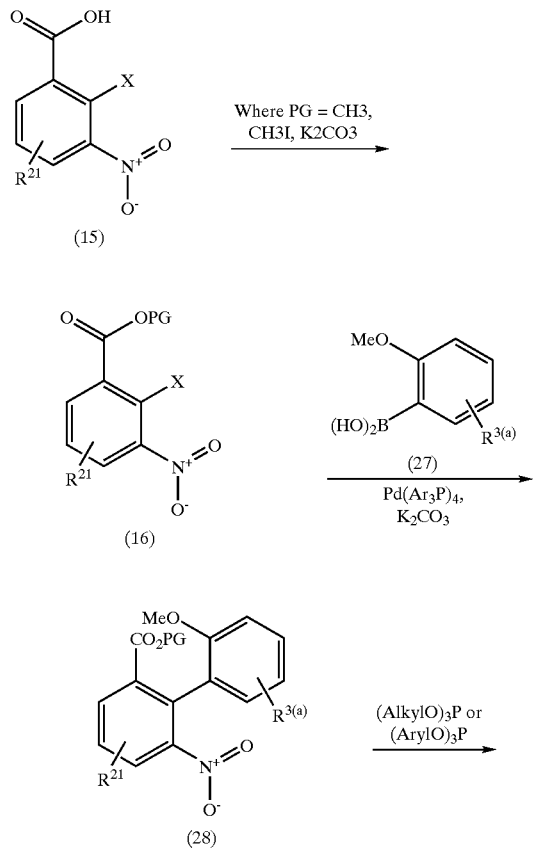

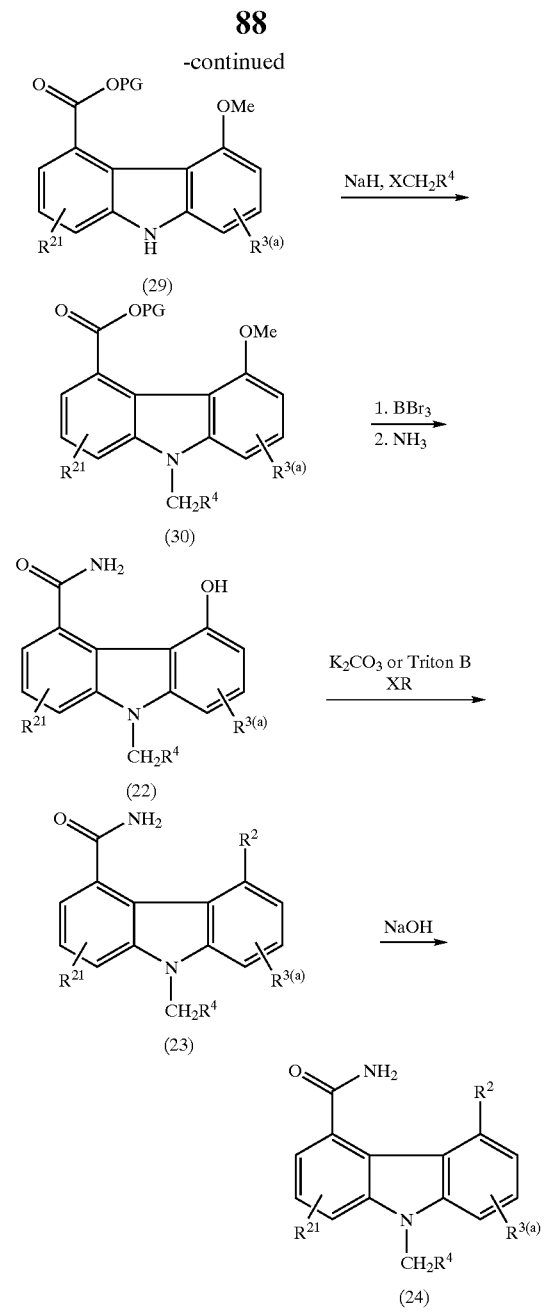

R is as defined in Scheme IIIg(b), $R^{3(a)}$ is as defined in Scheme Ig(a), above; and X is halo.

Benzoic acid derivatives (16) (X=Cl, Br, or I) and boronic acid derivative (27) (either commercially available or readily prepared by known techniques from commercially available starting materials) are condensed under the general procedure of Miyaura, et al., (Ref 8a) or Trecourt, et al., (Ref 8b) in the presence of a palladium catalyst, such as $Pd(Ph_3P)_4$, a base, such as sodium bicarbonate, in an inert solvent, such as THF, toluene or ethanol, to afford compound (28).

Compound (28) is converted to the carbazole product (29) by treatment with a trialkyl or triaryl phosphite or phosphine, such as, triethylphosphite or triphenyl phosphine, according to the general procedure of Cadogan, et al. (Ref 6).

Compound (29) is N-alkylated with an appropriately substituted alkyl or aryl halide $XCH_2R^4$ in the presence of a base, such as sodium hydride or potassium carbonate, in a noninterfering solvent, such as toluene, dimethylformamide, or dimethylsulfoxide to afford carbazole (30).

Compound (30) is converted to the corresponding amide (22) by treatment with boron tribromide or sodium thioethoxide, followed by ammonia or an ammonium salt, such as ammonium acetate, in an inert solvent, such as water or alcohol, or with methylchloroaluminum amide in an inert solvent, such as toluene, at a temperature between 0 to 110° C.

When $R^{3(a)}$ is substituted at the 8-position with chloro, de-alkylation of (30) with boron tribromide results in de-benzylation of the nitrogen as described above. Alkylation may be readily accomplished in a two step process. First, an O-alkylation by treatment with a haloalkyl acetate such as methyl bromo acetate using sodium hydride in tetrahydrofuran, followed by N-alkylation using for example a base such as sodium hydride and an appropriately substituted alkyl or aryl halide in dimethoxy formamide. Compound (22) can be converted to product carbazole product (24) as described previously in Scheme IIIg(b) above.

Conversion to the desired prodrug may be accomplished by techniques known to the skilled artisan, such as for example, by treatment with a primary or secondary halide to make an ester prodrug.

Scheme IIIg(d)

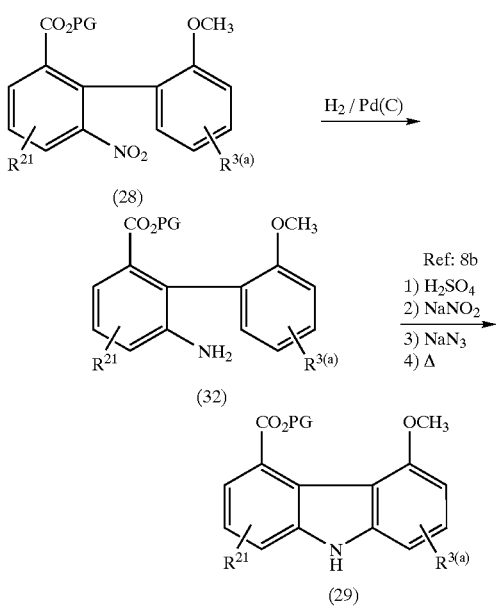

Alternatively, reduction of the nitro group of compound (28) with a reducing agent, such as hydrogen in the presence of palladium on carbon, in a noninterfering solvent, such as ethanol, at 1 to 60 atmospheres, at a temperature of 0 to 60° C. affords the corresponding aniline (32). Compound (32) is converted to the carbazole (29) according to the general procedure described by Trecourt, et al. (Ref 8b). The aniline is treated with sulfuric acid and sodium nitrite, followed by sodium azide to form an intermediate azide which is cyclized to carbazole (29) by heating in an inert sovent, such as toluene. Compound (29) is converted to carbazole product (24) as described previously in Schemes IIIg(b) and IIIg(c).

References 8) a. N. Miyaura, et al., Synth. Commun. 11, 513 (1981) b. F. Trecourt, et al., Tetrahedron, 51, 11743 6)
6) J. Cadogan et al., J. Chem. Soc., 4831 (1965)

Scheme IIIg(e)

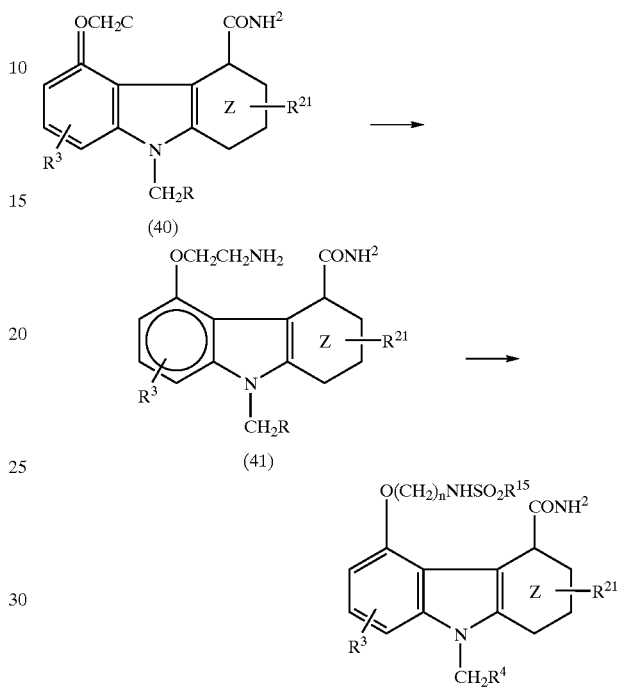

In an aprotic solvent, preferably tetrahydrofuran, reduction of (40) is achieved using a reducing agent such as aluminum trihydride. Preferably, the reaction is conducted under inert atmosphere such as nitrogen, at room temperature.

Sulfonylation may be achieved with an appropriate acylating agent in the presence of an acid scavenger such as triethyl amine.

Scheme IIIg(f)

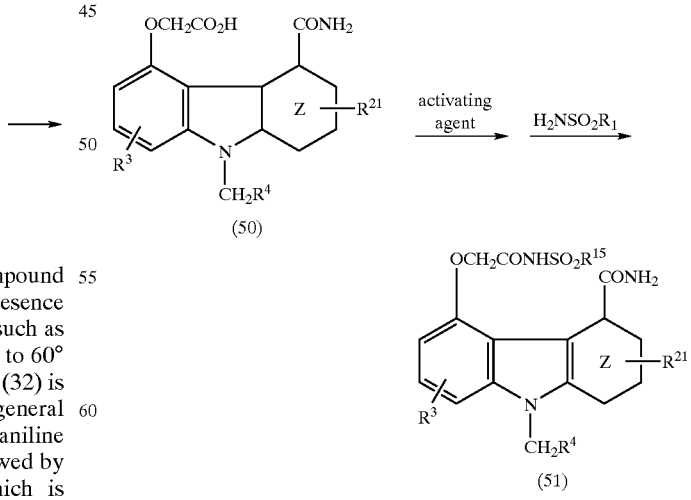

In a two-step, one-pot process, intermediate (50), prepared as described in Scheme I(a) above, is first activated with an activating agent such as carbonyl diimidazole. The reaction is preferably run in an aprotic polar or non-polar solvent such as tetrahydrofuran. Acylation with the activated intermediate is accomplished by reacting with $H_2NSOR^{15}$ in the presence of a base, preferably diazabicycloundecene.

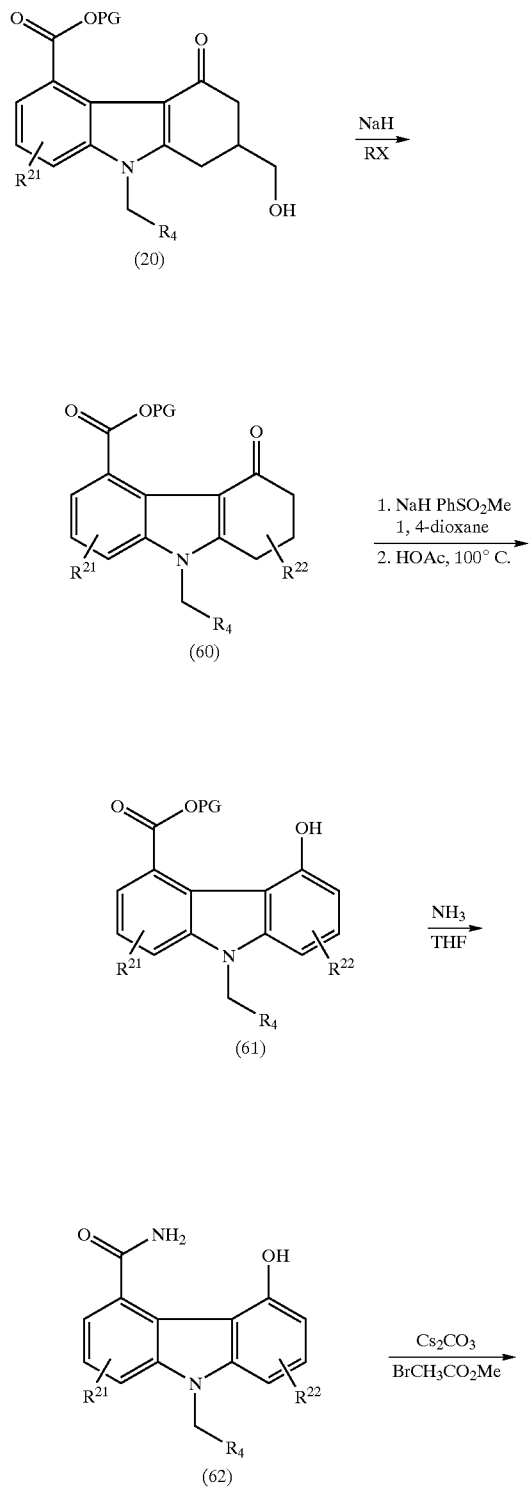

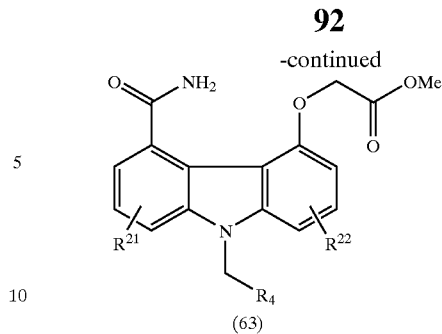

PG is an acid protecting group;

$R^{22}$ is $(C_1-C_6)$alkoxy $(C_1-C_6)$alkyl is $(C1-C_6)$alkoxy $(C_1-C_6)$alkenyl Starting material (20) is O-alkylated with an alkyl halide or alkenyl halide, using a base such as NaH, in an aprotic polar solvent preferably anhydrous DMF, at ambient temperature under a nitrogen atmosphere. The process of aromatization from a cyclohexenone functionality to a phenol functionality can be performed by treating the tetrahydrocabazole intermediate (60) with a base such as NaH in the presence of methyl benzenesulfinate in an anhydrous solvent, such as 1,4-dioxane or DMF, to form the ketosulfoxide derivative. Upon heating at about 100° C. for 1–2 hours, the ketosulfoxide derivative (60) is converted to the phenol derivative (61). Conversion of the ester (61) to the amide (62) can be achieved by treating a solution of (61) in an aprotic polar solvent such as tetrahydrofuran with ammonia gas. Phenolic O-alkylation of (62) with, for example, methyl bromoacetate can be carried out in anhydrous DMF at ambient temperature using $Cs_2CO_3$ or $K_2CO_3$ as a base to form (63). Desired product (64) can be derived from the basic hydrolysis of ester (63) using LiOH or NaOH as a base in an $H_2O/CH_3OH/THF$ solution at 50° C. for 1–2 hours.

When $R^{22}$ is —$(C_1-C_6)$alkoxy$(C_1-C_6)$alkenyl, hydrogenation of the double bond can be performed by treating (63) in THF using $PtO_2$ as a catalysis under a hydrogen atmosphere. Desired product can then be derived as described above in Scheme III(g) from the basic hydrolysis of ester (63) using LiOH or NaOH as a base in an $H_2O/CH_3OH/THF$ solution at 50° C. for 1–2 hours.

Compounds of formula Ie where the A ring is phenyl and the heteroatom in Z is sulfur, oxygen or nitrogen can be prepared as described in Schemes IV(a)–(f), below.

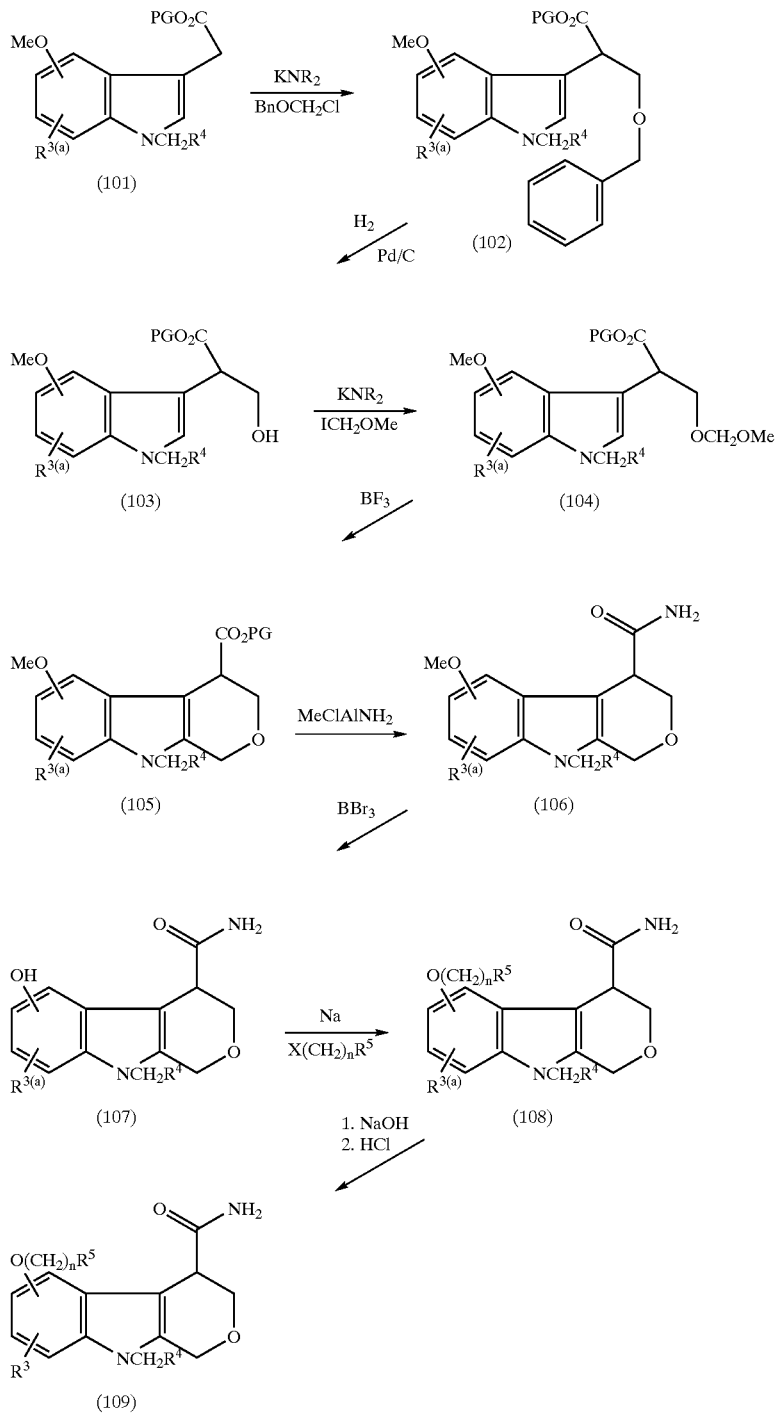

Scheme Ivg(a)

PG is an acid protecting group.
X is halo.
R³(a) is H, —O(C₁–C₄)alkyl, halo, —(C₁–C₆)alkyl, phenyl, —(C₁–C₄)alkylphenyl; phenyl substituted with —(C₁–C₆)alkyl, halo or —CF³; —CH₂OSi(C₁–C₆)alkyl, furyl, thiophenyl, —(C₁–C₆)hydroxyalkyl; or —(CH₂)ₙR⁸ where R⁸ is H, —NR⁹R¹⁰, —CN or phenyl where R⁹ and R¹⁰ are independently —(C₁–C₄)alkyl or -phenyl(C₁–C₄)alkyl and n is 1 to 8;

An indole-3-acetic ester (101), Ref 10, is alkylated by treatment with alkalai metal amide and benzyloxymethyl chloride to give (102) which is converted to the alcohol (103) by catalytic hydrogenation. The alcohol is alkylated to provide the formaldehyde acetal (104) which is cyclized by Lewis acid to produce the pyrano[3,4-b]indole (105). The ester is converted to the amide (106) by methylchloroaluminum amide, and then to the phenol (107) with boron tribromide. The phenol is O-alkylated to give (108) which is hydrolyzed to the acid (109).

10) Dillard, R. et al., J, Med Chem. Vol 39, No. 26, 5119–5136.

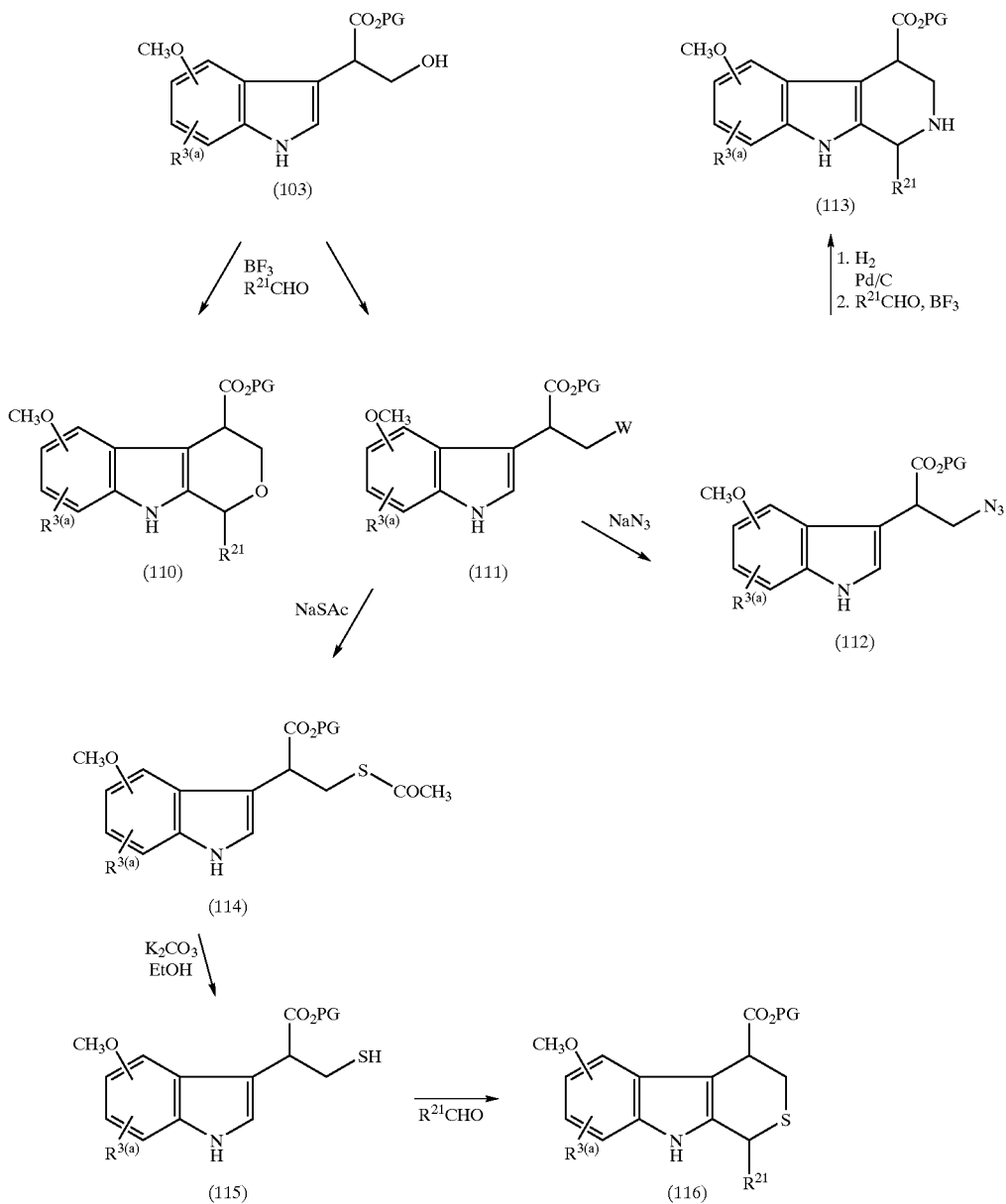

Scheme IVg(b)

PG is an acid protecting group
W is halo, alkyl or aryl sulfonyl
$R^3$(a) is H, —O($C_1$-$C_4$)alkyl, halo, —($C_1$-$C_6$)alkyl, phenyl, —($C_1$-$C_4$)alkylphenyl; phenyl substituted with —($C_1$-$C_6$)alkyl, halo or —$CF^3$; —$CH_2OSi$($C_1$-$C_6$) alkyl, furyl, thiophenyl, —($C_1$-$C_6$)hydroxyalkyl; or —($CH_2$)$_n R^8$ where $R^8$ is H, —$NR^9R^{10}$, —CN or phenyl where $R^9$ and $R^{10}$ are independently —($C_1$-$C_4$) alkyl or -phenyl($C_1$-$C_4$)alkyl and n is 1 to 8;

Reaction of this alcohol (103) with aldehyde and acid produces the pyranoindole (110).

Conversion of the hydroxyl function of (103) to a halide or sulfate functionality is achieved by treatment with triphenylphosphine and $CH_3X$ (where X is a halogen) to make compounds of formula (111) where X is a halide; or by treatment with triethylamine and methanesulfonyl chloride to make the sulfonate. Displacement with the sodium salt of thiol acetic acid gives (114) which in turn is hydrolyzed by base to the thiol (115) which is reacted with an appropriately substituted aldehyde and acid to produce the thiopyranoindoles (116).

Intermediate (111) may also be reacted with sodium azide to give the azido derivative (112) which is reduced by hydrogen catalytically to give the amine which is converted to the carboline (113) with aldehyde and acid.

Intermediates (113), (110) and (116) may be N-alkylated, using sodium hydride and an appropriately substituted alkylhalide $XCH_2R^4$.

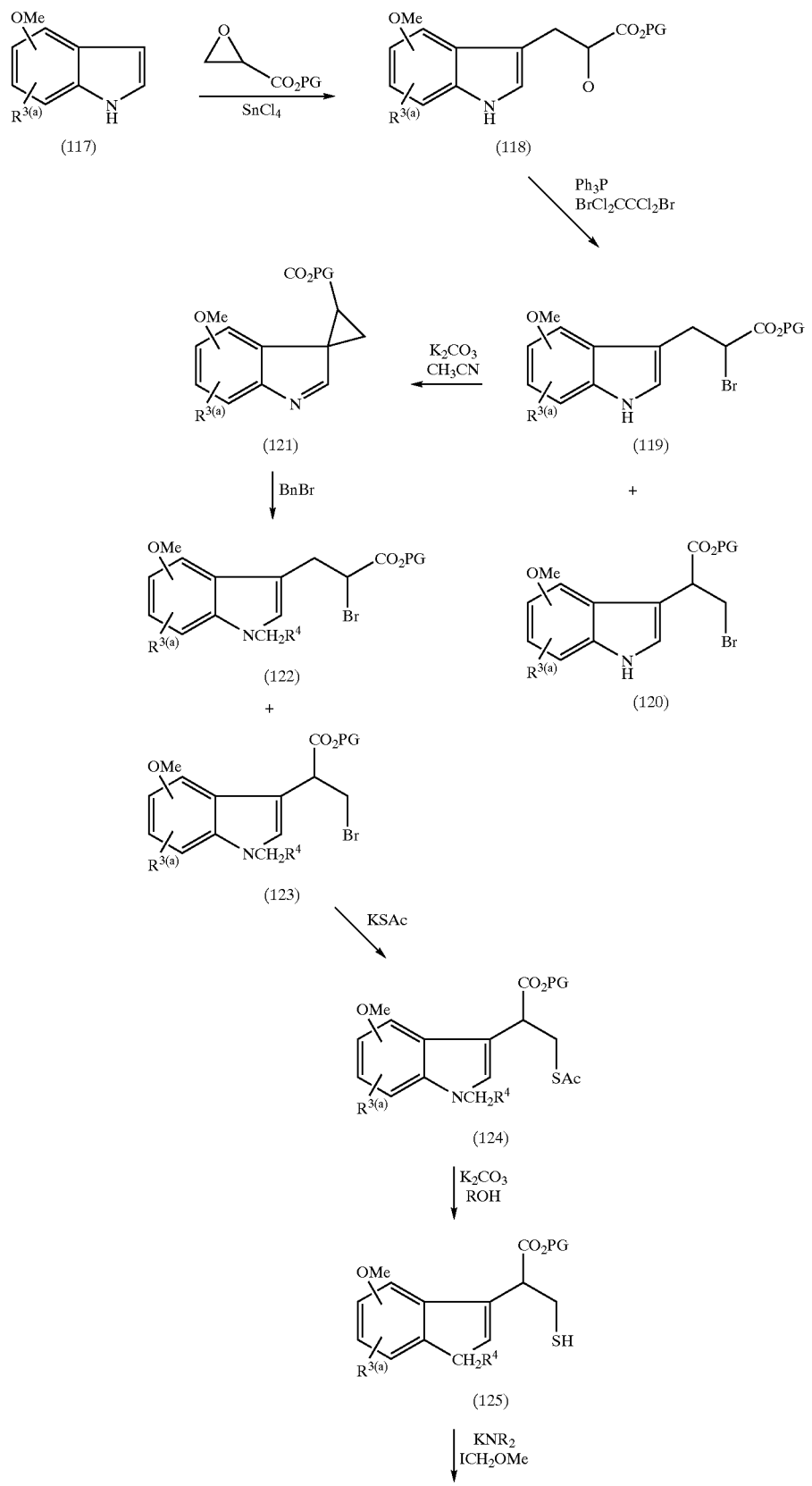

-continued

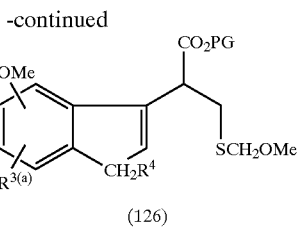
(126)

↓ ZnX₂

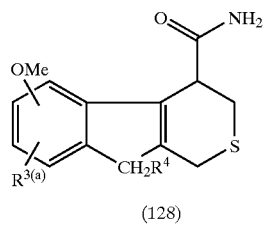
(128)

←── MeClAlNH₂ ──

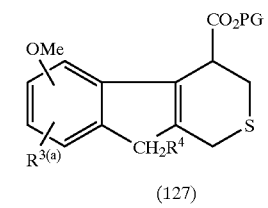
(127)

↓ BBr₃

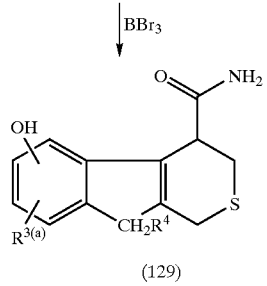
(129)

── NaH / Br(CH₂)ₙCO₂Et ──→

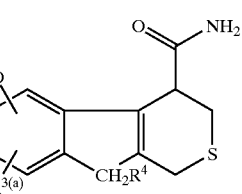
(130)

↙ 1. NaOH  2. HCl

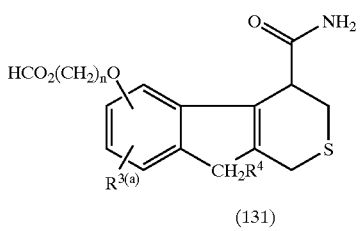
(131)

PG is an acid protecting group

R^{3(a)} is as defined above

4-Methoxyindole (117) is converted to the indole acetic acid derivative (118) by alkylation with an epoxy propionate. Treatment of (118) with a brominating reagent affords the mixture of bromo isomers (119) and (120) which give the Spiro compound (121) upon basic treatment. Heating (121) with benzyl bromide provides a mixture of the isomeric bromo compounds (122) and (123) which react with potassium thioacetate to give a mixture of isomers from which (124) may be separated. Solvolysis of the thioester produces the thiol (125) which is alkylated to give (126). Lewis acids convert (126) to the thiopyrano[3,4-b]indole (127). The ester function is converted to amide using methylchloroaluminum amide, the methyl ether cleaved by boron tribromide, and the product phenol O-alkylated with bromoacetic ester to give (130) which is hydrolyzed to (131).

Scheme IVg(d)

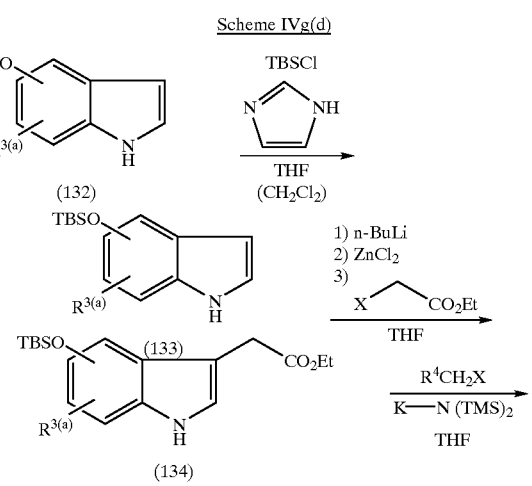

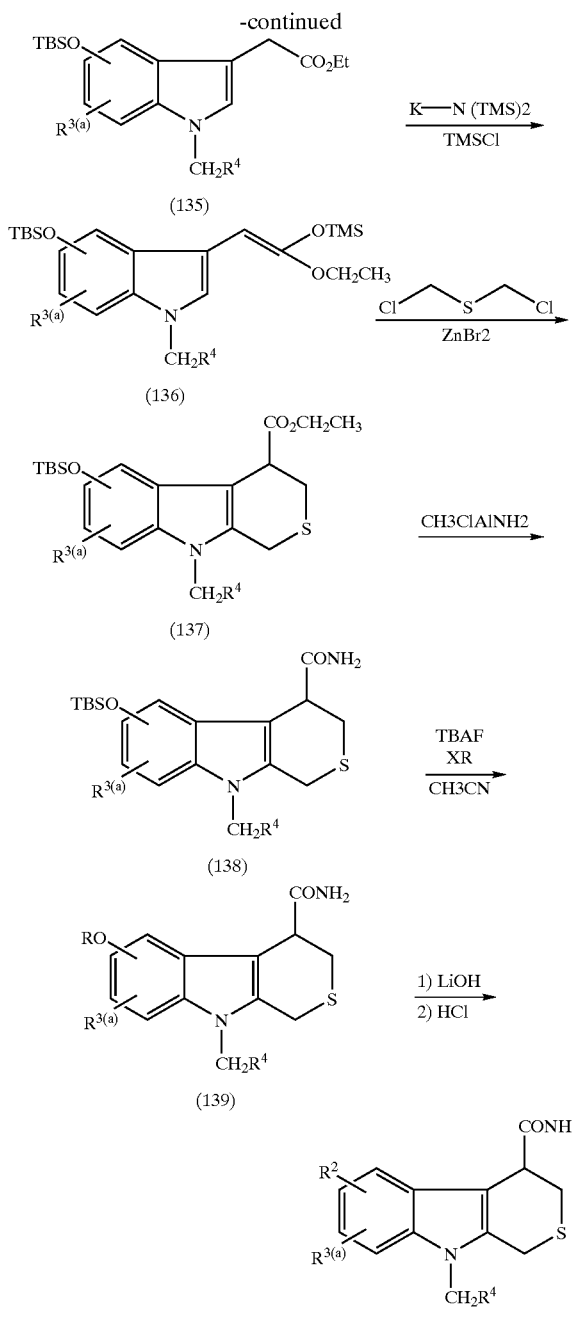
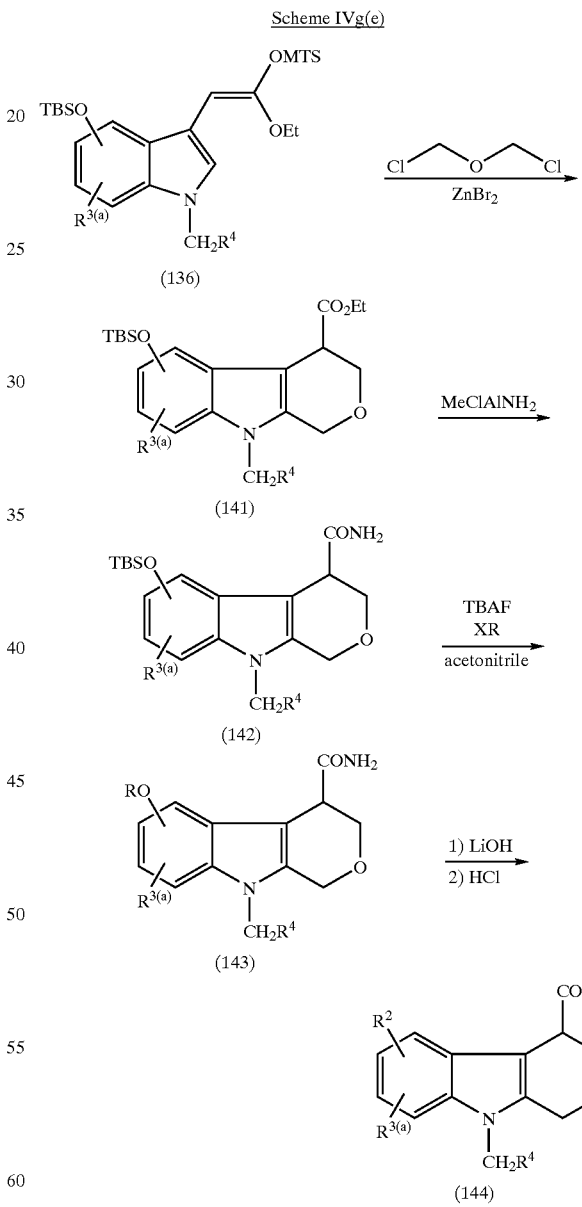

Alkylation of the indole-nitrogen can then be achieved by reacting (134) with a suitable alkyl halide in the presence of potassium bis(trimethylsilyl)amide to prepare (135).

The ester functionality of (135) is converted to a trimethylsilylketene acetal (136) by treatment with potassium bis (trimethylsilyl)amide and trimethylsilyl chloride. Treatment of the ketene acetal (136) with bis(chloromethyl)sulfide and zinc bromide in methylene chloride affords the cyclized product (137). Conversion to amide (138) can be accomplished by a Weinreb reaction with methylchloroaluminum amide. Removal of the oxygen protecting group with a fluoride source, such as tetrabutylammonium fluoride (TBAF), and concommitant reaction of the resulting anion with, for example, ethyl bromoacetate yields the ester (139). Deprotection of the ester yields the desired acid (140).

X is halo,
$R^{3(a)}$ is as defined in Scheme I(a) above; and
R is —$(CH_2)_m R^5$.

Protection of the oxygen by treatment of (132) with tert-butyldimethylsilyl chloride and imidazole in an aprotic polar solvent such as tetrahydrofuran or methylene chloride accomplishes (133).

Alkylation at the 3-position of the indole (133) is achieved by treatment with n-butyllithium then zinc chloride at temperatures starting at about 10° C. and warming to room temperature, followed by reaction with an appropriate haloalkyl ester such as methyl or ethyl bromoacetate. The reaction is preferably conducted at room temperature in an appropriate aprotic polar solvent such as tetrahydrofuran.

$R^{3(a)}$ is as described in Scheme I(a) and R is as described in Scheme IV(d).

Treatment of the ketene acetal (136) with bis (chloromethyl)ether and zinc bromide in methylene chloride affords the cyclized product (141). Conversion to amide (142) can be accomplished by a Weinreb reaction with methylchloroaluminum amide. Removal of the oxygen protecting group with a fluoride source, such as tetrabutylammonium fluoride, and concommitant reaction of the resulting anion with ethyl bromoacetate yields the ester (143). Deprotection of the ester yields the desired acid (144).
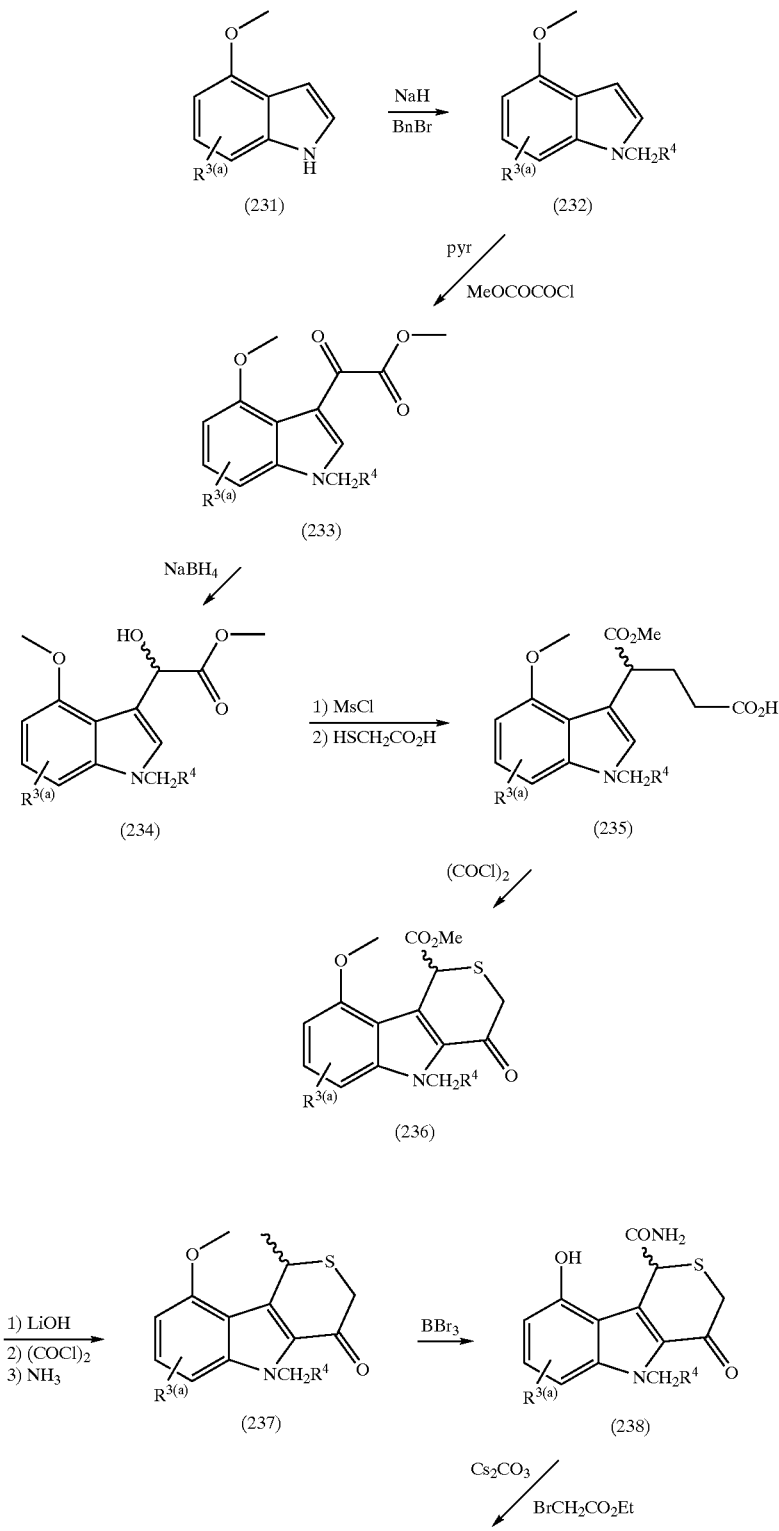
Scheme IVg(f)

-continued

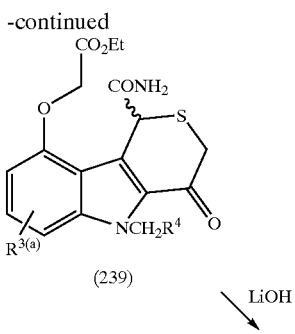
(239)

LiOH

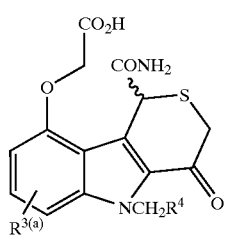

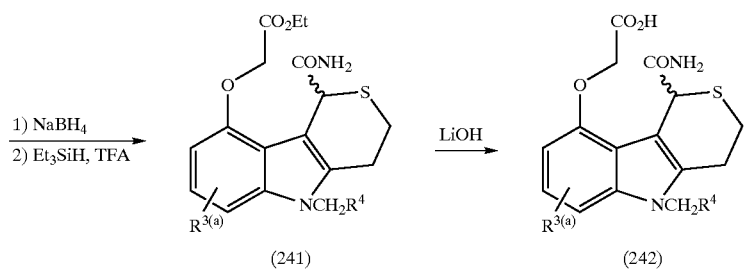

N-alkylation of commercially available 4-methoxy indole (231) under basic conditions using an alkyl halide affords the N-alkyl indole (232). Acylation with a suitable acid chloride provides the glyoxalate ester product (233) which can be reduced with a variety of hydride reducing agents to give intermediate alcohols (234). Conversion of the alcohol to a suitable leaving group and displacement with sulfur nucleophiles affords the thioether product (235). Conversion to the acid chloride and spontaneous cyclization affords the thioketone product (236). Cleavage of the ester can be effected under basic conditions to give the correponding acid which upon formation of the acid chloride and reaction with an appropriate amine gives the amide product (237). Cleavage of the methyl ether gives the phenol (238) which can be alkylated under basic conditions using alkyl halides to give the O-alkylated product (239). Cleavage of the ester under basic conditions gives the desired product (240). Alternatively, reduction of the benzylic ketone with a hydride reducing agent and subsequent deoxygenation of the resulting alcohol gives the deoxygenated product (244). Cleavage of the oxyacetic ester proceeds under basic conditions to give the desired oxyacetic acid (242).

Compounds where Z is an aromatic or heterocyclic ring containing nitrogen can be prepared as described in Schemes Vg(a)–(e), below.

Scheme Vg(a)

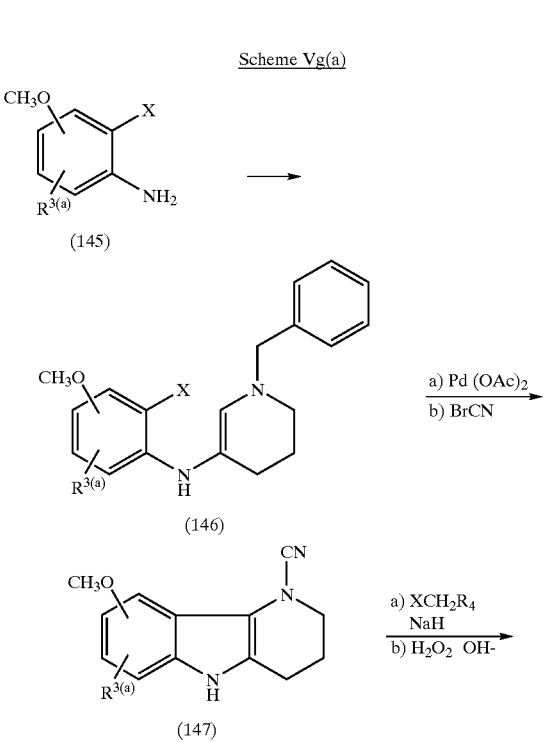

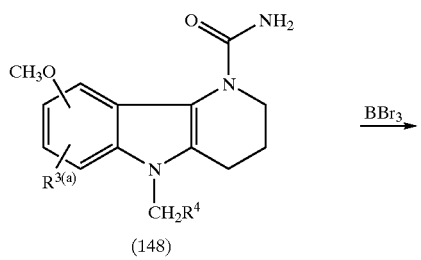

(148)

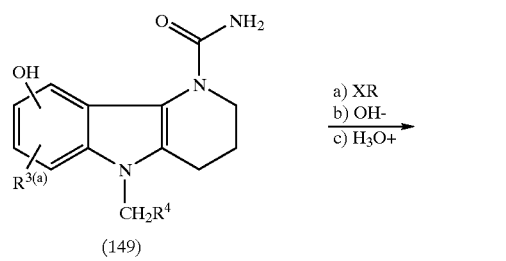

(149)

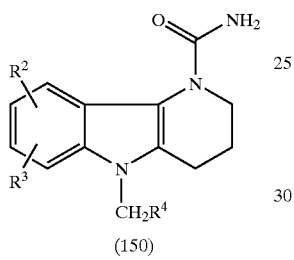

(150)

Substituted haloaniline (145) is condensed with N-benzyl-3-piperidone to provide enamine (146). Ring closure is effected by treatment of (146) with palladium (II) acetate and the resultant product is converted to (147) by treatment with cyanogen bromide. Alkylation of (147) is accomplished by treatment with the appropriate alkyl bromide using sodium hydride as base. Hydrolysis of this N-alkylated product with basic hydrogen peroxide under standard conditions provides (148). Demethylation of (148) is carried out by treatment with boron tribromide in methylene chloride. The resulting phenol (149) is converted by the standard sequence of O-alkylation with methyl bromoacetate in the presence of a base, hydrolysis with hydroxide to provide the intermediate salt which is then protonated in aqueous acid to provide desired δ-carboline (150).

Scheme Vg(b)

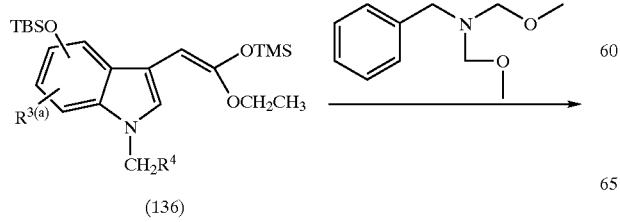

(136)

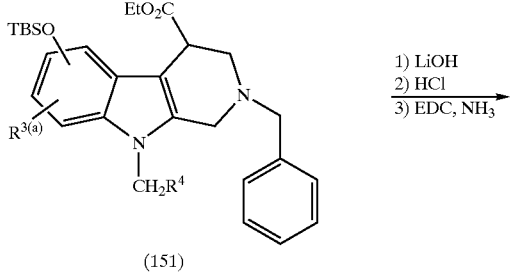

(151)

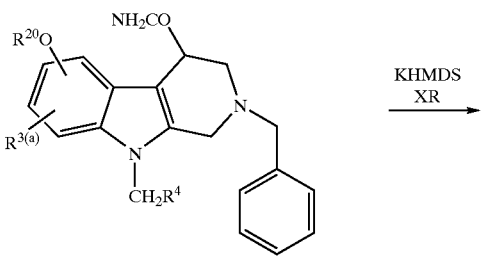

(152)

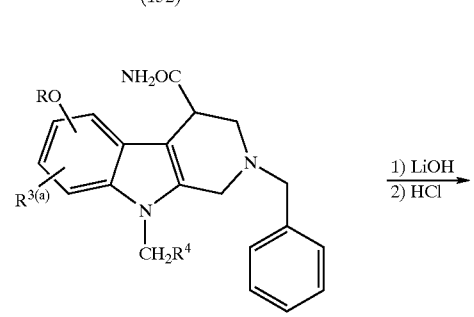

(153)

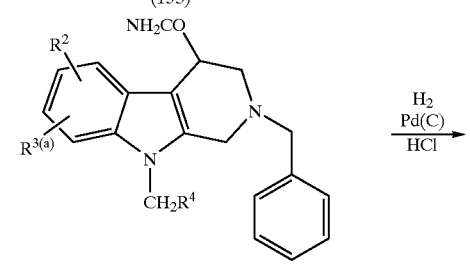

(154)

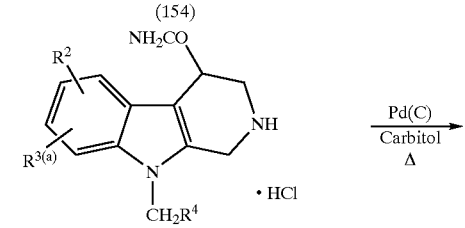

(155)

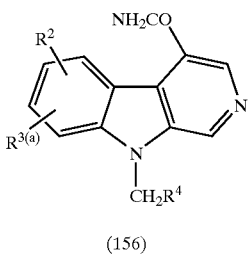

(156)

X is halo,

R is as defined in Scheme IV(d), and $R^{3(a)}$ is as defined in Scheme I(a).

Ketene acetal (136), prepared as described in Scheme IV(d), is reacted with benzyl bis(methoxymethyl)amine in the presence of zinc chloride to give the tetrahydro-beta-carboline (151).

Treatment of (151) with lithium hydroxide, neutralization with hydrochloric acid and subsequent treatment with 1-(3-dimethylaminopropyl)-3-ethylcarbodiimide hydrochloride and ammonia provides the desilyated amide (152) where $R^{20}$ is hydrogen, which can be alkylated with, for example, ethylbromoacetate to give ester (153).

Alternatively, treatment of (115) with the appropriate Weinreb reagent provides amide (152) ($R^{20}$ is t-butyldimethylsilyl) which is desilylated with tetra-n-butylammonium fluoride and alkylated with, for example, ethyl bromoacetate to give ester (153). Lithium hydroxide-mediated hydrolysis gives acid (154), which may be hydrogenated over an appropriate catalyst in the presence of hydrochloride acid to give the tetrahydro-beta-carboline as the hydrochloride salt(155). Compound (155) may in turn be aromatized by refluxing in carbitol with palladium on carbon to provide beta-carboline (156).

Scheme Vg(c)

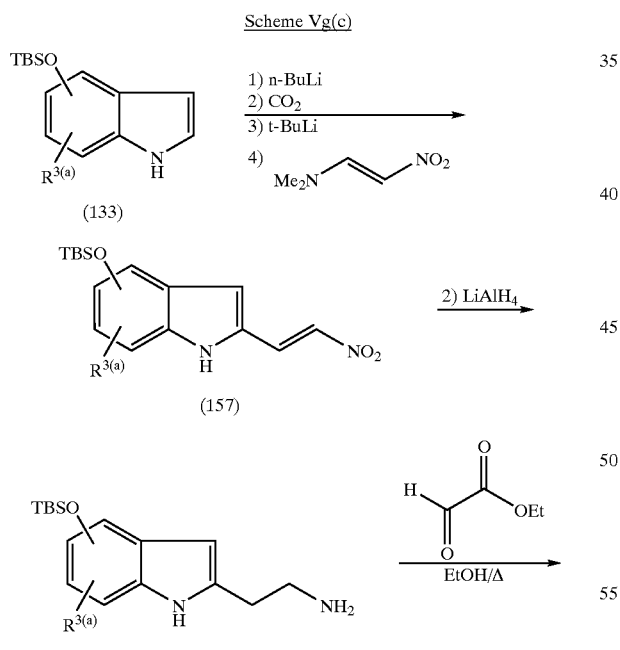

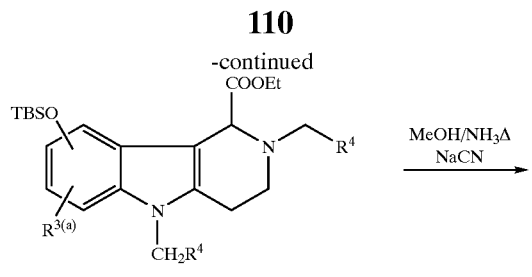

(160)

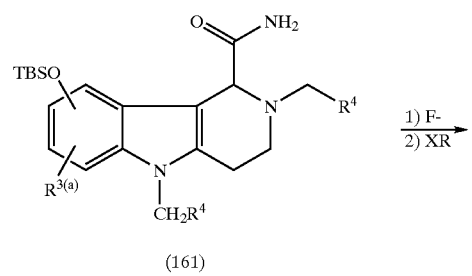

(161)

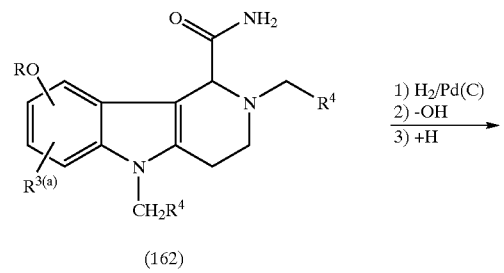

(162)

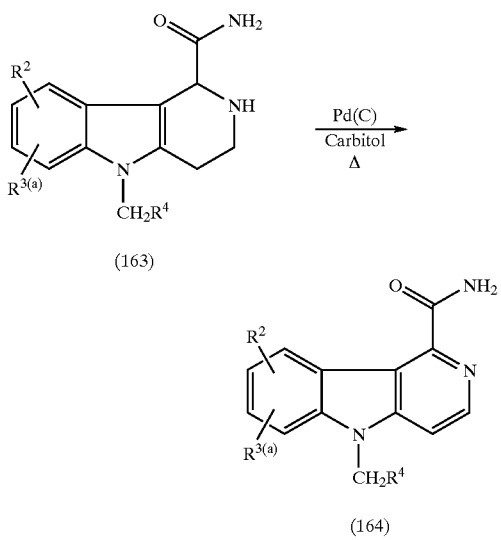

X is halo,
R is as defined in Scheme IV(d); and
$R^{3(a)}$ is as defined in Scheme I(a).

In a one-pot reaction, indole (133) is successively treated with one equivalent n-butyllithium, carbon dioxide gas, one equivalent of t-butyllithium, and 1-dimethylamino-2-nitroethene to give (157). Nitroalkene (157) is reduced with lithium aluminum hydride to amine (158), which is cyclized with methyl glyoxylate (Ref. 9) in refluxing ethanol to give tetrahydrocarboline (159). Alkylation of both nitrogens of (159) leads to intermediate (160), which is treated with the appropriate Weinreb reagent to provide amide (161). Fluoride-assisted desilylation and alkylation with, for example, ethyl iodoacetate gives ester (162), which may be hydrogenated over a suitable catalyst and base-hydrolyzed to give acid (163). Aromatization of (163) to carboline (164) is achieved by refluxing in carbitol in the presence of palladium-on-carbon.

Reference 9

Kelley, T. R.; Schmidt, T. E.; Haggerty, J. G. A convenient preparation of methyl and ethyl glyoxylate, Synthesis, 1972, 544–5.

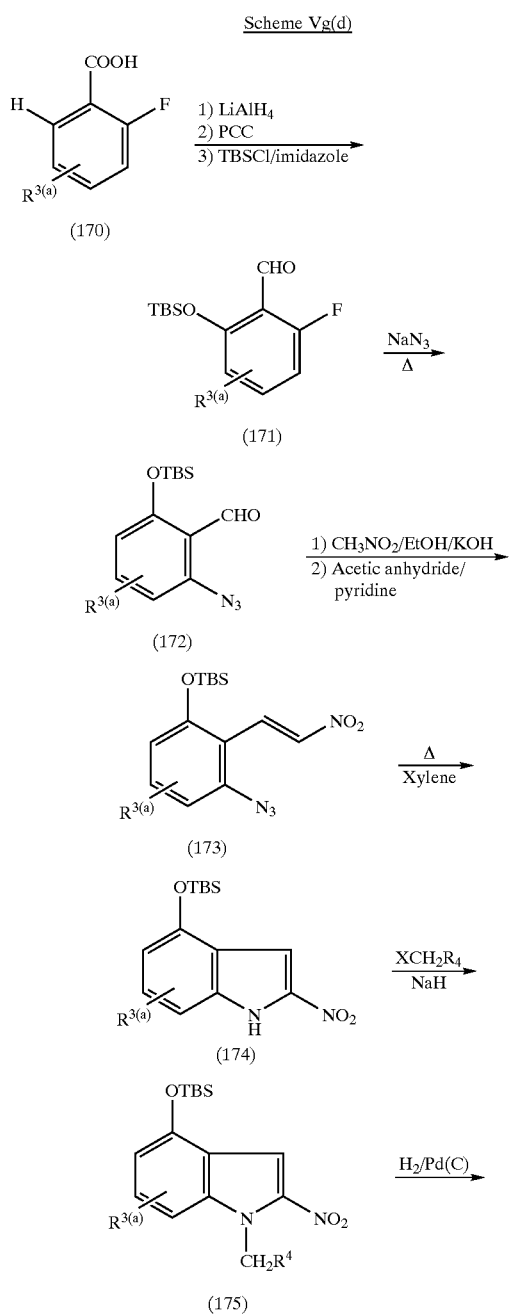

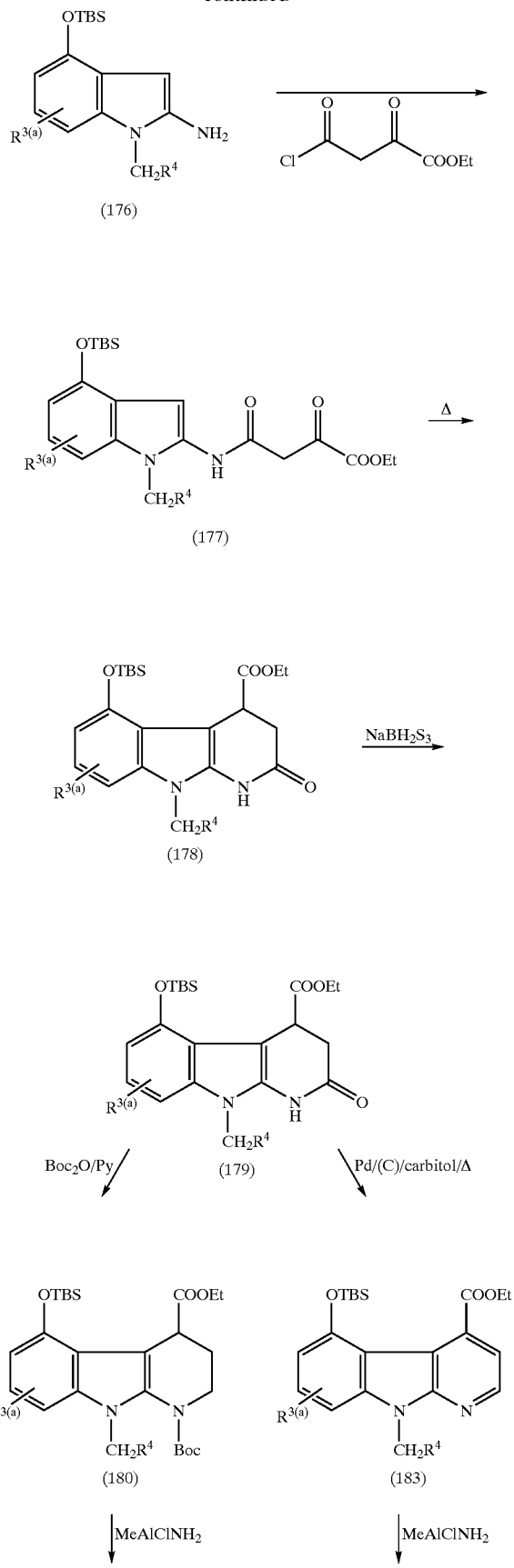

113

-continued

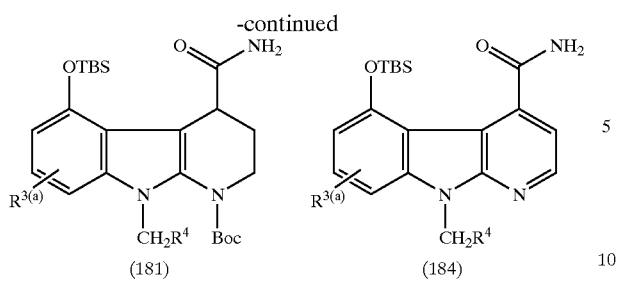

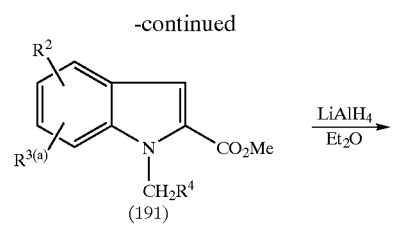

The commercially available acid (170) is reduced with lithium aluminum hydride, oxidized with pyridinium chlorochromate, and silylated with t-butyldimethylsilyl chloride to give (171). Treatment with sodium azide provides azide (172), which is reacted with nitromethane and potassium hydroxide in ethanol, followed by treatment with acetic anhydride and pyridine to give nitroolefin (173). Heating in xylene induces cyclization to produce indole (174). Alkylation with, for example, benzyl iodide and sodium hydride gives (175), which is hydrogenated in the presence of palladium-on-carbon to give amine (176). Acylation with the acid chloride of commercially available oxalacetic acid monoethyl ester gives (177), which is thermally cyclized to lactam (178). Selective reduction of the lactam carbonyl may be accomplished by treatment with NaBH$_2$S$_3$ to provide amine (179).

Protection of amine (179) with di-t-butyl dicarbonate and pyridine produces (180), which is converted via the appropriate Weinreb reagent to amide (181). Fluoride-assisted desilylation, alkylation with, for example, ethyl iodoacetate and potassium carbonate, base hydrolysis, and acid hydrolysis produce the tetrahydro-alpha-carboline (182).

Alternatively, amine (179) may be aromatized by refluxing in carbitol or some other suitable high boiling solvent to give alpha-carboline (183), which is converted via the appropriate Weinreb reagent to amide (184). Fluoride-assisted desilylation, alkylation with ethyl iodoacetate and potassium carbonate, and base hydrolysis as described above provides alpha-carboline (185).

Scheme Vg(e)

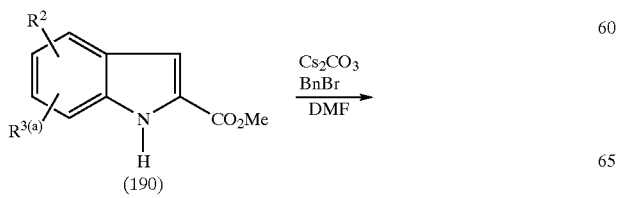

114

-continued

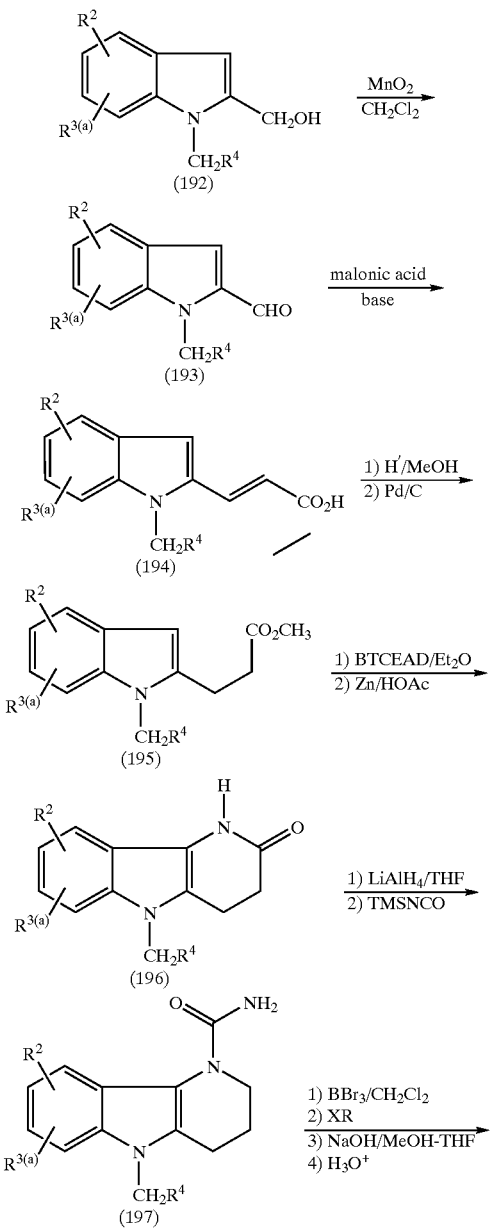

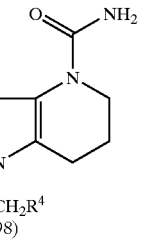

X is halo

R$^{3(a)}$ is as defined above Scheme V(e) provides δ-carboline (198) by the indicated sequence of reactions. N-alkylation of 2-carboethoxyindole (190) followed by a standard two carbon homologation sequence provides 2-(3-propenoic acid)indoles (194). In this sequence, the condensation of aldehyde (193) with malonic acid utilized a mixture of pyridine and piperidine as the base. After methyl ester formation and hydrogenation (195), ring closure (196) was effected by treatment with bis(2,2,2-trichloroethyl) azodicarboxylate (BTCEAD) followed by zinc in acetic acid. Reduction of the cyclic amide with lithium aluminum hydride followed by treatment with trimethylsilylisocyanate provided the urea (197). Conversion to the desired d-carboline (198) was accomplished under the usual conditions of demethylation and subsequent alkylation and ester hydrolysis steps.

Reverse indoles, i.e., compounds where B is carbon and D is nitrogen can be prepared as described in Scheme VIg, below.

Scheme VIg

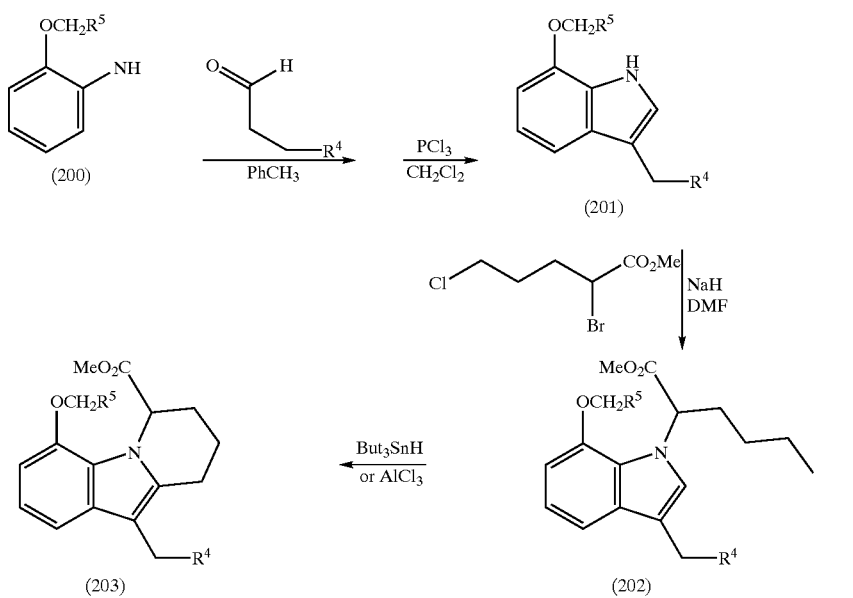

Aryl hydrazines (200) are condensed with substituted prpionaldehydes to form hydrazones which are cyclized to indoles (201) by treatment with phosphorous trichloride at room temperature (Ref 1). The indoles are N-alkylated on reaction with a base such as sodium hydride and an alph-bromo ester to give indoles (202) which are cyclized to tetrahydrocarbazoles (203) by Lewis acids (e.g., aluminum chloride) or by radical initiators (e.g., tributyltin hydride). Compounds (203) can be converted to carbazoles by, for example, refluxing in a solvent such as carbitol in the presence of Pd/C.

Compounds of formula I wherein A is pyridyl can be prepared as described in Schemes VIIg(a)–(b), below.

Scheme VIIg(a)

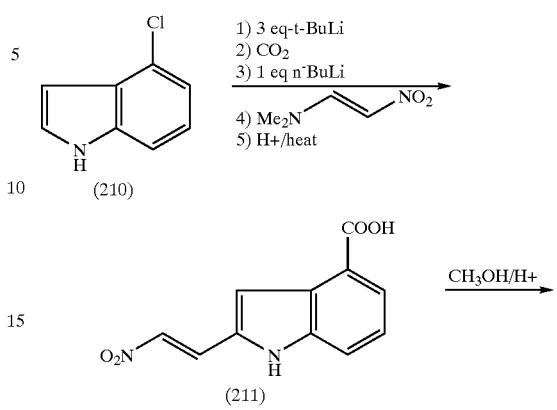

-continued

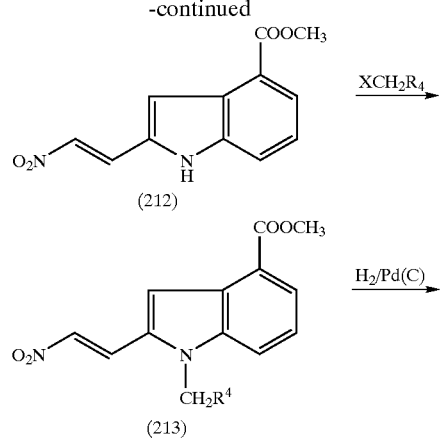

-continued

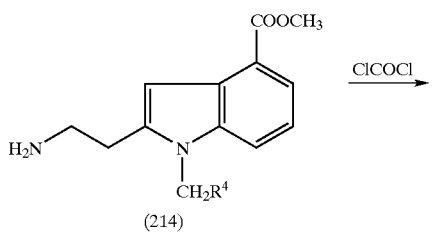
(214)

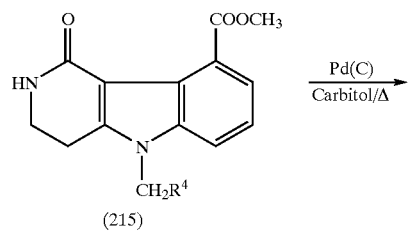
(215)

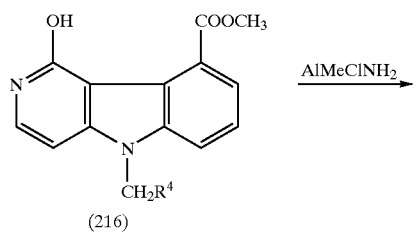
(216)

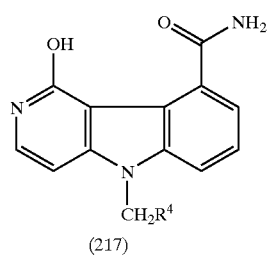
(217)

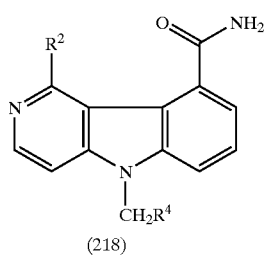
(218)

X is halo and

R is $(CH_2)_m R^5$.

Commercially available 4-chloroindole (210) is treated with 3 equivalents of t-butyllithium followed by carbon dioxide, 1 equivalent of n-butyllithium, 1-dimethylamino-2-nitroethene, and acid to provide carboxylic acid (211), which may be esterified to give (212). Alkylation at the 1-position followed by hydrogenation provides aminoethyl indole (214). Cyclization with phosgene to (215) followed by aromatization gives carboline (216). Treatment of (216) with the appropriate Weinreb reagent provides amide (217), which may be alkylated with, for example, ethyl bromoacetate and saponified with sodium hydroxide to give the carboline (218).

Scheme VIIg(b)

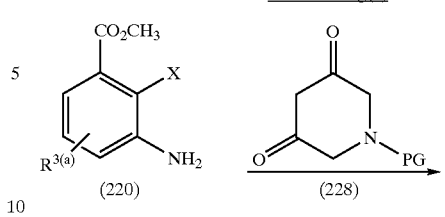
(220)   (228)

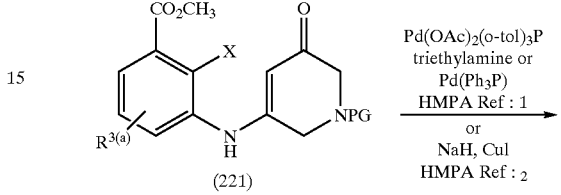
(221)

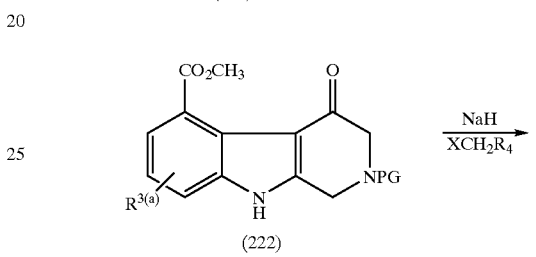
(222)

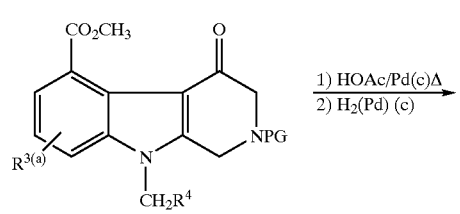
(223)

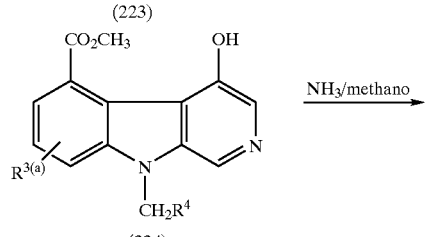
(224)

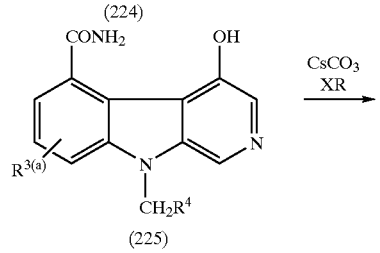
(225)

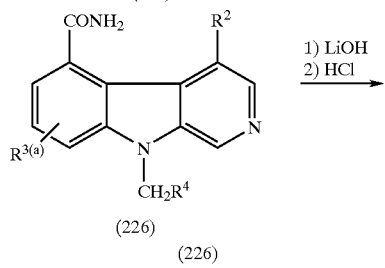
(226)

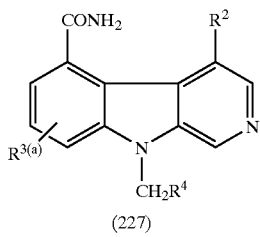

R3(a) is defined in Scheme I(a)
X is halo, and
R is $(CH_2)mR^5$.

The 1,3-dione structures (228) are either commercially available or readily prepared by known techniques from commercially available starting materials. Preparation of the aniline derivatives (220) (X=Cl, Br, or I) are accomplished by reducing an appropriately substituted benzoic acid derivative to the corresponding aniline by treatment with a reducing agent such as $SnCl_2$ in hydrochloric acid in an inert solvent such as ethanol or by hydrogenation using hydrogen gas and sulfided platinum or carbon or palladium on carbon. The amino group of (228) is protected with an appropriate protecting group, such as the, carboethoxyl, benzyl, CBZ (benzyloxycarbonyl) or BOC (tert-butoxycarbonyl) protecting group, and the like.

The dione (228) and aniline derivative (220) are condensed according to the general procedure of Chen, et al., (Ref 10) or Yang, et al., (Ref 11), with or without a noninterfering solvent, such as methanol, toluene, or methylene chloride, with or without an acid, such as p-toluenesulfonic acid or trifluoroacetic acid, with or without N-chlorosuccinimide and dimethyl sulfide, to afford the coupled product (221).

Compound (221) is cyclized under basic conditions with a copper (I) salt in an inert solvent according to the general procedure of Yang, et al., (Ref†8). The derivative (221) is treated with a base, such as sodium hydride, in an inert solvent, such as HMPA, at a temperature between 0 and 25° C. A copper (I) salt, such as copper (I) iodide, is added and the resultant mixture stirred at a temperature between 25 and 150° C. for 1 to 48 hours to afford compound (222).

Compound (221) may also be cyclized according to the general procedure of Chen, et al., (Ref 10). The derivative (221) is treated with a base, such as sodium bicarbonate, and a palladium catalyst, such as $Pd(PPh_3)_4$, in an inert solvent, such as HMPA, at a temperature between 25 and 150° C. to afford compound (222).

In a preferred method, intermediate (171) is treated with a transition metal catalyst, such as $Pd(OAc)_2(O\text{-tol})_3P$ in the presence of a base such as triethylamine using a cosolvent of DMF/acetonitrile to prepare (222).

Compound (222) is N-alkylated with an appropriately substituted benzyl halide in the presence of a base, such as sodium hydride or potassium carbonate, in a noninterfering solvent, such as dimethylformamide or dimethylsulfoxide to afford ketone (223). In a two step, one pot process(222) is aromatized by treatment with acetic acid and palladium on carbon in a noninterfering solvent, such as carbitol or cymene, followed by treatment with hydrogen gas and palladium on carbon to cleave the nitrogen protecting group and produce the phenolic derivative (224).

The ester (224) is converted to the corresponding amide (225) under standard conditions with ammonia (preferably) or an ammonium salt, such as ammonium acetate, in an inert solvent, such as water or alcohol, preferably methanol, or with $MeClAlNH_2$ in an inert solvent, such as toluene, at a temperature between 0 to 110° C. Alkylation of the phenolic oxygen of compound 38 with an appropriate haloester, such as methyl bromoacetate, in the presence of a base, such as cesium carbonate, potassium or sodium carbonate, in an inert solvent, such as dimethylformamide or dimethylsulfoxide affords the ester-amide (226). Other haloesters, such as ethyl bromoacetate, propyl bromoacetate, butyl bromoacetate, and the like can also be used to prepare the corresponding esters.

Saponification of compound (226), with lithium hydroxide in an inert solvent, such as methanol-water, affords (227). The intermediate and final products may isolated and purified by conventional techniques such as chromatography or recrystallization. Regioisomeric products and intermediates can be separated by standard methods, such as, recrystallization or chromatography. References:

10) L.-C. Chen et al., Synthesis 385 (1995)
11) S.-C. Yang et al., Heterocycles, 32, 2399 (1991)
h) Pyrazole $sPLA_2$ inhibitors The method of the invention may be practiced using pyrazole $sPLA_2$ inhibitors, which are described (together with the method of making) in U.S. patent application Ser. No. 08/984,261, filed Dec. 3, 1997, the entire disclosure of which is incorporated herein by reference. Suitable pyrazole compounds are represented by formula (Ih)

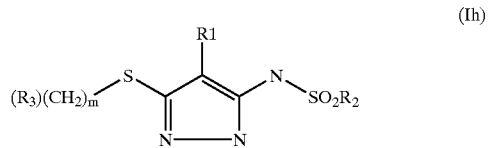

(Ih)

wherein:

$R^1$ is phenyl, isoquinolin-3-yl, pyrazinyl, pyridin-2-yl, pyridin-2-yl substituted at the 4-position with —$(C_1-C_4)$alkyl, $(C_1-C_4)$alkoxyl, —CN or —$(CH_2)_n$ $CONH_2$ where n is 0–2;

$R^2$ is phenyl; phenyl substituted with 1 to 3 substituents selected from the group consisting of —$(C_1-C_4)$alkyl, —CN, halo, —$NO_2$, $CO_2(C_1-C_4)$alkyl and —$CF_3$; naphthyl; thiophene or thiophene substituted with 1 to 3 halo groups;

$R^3$ is hydrogen; phenyl; phenyl$(C_2-C_6)$alkenyl; pyridyl; naphthyl; quinolinyl; $(C_1-C_4)$alkylthiazolyl; phenyl substituted with 1 to 2 substituents selected from the group consisting of —$(C_1-C_4)$alkyl, —CN, —$CONH_2$, —$NO_2$, —$CF_3$, halo, $(C_1-C_4)$alkoxy, $CO_2(C_1-C_4)$ alkyl, phenoxy and $SR^4$ where $R^4$ is —$(C_1-C_4)$alkyl or halophenyl;

phenyl substituted with one substituent selected from the group consisting of
—$O(CH_2)_pR^5$ where p is 1 to 3 and $R^5$ is —CN, —$CO_2H$, —$CONH_2$, or tetrazolyl, phenyl and —$OR^6$ where $R^6$ is cyclopentyl, cyclohexenyl, or phenyl substituted with halo or $(C_1-C_4)$alkoxy;

or phenyl substituted with two substituents which, when taken together with the phenyl ring to which they are attached form a methylenedioxy ring; and m is 1 to 5;

or a pharmaceutically acceptable salt thereof.

Particularly preferred are pyrazole type $sPLA_2$ inhibitors as follows:

A pyrazole compound of formula (I), supra, wherein:
  $R^1$ is pyridine-2-yl or pyridine-2-yl substituted at the 4-position with —$(C_1-C_4)$alkyl, $(C_1-C_4)$alkoxy, —CN or —$(CH_2)_n CONH_2$ where n is 0–2;
  $R^2$ is phenyl substituted with 1 to 3 substituents selected from the group consisting of —$(C_1-C_4)$alkyl, —CN, halo, —$NO_2$, $CO_2(C_1-C_4)$alkyl and —$CF_3$; and
  $R^3$ is phenyl; phenyl($C_2-C_6$)alkenyl; phenyl substituted with 1 or 2 substituents selected from the group consisting of —$(C_1-C_4)$alkyl, —CN, —$CONH_2$, —$NO_2$, —$CF_3$, halo, $(C_1-C_4)$alkoxy, $CO_2(C_1-C_4)$alkyl, phenoxy and $SR^4$ where $R^4$ is —$(C_1-C_4)$alkyl or halo phenyl;
  phenyl substituted with one substituent selected from the group consisting of —$O(CH_2)pR^5$ where p is 1 to 3 and $R^5$ is —CN, —$CO_2H$, —$CONH_2$ or tetrazolyl, phenyl and —$OR^6$ where $R^6$ is cyclopentyl, cyclohexenyl or phenyl substituted with halo or $(C_1-C_4)$alkoxy;
or phenyl substituted with two substituents which when taken together with the phenyl ring to which they are attached form a methylenedioxy ring.

Specific suitable pyrazole type sPLA$_2$ inhibitors useful in the method of the invention are as follows:

Compounds selected from the group consisting of 3-(2-chloro-6-methylphenylsulfonylamino)-4-(2-(4-acetamido)pyridyl)-5-(3-(4-fluorophenoxy)benzylthio)-(1H)-pyrazole and 3-(2,6-dichlorophenylsulfonylamino)-4-(2-(4-acetamido)pyridyl)-5-(3-(4-fluorophenoxy)benzylthio)-(1H)-pyrazole.

The pyrazole compounds of formula Ih are prepared as described in Scheme Ih below.

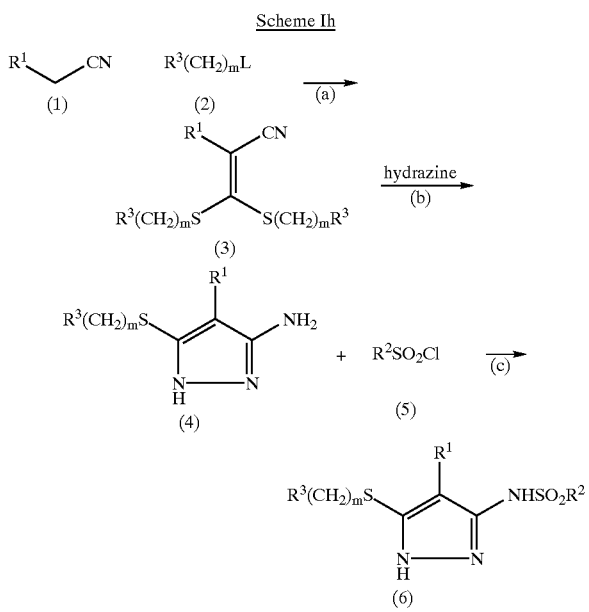

L is a leaving group.

In an aprotic polar solvent, such as tetrahydrofuran, an acetonitrile compound (1) is deprotonated by treatment with an excess of a strong base, such as sodium hydride, preferably under an inert gas, such as nitrogen. The deprotonated intermediate is treated with carbon disulfide and then alkylated twice with an appropriately substituted alkyl halide (2) of the formula $R^3(CH_2)_m L$, where L is a leaving group, preferably bromine, and $R^3$ and m are as defined above, to prepare intermediate compound (3). The reaction is conducted at ambient temperatures and is substantially complete in 1 to 24 hours.

Cyclization to form the amino substituted pyrazole (4) is achieved by reacting intermediate (3) with hydrazine at room temperature for from about 1 to 24 hours.

Selective sulfonylation of the amino group of intermediate (4) can be accomplished by treatment with a sulfonyl chloride (5) of the formula $R^2SO_2Cl$, where $R^2$ is as defined above, to prepare product (6). The reaction is preferably conducted in a solvent, such as pyridine, at ambient temperature for a period of time of from 1 to 24 hours. Preparation of 2,6-dimethylphenylsulfonyl chloride can be accomplished as described in *J. Org. Chem.* 25, 1996 (1960). All other sulfonyl chlorides are commercially available.

i) Phenyl glyoxamide sPLA$_2$ inhibitors (and the method of making them) are described in U.S. patent application Ser. No. 08/979,446, filed Nov. 24, 1997 (titled, Phenyl Glyoxamides as sPLA$_2$ Inhibitors), the entire disclosure of which is incorporated herein by reference.

The method of the invention is for treatment of a mammal, including a human, afflicted with cystic fibrosis, said method comprising administering to said human a therapeutically effective amount a phenyl glyoxamide type sPLA$_2$ inhibitors useful in the method of the invention are as follows:

A compound of the formula (Ii)

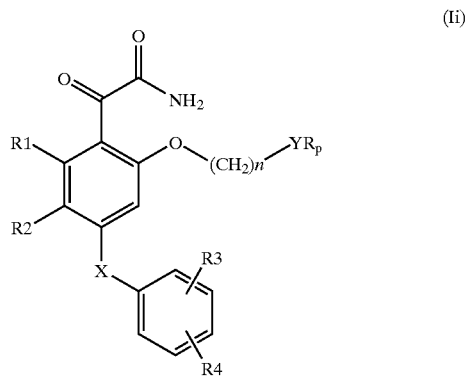

(Ii)

wherein:
  X is —O— or —$(CH_2)_m$—, where m is 0 or 1;
  Y is —$CO_2$—, —$PO_3$—, —$SO_3$—;
  R is independently —H or —$(C_1-C_4)$alkyl;
  $R^1$ and $R^2$ are each independently —H, halo or —$(C_1-C_4)$alkyl;
  $R^3$ and $R^4$ are each independently —H, —$(C_1-C_4)$alkyl, $(C_1-C_4)$alkoxy, $(C_1-C_4)$alkylthio, halo, phenyl or phenyl substituted with halo;
  n is 1–8; and
  p is 1 when Y is —$CO_2$— or —$SO_3$— and 1 or 2 when Y is —$PO_3$—;

or a pharmaceutically acceptable salt thereof.

A specific suitable phenyl glyoxamide type sPLA$_2$ inhibitors is 2-(4-carboxybut-1-yl-oxy)-4-(3-phenylphenoxy)-phenylglyoxamide.

These phenyl glyoxylamide compounds useful in the method of the invention are prepared as follows:

Compounds where $R^1$, $R^2$, $R^3$ and $R^4$ are H, and X, Y and n and p are as defined above can be prepared according to the following Scheme Ii.

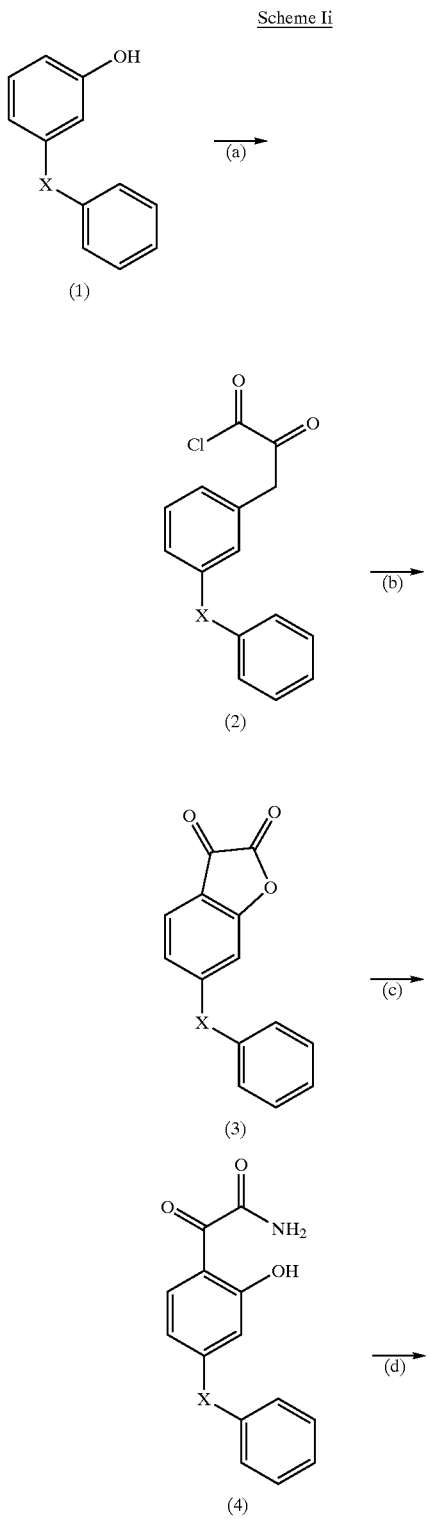

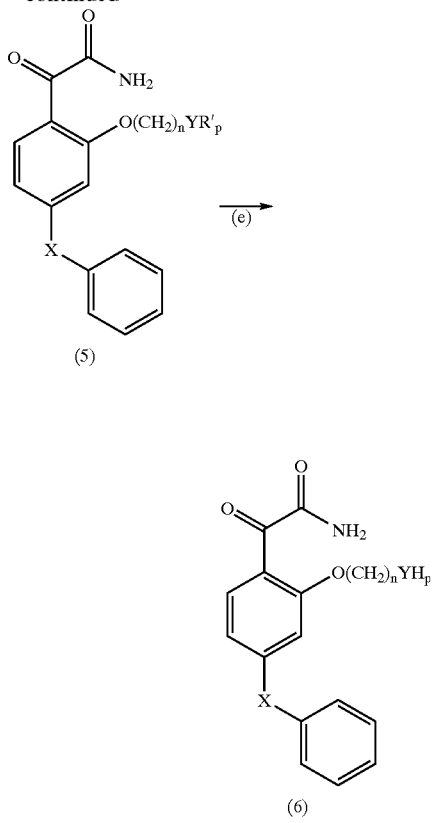

R' is —$(C_1$—$C_4)$ alkyl

Reflux of (1) with oxalyl chloride in an alkyl halide solvent, such as chloroform, using 4-N,N' dimethylamino pyridine as a catalyst achieves intermediate (2).

Under Friedel-Crafts conditions, using a suitable Lewis-acid catalyst such as aluminum chloride, compound (2) is internally cyclized to form compound (3). The reaction is preferably conducted at temperatures from about 0° C. to room temperature and allowed to proceed for about 24 hours.

Aminolysis of (3) to amide (4) can be achieved by treatment with concentrated ammonium hydroxide.

Alkylation of the hydroxyl of compound (4) can be readily achieved by treatment with an appropriate alkylating agent, such as $Br(CH_2)_nY$, where Y is —$CO_2R$, —$PO_3R^2$ or $SO_3R$ and R is —$(C_1$–$C_4)$alkyl, to form intermediate (5). The reaction is preferably conducted in an aprotic polar solvent, such as dimethyl formamide, in the presence of potassium carbonate and a suitable catalyst, such as potassium iodide.

Conversion of (5) to the carboxylic or sulfonic acid or acid salt (6) may be achieved by treatment with an appropriate base, such as aqueous sodium hydroxide, in a polar protic solvent, such as methanol.

When n is 2, a bromoacetal must be employed as an alkylating agent to achieve the carboxylic acid (6). The alkylated moiety (5) is then converted to the acid (6) by oxidizing with sodium dichromatate in aqueous conditions.

When Y is —$PO_3$—, conversion to the acid (6), is preferably conducted in an alkyl halide solvent, such as methylene chloride, using a dealkylating agent, such as trimethylsilyl bromide, and an excess of potassium carbonate, followed by treatment with methanol.

When $R^1$, $R^2$, $R^3$ or $R^4$ are other than hydrogen, the preparation proceeds as described in Scheme IIi on the following page.

Scheme IIi

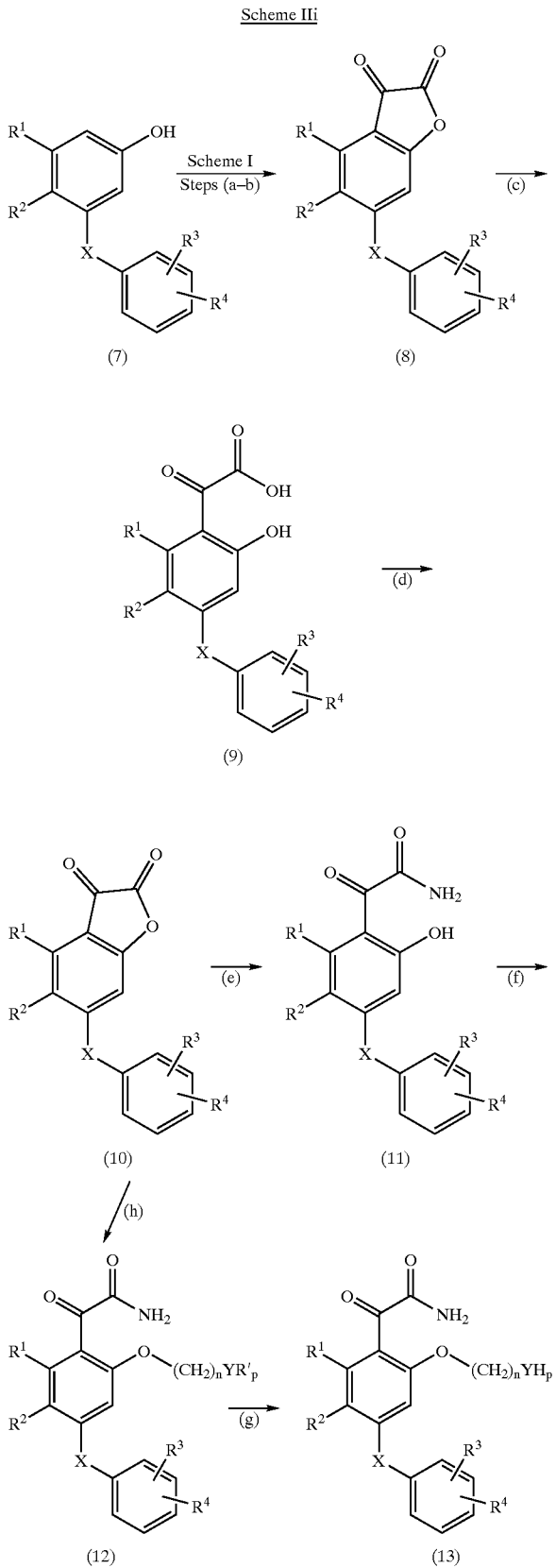

(7)　(8)

(9)

(10)　(11)

(12)　(13)

R' is as defined in Scheme Ii.

An appropriately $R^1$, $R^2$ substituted phenol (7) is converted to lactone (8) following the procedures described in Scheme Ii, steps (a–b) above.

Conversion to the intermediate (9) is accomplished by reacting (2a) with an aqueous acid, such as hydrochloric acid which affords removal of aluminum chloride from the reaction. Acid (9) is converted to the corresponding acid chloride using oxalyl chloride with dimethyl formamide as a catalyst. The acid chloride is recyclized to the lactone (10) on removal of the solvent, preferably under vacuum. The lactone (10) is converted to the glyoxamide (11) by treatment with an excess of ammonia as described in Scheme †I, step (c), above.

Alkylation of (11) to prepare the ester (12), followed by conversion to the acid is accomplished according to the procedure outlined in Scheme I, steps (d) and (e).

Alternately, conversion of (10) to (12) can be accomplished in a one-pot procedure by treating the lactone (10) with sodium amide in an aprotic polar solvent, such as dimethylformamide, preferably at temperatures of from about 0° C. to 20° C., followed by alkylation with an appropriate alkyl halide.

j) Pyrrole sPLA$_2$ inhibitors and methods of making them are disclosed in U.S. patent applicaton Ser. No. 08/985,518 filed Dec. 5, 1997 (titled, "Pyrroles as sPLA$_2$ Inhibitors"), the entire disclosure of which is incorporated herein by reference.

The method of the invention is for treatment of a mammal, including a human, afflicted with cystic fibrosis, said method comprising administering to said human a therapeutically effective amount a pyrrole sPLA$_2$ inhibitors useful in the method of the invention as follows:

A compound of the formula (Ij)

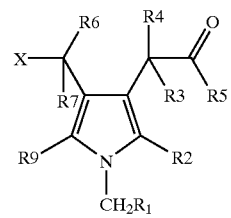

(Ij)

$R^1$ is hydrogen, $(C_1-C_4)$alkyl, phenyl or phenyl substituted with one or two substituents selected from the group consisting of —$(C_1-C_4)$alkyl, $(C_1-C_4)$alkoxy, phenyl$(C_1-C_4)$alkyl, $(C_1-C_4)$alkylthio, halo and phenyl;

$R^2$ is hydrogen, —$(C_1-C_4)$alkyl, halo, $(C_1-C_4)$alkoxy or $(C_1-C_4)$alkylthio;

$R^3$ and $R^4$ are each hydrogen or when taken together are =O;

$R^5$ is —$NH_2$ or —$NHNH_2$;

$R^6$ and $R^7$ are each hydrogen or when one of $R^6$ and $R^7$ is hydrogen, the other is —$(C_1-C_4)$alkyl, —$(CH_2)_nR^{10}$ where $R^{10}$ is —$CO_2R^{11}$, —$PO_3(R^{11})_2$, —$PO_4(R^{11})_2$ or —$SO_3R^{11}$ where $R^{11}$ is independently hydrogen or —$(C_1-C_4)$alkyl and n is 0 to 4; or $R^6$ and $R^7$, taken together, are =O or =S;

X is $R^8(C_1-C_6)$alkyl; $R^8(C_2-C_6)$alkenyl or phenyl substituted at the ortho position with $R^8$ where $R^8$ is $(CH_2)_nR^{10}$ where $R^{10}$ is —$CO_2R^{11}$, —$PO_3(R^{11})_2$, —$PO_4(R^{11})$ or —$SO_3R^{11}$, $R^{11}$ and n is 1 to 4 as defined above, and additionally substituted with one or two substituents selected from the group consisting of hydrogen, —(C₁–C₄)alkyl, halo, (C₁–C₄)alkoxy, or two substituents which, when taken together with the phenyl ring to which they are attached, form a naphthyl group; and R⁹ is hydrogen or methyl or ethyl;
or a pharmaceutically acceptable salt thereof.

Preferred pyrrole sPLA₂ inhibitors useful in the method of the invention are compounds of formula Ij wherein;

R¹ is phenyl;
R² is methyl or ethyl;
R⁵ is —NH₂;
R⁶ and R⁷ are each hydrogen;
X is R⁸(C₁–C₆)alkyl or phenyl substituted at the ortho position with R⁸ where
R⁸ is —CO₂R¹¹; and
R⁹ is methyl or ethyl.

A specific suitable pyrrole sPLA₂ inhibitors useful in the method of the invention is 2-[1-benzyl-2,5-dimethyl-4-(2-carboxyphenylmethyl)pyrrol-3-yl]glyoxamide.

The pyrrole compounds are prepared as follows:

Compounds of formula I where R⁵ is —NH₂ can be prepared as shown in Scheme Ij, below.

hydride reduction using, for example, sodium borohydride, the hydroxy intermediate (5) is prepared which can be further reduced using either catalytic or hydride reduction (preferably palladium on carbon) to prepare (6). Deprotection of R⁸ to the acid may be readily achieved by conventional techniques. For example, when an alkyl ester is used as a protecting group, deprotection can be accomplished by treatment with a base, such as sodium hydroxide.

k) Naphthyl glyoxamide sPLA₂ inhibitors and methods of making them are described in U.S. patent application Ser. No. 09/091,079, filed Dec. 9, 1966 (titled, "Naphthyl Glyoxamides as sPLA2 Inhibitors"), the entire disclosure of which is incorporated herein by reference.

The method of the invention is for treatment of a mammal, including a human, afflicted with cystic fibrosis, said method comprising administering to said human a therapeutically effective amount a naphthyl glyoxamide sPLA₂ inhibitors useful in the method of the invention are as follows:

A naphthyl glyoxamide compound or a pharmaceutically acceptable salt, solvate or prodrug derivative thereof; wherein said compound is represented by the formula Ik Scheme Ij

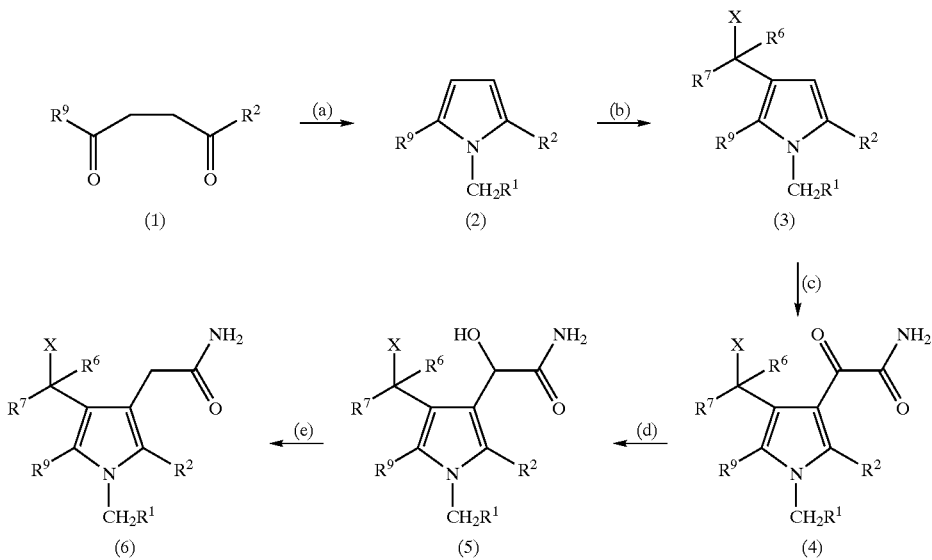

An appropriately substituted gamma-diketone (1) is reacted with an alkylamine of the formula NHCH₂R¹ to give pyrrole (2). Under Friedel-Crafts conditions, using a suitable Lewis-acid catalyst such as stannic chloride, aluminum chloride, or titanium tetrachloride (preferably stannic chloride) pyrrole (2) is ring alkylated with an alkyl or arylalkyl halide compound of the formula ZCR⁶R⁷X where Z is a suitable halogen and R⁸ of X is a protected acid or ester. The reaction is preferably conducted in a halogenated hydrocarbon solvent, such as dichloromethane, at ambient temperatures and allowed to proceed for from about 1 to about 24 hours.

Intermediate (3) is converted to (4) by sequential treatment with oxalyl chloride followed by ammonia. Selective reduction of (4) is accomplished in a two step process. In a

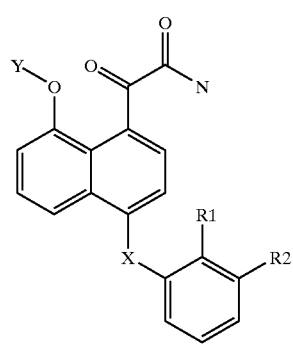

(Ik)

wherein:

R$^1$ and R$^2$ are each independently hydrogen or a non-interfering substituent with the proviso that at least one of R$^1$ or R$^2$ must be hydrogen;

X is —CH$_2$— or —O—; and

Y is (CH$_2$)$_n$Z where n is a number from 1–3 and Z is an acid group selected from the group consisting of CO$_2$H, —SO$_3$H or —PO(OH)$_2$.

A specific suitable naphthyl glyoxamide sPLA$_2$ inhibitors useful in the method of the invention has the following structural formula:

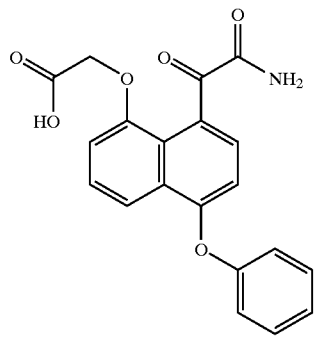

The naphthyl glyoxamide compounds are prepared as follows:

Compounds of formula I where X is oxygen can be prepared by the following reaction Scheme Ik.

Scheme Ik

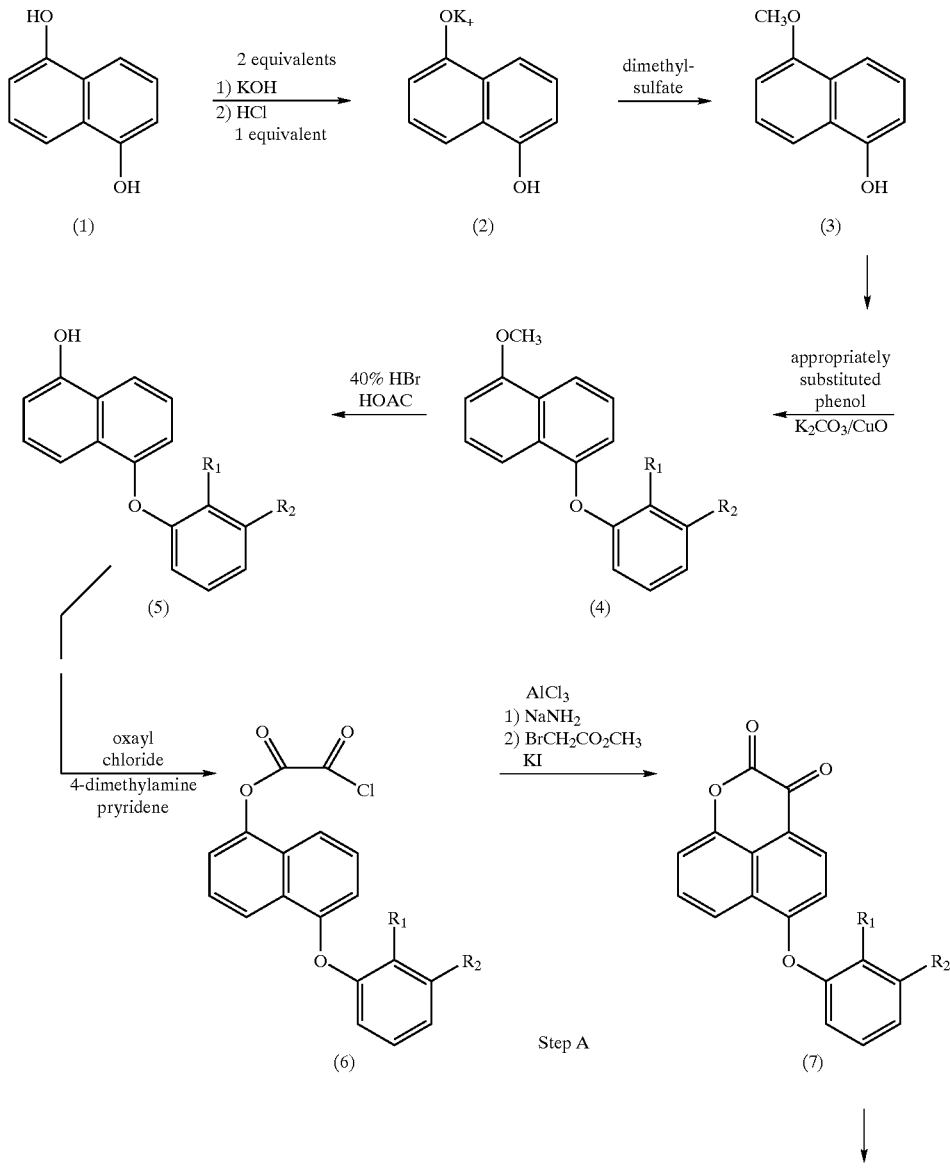

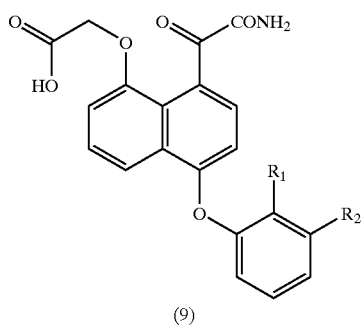 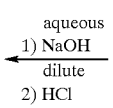 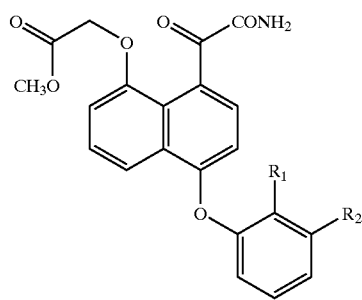

(9)    Step B    (8)

In the above depicted reaction scheme, the 1,5-dihydroxy napthalene starting material (1) is dispersed in water and then treated with 2 equivalents of potassium hydroxide. The resultant solution is chilled in an ice bath and one equivalent of a strong mineral acid, such as hydrochloric acid, is added to produce the potassium salt† (2).

Alkylation of the radical (2) can then be accomplished by treatment with a methylating agent such as dimethyl sulfate to prepare the ether (3).

Preparation of (4) is achieved by reacting the ether (3) with an appropriately substituted phenol in an Ullman-type reaction using potassium carbonate and cupric oxide.

De-methylation of (4) can be accomplished by treating (4) with a 40% HBr/HOAC solution at reflux in a protic polar solvent such as acetic acid, to prepare (5).

Reflux of compound (5) with oxalyl chloride and 4-demethylamino pyridine, in an alkylhalide solvent such as methylene chloride, prepares the oxalyl chloride (6).

Internal cyclization of (6) can be achieved under Friedel-Crafts condition using aluminum chloride or other similar metal halide as the catalyst. The reaction can be conveniently conducted in an alkyl halide solvent, such as 1,2-dichloroethane.

Alkylation and hydrolysis of the cyclized compound (7) can be achieved by reacting (7) with an alkaliamide base, such as sodium amide, followed by treatment with an alkylating agent, such as methyl bromoacetate, using potassium iodide as a catalyst.

Finally, the acid (9) is achieved by treating the ester (8) with an alkali base, such as aqueous sodium hydroxide, followed by treatment with a dilute aqueous mineral acid such as hydrochloric acid The acid compound (9) is then extracted with an organic solvent such as ethyl acetate.

The final product (9) can be purified using standard recrystallization procedures in a suitable organic solvent such as methylene chloride/hexane.

Compounds of formula I where X is methylene can be prepared as shown in the following Scheme IIk Scheme IIk

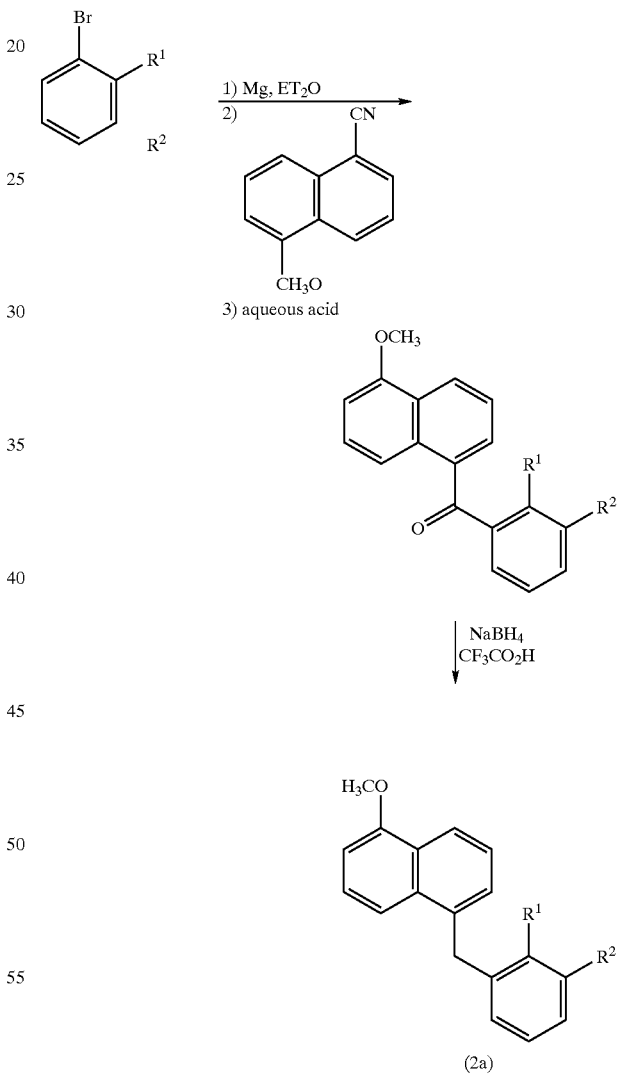

Using an appropriately substituted phenyl bromide, a Grignard reagent is prepared. The phenyl Grignard is then reacted with 4-methoxy naphthylnitrile and the resultant compound is hydrolyzed with a dilute acid such as hydrochloric acid to form the benzoyl naphthylene compound (1a).

Reduction of (1a) to form compound (2a) is accomplished by treatment with a reducing agent such as sodium borohydride. The reaction is conducted in a solvent-catalyst such as trifluoroacetic acid and initiated in an ice bath which is allowed to warm to room temperature as the reaction proceeds.

The desired naphthyl glyoxamide may then be prepared from (2a) according to the procedure in Scheme I starting with the chloromethylation step.

It will be readily appreciated by a person skilled in the art that the substituted benzyl bromide, substituted phenol and substituted naphthylnitrile compounds of Schemes I and II are either commercially available or can be readily prepared by known techniques from commercially available starting materials.

1) Phenyl acetamide sPLA$_2$ inhibitors and methods of making them are disclosed in U.S. patent application Ser. No. 08/976,858, filed Nov. 24, 1997 (titled, "Phenyl Acetamides as sPLA$_2$ Inhibitors"), the entire disclosure of which is incorporated herein by reference.

The method of the invention is for treatment of a mammal, including a human, afflicted with cystic fibrosis, said method comprising administering to said human a therapeutically effective amount of a phenyl acetamide sPLA$_2$ inhibitor represented by formula (Il) as follows:

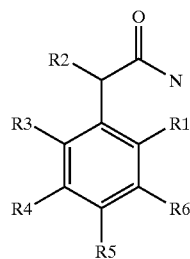

(Il)

wherein:
$R^1$ is —H or —O(CH$_2$)$_n$Z;
$R^2$ is —H or —OH;
$R^3$ and $R^4$ are each independently —H, halo or —(C$_1$–C$_4$) alkyl;
One of $R^5$ and $R^6$ is —YR$^7$ and the other is —H, where Y is —O— or —CH$_2$— and $R^7$ is phenyl or phenyl substituted with one or two substituents selected from the group consisting of halo, —(C$_1$–C$_4$)alkyl, (C$_1$–C$_4$) alkoxy, phenyl or phenyl substituted with one or two halo groups;
Z is —CO$_2$R, —PO$_3$R$_2$ or —SO$_3$R where R is —H or —(C$_1$–C$_4$)alkyl; and
n is 1–8;
or a pharmaceutically acceptable salt, racemate or optical isomer thereof;
provided that when $R^6$ is YR$^7$, $R^1$ is hydrogen; and
when $R^1$, $R^2$, $R^3$, $R^4$ and $R^6$ are hydrogen and $R^5$ is YR$^7$ where Y is —O—, $R^7$ cannot be phenyl; and
when $R^1$, $R^2$, $R^3$, $R^4$ and $R^6$ are hydrogen, $R^5$ is YR$^7$ where Y is CH$_2$, $R^7$ cannot be phenyl substituted with one methoxy or two chloro groups.

Preferred suitable phenyl acetamide sPLA$_2$ inhibitors useful in the method of the invention are as follows:

Compounds of formula I wherein $R^2$, $R^3$ and $R^4$ is H, Y is oxygen or CH$_2$, $R^7$ is phenyl or phenyl substituted at the meta position with one or two substituents selected from halo, —(C$_1$–C$_4$)alkyl, (C$_1$–C$_4$)alkoxy, phenyl or phenyl substituted with halo and n is 4–5.

A specific suitable phenyl acetamide sPLA$_2$ inhibitors useful in the method of the invention is 2-(4-carboxybutoxy)-4-(3-phenylphenoxy)phenylacetamide.

The phenyl acetimde compounds are prepared as follows:
Compounds of formula I where $R^1$ and $R^2$ are H, $R^5$ or $R^6$ are YR$^7$ where $R^7$ is phenyl or substituted phenyl and Y is oxygen can be prepared as illustrated in Scheme Il(a), below.

Scheme Il(a)

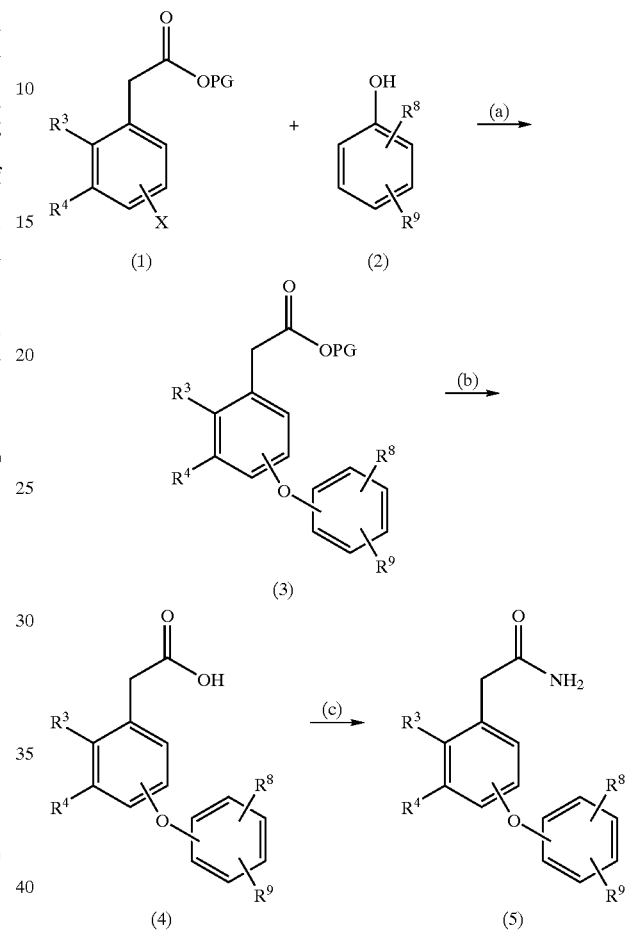

X is halo;
$R^8$ and $R^9$ are each independently —H, halo, —(C$_1$–C$_4$) alkyl, (C$_1$–C$_4$)alkoxy, phenyl or phenyl substituted with one or two halo groups; and
PG is a carboxyl protecting group An appropriately substituted carboxy-protected halophenyl compound (1), where the halogen is preferably bromine, is coupled with an appropriately substituted phenol (2) under modified Ullmann conditions, by refluxing with potassium carbonate and cupric oxide in an aprotic polar solvent, such as pyridine, under an inert gas such as argon. The reaction is substantially complete in 1–24 hours.

Intermediate (3) is deprotected by treatment with a base such as aqueous potassium hydroxide using a solvent, such as diethylene glycol. The reaction, preferably conducted at about 100°–150° C., is substantially complete in 1–24 hours.

Conversion to the amide (5) can then be readily achieved by treatment first with oxalyl chloride in an alkyl halide solvent, such as methylene chloride, using dimethylformamide as a catalyst, at temperatures of from about 0° C. to ambient temperature, followed by treatment with an excess of ammonia gas, again in an alkyl halide solvent.

Alternately, compounds of formula I can be prepared according to the procedure of Scheme I(b), below.

The substituted phenol (2) is coupled with an appropriately substituted benzyl halide (6) as described in Scheme I(a), step a, above, to prepare (7).

Halogenation of (7) is achieved using a halogenating agent, such as N-bromosuccinimide and a catalyst, such as 2,2'azobisisobutyronitrile, in an alkyl halide solvent, such as chloroform, to prepare (8).

Treatment of (8) with sodium cyanide in an aprotic polar solvent, such as dimethyl formamide produces the nitrile (9) which can then be readily converted to the amide (10) by treatment with an aqueous acid, such as hydrochloric acid.

Scheme II(b)

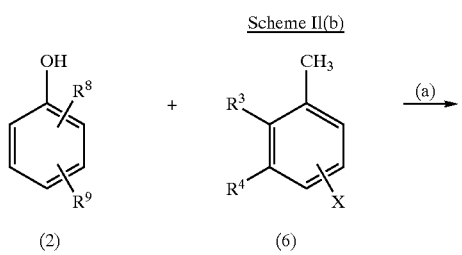

(2)   (6)

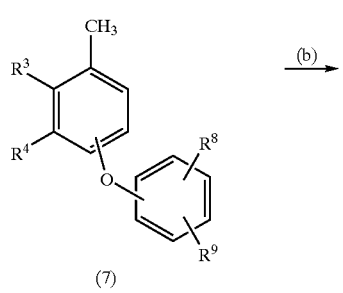

(7)

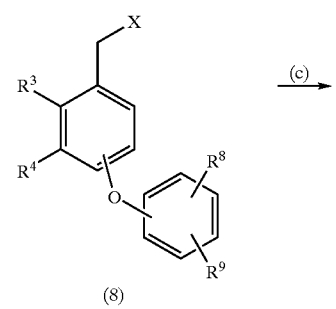

(8)

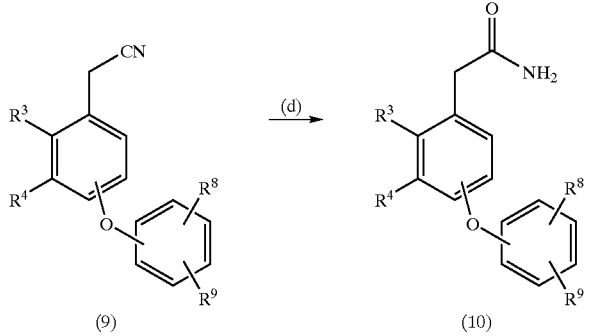

(9)   (10)

$R^8$ and $R^9$ are as shown in Scheme I(a),

X is halo.

In another procedure, compounds of formula I where $R^1$, $R^2$, $R^3$ and $R^4$ are hydrogen, Y is —O— or —$CH^2$— and $R^7$ is phenyl can be prepared as portrayed in Scheme III.

Scheme III

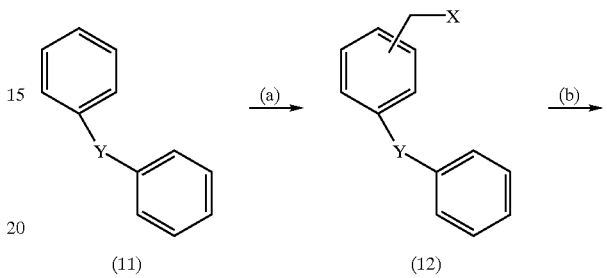

(11)   (12)

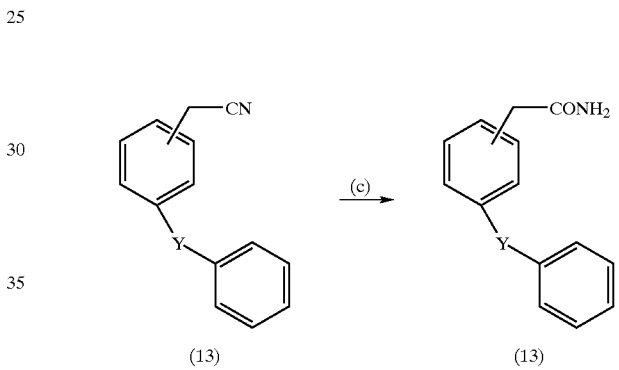

(13)   (13)

X is a halogen.

An appropriate diphenyl compound (11) is treated with paraformaldehyde and a halogenating agent, such as 40% hydrogen bromide in acetic acid. Two positional isomers result with the X substituent at either the meta or para position of the phenyl ring to which it is attached.

Displacement of the halogen to prepare the nitrile isomers (13) can be achieved by treatment of (12) with sodium cyanide in dimethylformamide as described in Scheme†I(b), step (c), above. The isomers can then be readily separated by conventional chromatographic techniques and each isomer may be converted to its respective amide (14) by treatment with hydrogen peroxide and potassium carbonate in an aprotic polar solvent, such as dimethylsulfoxide.

Compounds where $R^1$ is —O(CH$_2$)$_n$Z can be prepared as illustrated in Scheme IIII, below.

Scheme IIIl
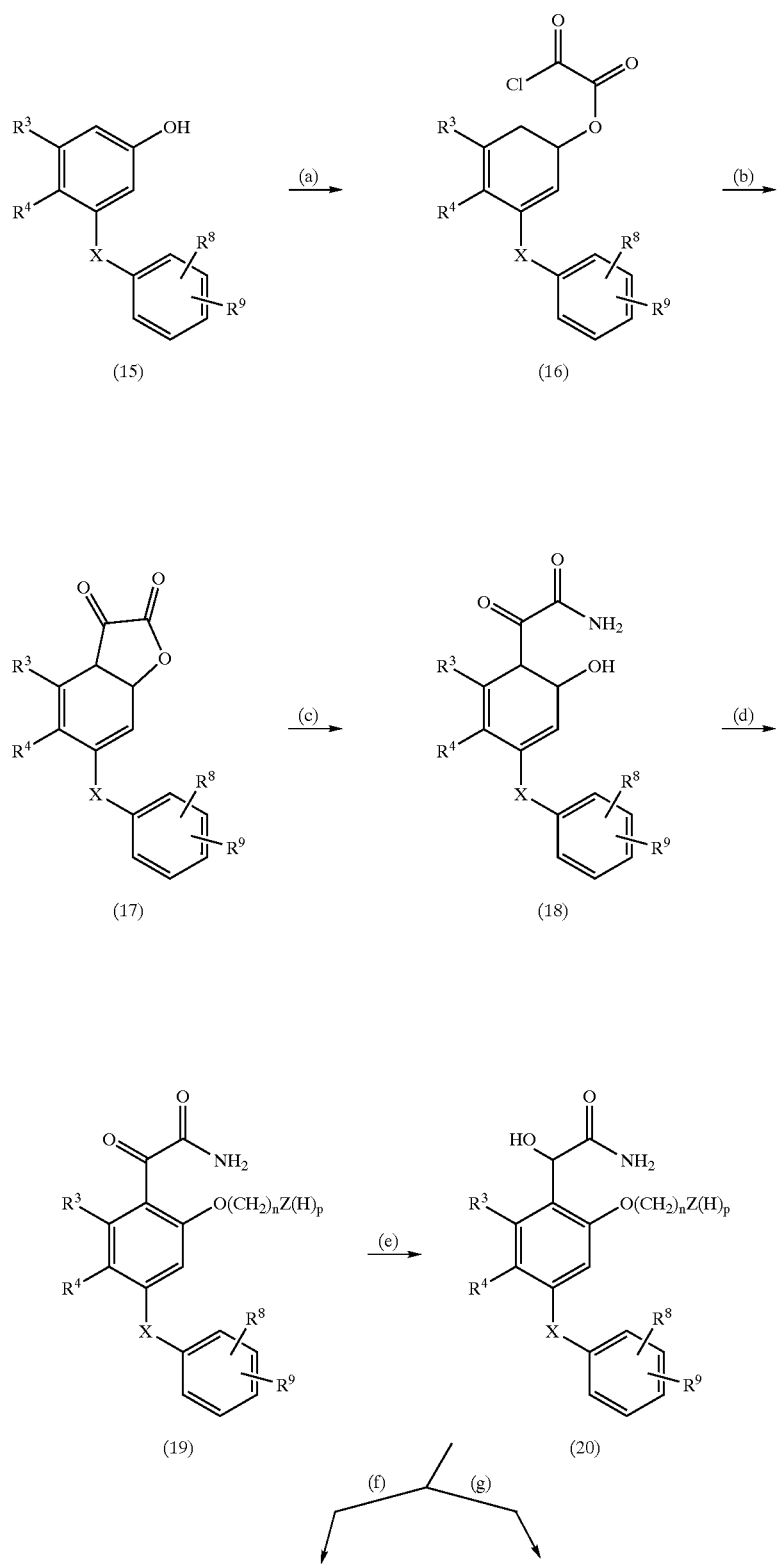

-continued

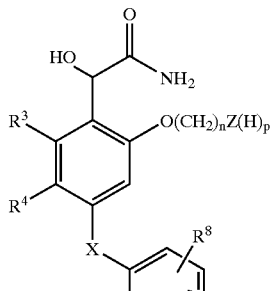
(21)

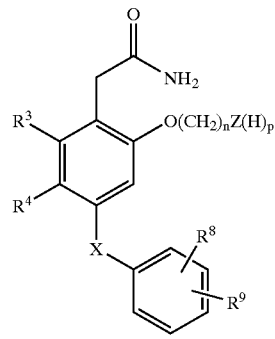
(22)

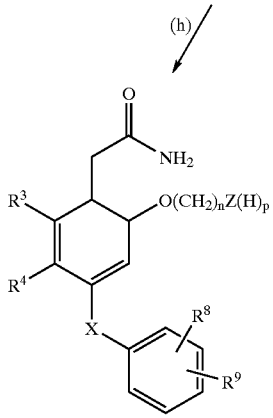
(23)

R is —(C₁–C₄)alkyl and
p=1 or 2.

Intermediate (16) is prepared by refluxing an appropriately substituted diphenyl compound (15) with oxalyl chloride in an alkyl halide solvent, such as chloroform. Preferably the reaction is catalyzed with 4,4-N-dimethylaminopyridine.

Cyclization to the lactone (17) can be achieved under Friedel-Crafts conditions using a suitable metal halide, such as aluminum chloride, as the catalyst. Conversion to the glyoxamide (18) can be achieved by aminolysis of the lactone ring using concentrated ammonium hydroxide.

Alkylation of the hydroxy group to prepare the desired alkyl-linked ester (19) occurs by treatment of (18) with an appropriate alkylating agent, such as (X)(CH₂)ₙB where B is CO₂PG, —PO₃PG or —SO₃PG, X is halo and PG is an acid protecting group, preferably methyl.

Partial reduction of the carbonyl in the glyoxamide (19) is achieved by treatment with a suitable reducing agent, such as sodium borohydride in methanol, preferably at temperatures of from 0°–20° C., to prepare the intermediate (20). The desired acid or acid salt (21) can be accomplished by treatment with a suitable base, such as sodium hydroxide.

Further reduction of intermediate (20) can be achieved by treatment with triethylsilane in a strong acid, such as trifluoroacetic acid, under an inert gas, such as argon, to prepare (22) followed, again, by conversion to the acid or salt (23) with a strong base.

m) Naphthyl acetamide sPLA₂ inhibitors and the method of making them are described in U.S. patent application Ser. No. 09/091,077, filed Dec. 9, 1996 (titled, "Benzyl naphthalene sPLA₂ Inhibitors"), the entire disclosure of which is incorporated herein by reference.

The method of the invention is for treatment of a mammal, including a human, afflicted with cystic fibrosis, said method comprising administering to said human a therapeutically effective a naphthyl acetamide sPLA₂ inhibitor represented by formula (Im) as follows:

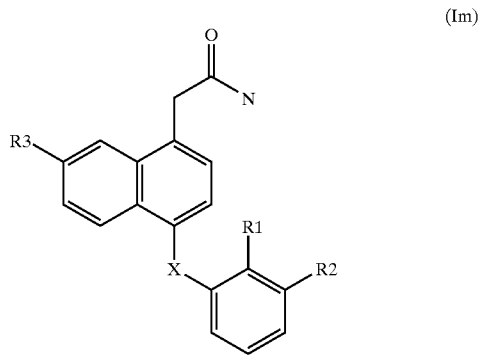
(Im)

wherein:

R¹ and R² are each independently hydrogen or a non-interfering substituent with the proviso that at least one of R¹ and R² must be hydrogen;

$R^3$ is hydrogen, —O(CH$_2$)$_n$Y,

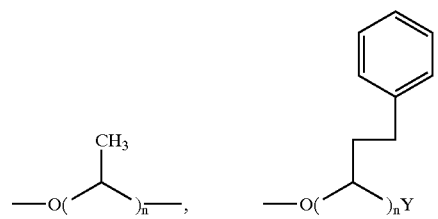

where n is from 2 to 4 and Y is —CO$_2$H, —PO$_3$H$_2$ or SO$_3$H; and

X is —O— or —CH$_2$—.

Compounds where X is oxygen can be prepared by the following Scheme Im.

In the first step of the above reaction scheme, an appropriately substituted 1-bromo-4-methylnapthalene and an appropriately substituted phenol are dissolved in an aprotic polar solvent such as pyridine. The mixture is treated with an excess of potassium carbonate and an excess of copper-bronze and refluxed under a nitrogen blanket to produce (1).

Bromination of compound (1) to produce (2) is accomplished by refluxing (1) with a brominating agent, such as N-bromosuccinamide, in a non-polar alkyl halide solvent, such as carbon tetrachloride, using 2,2-azobisisobutyronitrile as a catalyst.

Treatment of (2) with sodium cyanide produces (3). This reaction is best conducted in an aprotic polar solvent, such as dimethyl sulfoxide (DMSO), while heating to a temperature of about 60° C.

Hydrolysis of the cyano compound (3) to produce the acid (4) is accomplished in two steps. Using a polar protic solvent, such as diethylene glycol as a cosolvent, the cyano compound (3) is treated with an alkali metal base, such as potassium hydroxide, and the mixture is heated to about Scheme Im

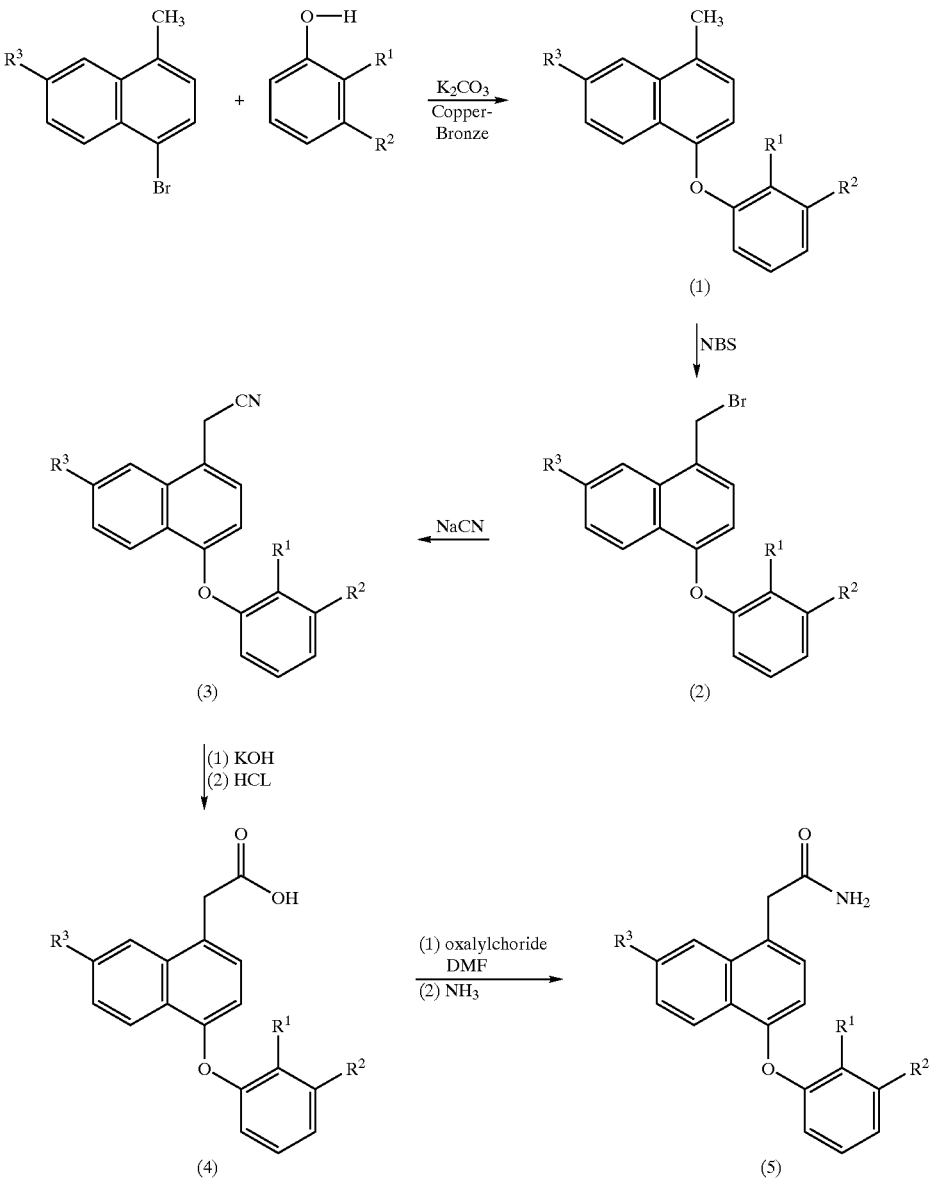

90–95° C. The resultant product is then reacted with a strong mineral acid such as hydrochloric acid.

Conversion of (4) to the desired naphthyl acetamide compound (5) is accomplished by another two-step process. First, the acid (4) is dissolved in an alkyl halide solvent such as methylene chloride. The acid/alkyl halide solution is chilled in an ice bath then treated with oxalyl chloride, using dimethylformamide (DMF) as a catalyst, to produce the acid chloride. The solution is allowed to warm to room temperature and then treated with ammonia gas at room temperature to produce (5).

The desired product (5) can be purified using standard recrystallization procedures in a suitable organic solvent, preferably methylene chloride/hexane.

Compounds where X is methylene can be prepared by the following Scheme IIm

Compound (1a) is prepared by a grignard reaction. The Grignard reagent starting material is prepared by reacting an appropriately substituted phenyl bromide with magnesium and ether. The reagent is then reacted with an appropriately substituted naphthyl nitrile and the resultant compound is hydrolyzed with an aqueous acid such as hydrochloric acid to form the benzoyl napthyl (1a).

Reduction of (1a) is accomplished by treatment with a molar excess of a reducing agent such as sodium borohydride. The reaction is initiated in an ice bath using a solvent-catalyst such as trifluoroacetic acid and then allowed to warm to room temperature as the reduction proceeds.

Chloromethylation of (2a) is achieved by treatment with an excess of formaldehyde and concentrated hydrochloric acid in a polar acidic solvent such as an acetic/phosphoric acid mixture. The reaction is best conducted at a temperature of about 90° C.

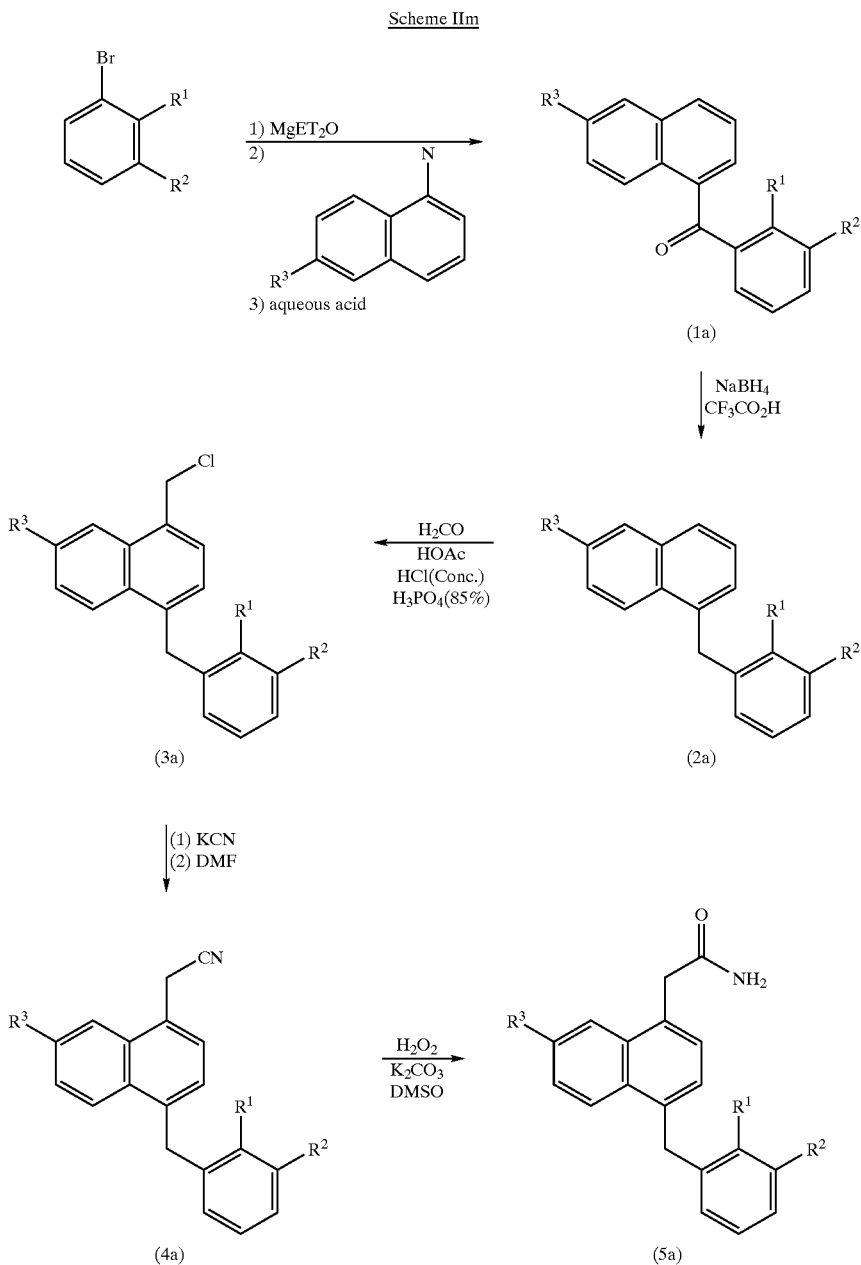

Scheme IIm

The nitrile 4(a) is prepared by a nucleophilic displacement of the chloride compound (3a) with cyanide. The reaction is conducted by refluxing (3a) with a slight molar excess in an aprotic polar solvent of sodium cyanide such as dimethylformamide (DMF) for about five hours, then allowing the reaction to continues while it cools to room temperature.

The desired naphthylamide (5a) is then prepared from the nitrile (4a) in a three-step process. To a solution of nitrile (4a), dissolved in an aprotic polar solvent such as DMSO, potassium carbonate is added to make the nitrite solution slightly basic. Hydrolysis of the nitrile is then achieved by treatment with an aqueous hydrogen peroxide solution. Crystallization of the naphthyl acetamide may be accomplished by adding water to the peroxide solution.

Compounds where $R^3$ is other than hydrogen can be readily prepared by using a 1-bromo-4-methyl-napthalene with a protected phenol, such as a methoxy group, on the 6-position of the napthalene ring as a starting material. The process is conducted, as described above, to prepare compounds (1)–(3). Acid hydrolysis of the cyano group (3) and deprotection of the protected phenol can be accomplished by treating (3) with a 40% hydrogen bromide solution in acetic acid. The deprotected phenol can then be reacted to prepare the appropriate substituent at the 6-position of the napthyl ring. For example, preparation of compounds where $R^3$ is —O(CH$_2$)$_n$COOH can be achieved by alkyalting the phenol with an appropriate alkyl halide followed by conversion to the acid by treatment with a base such as aqueous sodium hydroxide followed by dilute hydrochloric acid.

It will be readily appreciated by one skilled in the art that the substituted phenol and phenyl bromide starting materials are either commercially available or can be readily prepared by known techniques from commercially available starting materials. All other reactants and reagents used to prepare the compounds of the present invention are commercially available.

FORMULATIONS SUITABLE FOR USE IN THE METHOD OF THE INVENTION

The sPLA$_2$ inhibitors used in the method of the invention may be administered to treat cystic fibrosis by any means that produces contact of the active agent with the agent's site of action in the human body. They can be administered by any conventional means available for use in conjunction with pharmaceuticals, either as individual therapeutic agents or in a combination of therapeutic agents. The sPLA$_2$ inhibitors can be administered alone, but are generally administered with a pharmaceutical carrier selected on the basis of the chosen route of administration and standard pharmaceutical practice.

Suitable formulations are those comprising a therapeutically effective amount of sPLA$_2$ inhibitor together with a pharmaceutically acceptable diluent or carrier, the composition being adapted for the particular route of administration chosen. By "pharmaceutically acceptable" it is meant the carrier, diluent or excipient must be compatible with the sPLA$_2$ inhibitor ("active compound") in the formulation and not deleterious to the subject being treated.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the sPLA$_2$ inhibitor is mixed with a carrier having the necessary binding properties in suitable proportions and compacted in the shape and size desired. The powders and tablets preferably contain from about 1 to about 99 weight percent of the sPLA$_2$ inhibitor.

Sterile liquid form formulations include suspensions, emulsions, syrups and elixirs. The active compound can be dissolved or suspended in a pharmaceutically acceptable carrier, such as sterile water, saline, dextrose solution, sterile organic solvent or a mixture of both.

The active compound can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray or lung inhaler. It can also be administered topically as an ointment, cream, gel, paste, lotion, solution, spray, aerosol, liposome, or patch. Dosage forms used to administer the active compound usually contain suitable carriers, diluents, preservatives, or other excipients, as described in Remington's Pharmaceutical Sciences, Mack Publishing Company, a standard reference text in the field.

Gelatin capsules may be prepared containing the active compound and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

For parenteral and intravenous solutions, water, a suitable oil, saline, aqueous dextrose (glucose), and related sugar solutions and glycols such as propylene glycol or polyethylene glycols are suitable carriers for parenteral solutions. Solutions for parenteral administration contain the active compound, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Topical ointments, creams, gels, and pastes contain with the active compound diluents such as waxes, paraffins, starch, polyethylene glycol, silicones, bentonites, silicic acid, animal and vegetable fats, talc and zinc oxide or mixtures of these or other diluents.

Topical solutions and emulsions can, for example, contain with the active compound, customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or anti-oxidizing agents.

Powders and sprays can contain along with the active compound, the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active compound can be incorporated.

For inhalation administration, the sPLA$_2$ inhibitor or formulations containing the inhibitor can be dissolved or dispersed in liquid form, such as in water or saline, preferably at a concentration at which the composition is fully solubilized and at which a suitable dose can be administered within an inhalable volume. A nebulizer (e.g., De Vilbiss 646) and compressed air generator (Pulmoaide, DeVilbiss) can be used to nebulize and deliver the compound or formulation containing the compound to the airway surfaces once or several times a day, as required. For infants, the dose may be adjusted proportionately for size or body weight.

Formulations containing compounds of the invention may be administered through the skin by an appliance such as a transdermal patch. Patches can be made of a matrix such as polyacrylamide and a semipermeable membrane made from a suitable polymer to control the rate at which the material is delivered to the skin. Other suitable transdermal patch formulations and configurations are described in U.S. Pat. Nos. 5,296,222 and 5,271,940, the disclosures of which are incorporated herein by reference. Lipophilic prodrug derivatives of the sPLA$_2$ inhibitors are particularly well suited for transdermal absorption administration and delivery systems.

Formulations within the scope of this invention include the admixture of sPLA$_2$ inhibitor with a therapeutically effective amount of any therapeutically effective co-agents for cystic fibrosis such as N-acetyl-cysteine, human recombinant DNAse, antibiotics, etc., as set out in the section "CO-AGENT—COMBINED THERAPY", infra.

Formulations used for facilitating lung mucus clearance in a human afflicted with cystic fibrosis may further comprise the step of concurrently administering a sodium channel blocker such as amiloride to the subject in an amount effective to inhibit the reabsorption of water from lung mucus membranes.

For all of the above formulations the preferred active compound are the 1H-indole-3-glyoxylamide compounds as previously described and methods of making as described in U.S. Pat. No. 5,654,326 (the disclosure of which is incorporated herein by reference). Most preferred compounds within the general class of 1H-indole-3-glyoxylamides are ((3-(2-amino-1,2-dioxoethyl)-2-ethyl-1-(phenylmethyl)-1H-indol-4yl)oxy)acetic acid, sodium salt; and 1H-indole-3-glyoxylamides are ((3-(2-amino-1,2-dioxoethyl)-2-ethyl-1-(phenylmethyl)-1H-indol-4yl)oxy)acetic acid, methyl ester.

PROPORTION AND WEIGHT OF ACTIVE COMPOUNDS USED IN THE METHOD OF THE INVENTION

The 1H-indole-3-glyoxylamide compound may be used at a concentration of 0.1 to 99.9 weight percent of the formulation.

Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Compositions (dosage forms) suitable for internal administration contain from about 1 milligram to about 500 milligrams of active compound per unit. In these pharmaceutical compositions the active compound will ordinarily be present in an amount of about 0.5–95% by weight based on the total weight of the composition.

Examples of useful pharmaceutical compositions and their proportions of ingredients are illustrated as follows:

Capsules

Capsules may be prepared by filling standard two-piece hard gelatin capsules each with 50 mg of powdered active compound, 175 mg of lactose, 24 mg of talc, and 6 mg of magnesium stearate.

Soft Gelatin Capsules

A mixture of active compound in soybean oil is prepared and injected by means of a positive displacement pump into gelatin to form soft gelatin capsules containing 50 mg of the active compound. The capsules are washed in petroleum ether and dried.

Tablets

Tablets may be prepared by conventional procedures so that the dosage unit is 50 mg of active compound, 6 mg of magnesium stearate, 70 mg of microcrystalline cellulose, 11 mg of cornstarch, and 225 mg of lactose. Appropriate coatings may be applied to increase palatability or delay absorption.

Suspensions

An aqueous suspension is prepared for oral administration so that each 5 ml contain 25 mg of finely divided active compound, 200 mg of sodium carboxymethyl cellulose, 5 mg of sodium benzoate, 1.0 g of sorbitol solution, U.S.P., and 0.025 mg of vanillin.

Injectables

A parenteral composition suitable for administration by injection is prepared by stirring 1.5% by weight of active compound in 10% by volume propylene glycol and water. The solution is sterilized by commonly used techniques.

Nasal Spray

An aqueous solution is prepared such that each 1 ml contains 10 mg of active compound, 1.8 mg methylparaben, 0.2 mg propylparaben and 10 mg methylcellulose. The solution is dispensed into 1 ml vials. The active compound may be used at a concentration of 0.1 to 99.9 weight percent of the formulation.

Aerosol formulations are capable of dispersing into particle sizes of from about 0.5 to about 10 microns and have sufficient sPLA2 inhibitor to achieve concentrations of the inhibitor on the airway surfaces of from about $10{-}10$ to $10^{-2}$ moles per liter.

THE PRACTICE OF THE METHOD OF THE INVENTION

The use of sPLA$_2$ inhibitors in the method of the invention prevents progressive deterioration of lung tissue and lung function by inhibiting or reducing the degree of inflammation which may be a primary pathologic process in cystic fibrosis. The method of the invention is preferably used early in the life of the patient afflicted with cystic fibrosis, most preferably in a child just after diagnosis of cystic fibrosis.

The method of the invention can be practiced using pharmaceutical formulations containing sPLA$_2$ inhibitors (preferably, sPLA$_2$ inhibitors taught to be preferred in this specification) or formulations containing such sPLA$_2$ inhibitors as taught in the preceding section.

The underlying cause of cystic fibrosis will not be prevented by the method of this invention, but symptoms will be reduced in severity or extent ameliorated by administration of sPLA$_2$ inhibitors (and their formulations).

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active compound can be about 0.1 to 200 milligrams per kilogram of body weight. Ordinarily 0.5 to 50, and preferably 1 to 25 milligrams per kilogram per day given in divided doses 1 to 6 times a day or in sustained release form is effective to obtain desired results.

In general, the sPLA$_2$ inhibitor will be administered to a human so that a therapeutically effective amount is received. A therapeutically effective amount may coventionally be determined for an individual patient by administering the active compound in increasing doses and observing the effect on the patient, for example, reduction in the amount of daily sputum production, improvement in lung function as assessed by standard pulmonary function listing, improvement in exercise, reduction in frequency of bacterial infections, or a reduction in other symptoms associated with cystic fibrosis.

The exact amount of sPLA2 inhibitor required for preventing or treating the symptoms of cystic fibrosis (or other indications listed in the "Summary of the Invention", supra.) will vary from person to person, depending on the age and general condition of the subject and the severity of the disease, mode of administration, etc. An appropriate amount may be determined by one of ordinary skill by judging the effective elimination, reduction, or prevention of symptoms associated with cystic fibrosis (e.g., lung mucus clearance).

Generally, the compound must be administered in a manner and a dose to achieve in the human a blood level concentration of sPLA$_2$ inhibitor of from 10 to 3000 nanograms/ml, and preferably a concentration of 100 to 800 nanograms/ml.

The treatment regimen for many cystic firbosis may stretch over many days to months or to years. Oral dosing is preferred for patient convenience and tolerance. With oral dosing, one to four oral doses per day, each from about 0.01 to 25 mg/kg of body weight with preferred doses being from about 0.1 mg/kg to about 2 mg/kg.

Parenteral administration (particularly, intravenous administration) is often preferred in instances where rapid alleviation of patient distress is required. With parenteral administration doses of 0.01 to 100 mg/kg/day administered continuously or intermittently throughout the day may be used. For parenteral administation, the comound may be administered in a physiologic saline vehicle (e.g., 0.9% normal saline, 0.45% normal saline, etc.) a dextrose vehicle (e.g., 5% dextrose in water), or a combination of saline and dextrose vehicle (0.9% normal saline in 5% dextrose).

Inhalation therapy also may be useful either alone or as an adjunct to other routes of administration. With inhalation therapy, doses necessary to produce a decrease in the clinical symptoms of cystic fibrosis are readily determined and used.

Co-Agent—Combined Therapy

The sPLA$_2$ inhibitor (viz., active compound in a formulation of the invention) can also be administered in the method of the invention in combination with another pharmacologically active agent known to have utility for alleviating the symptoms of cystic fibrosis. For example, the sPLA2 inhibitors taught herein may be combined with the following therapeutic agents:

1. Agents for increasing mucus clearance
   a. N-acetyl-cysteine
2. Agents that DNA in cystic fibrosis sputum
   a. human recombinant DNAse
3. Drugs for restoring water and salt content
   a. amiloride
   b. triphosphate nucleotides
4. Agents that control lung infection
   a. antibiotics
      (i) penicillins
      (ii) cephalosporins, ceftazadime
      (iii) aminoglycosides
5. Inhaled drugs
   a. beta-adrenergic agonists
   b. anticholinergics
6. Oral Steroids
7. Pancreatic enzymes
8. Gene Therapy Testing Methods for Cystic Fibrosis The diagnostic criteria for cystic fibrosis are those found in standard medical references (e.g., Harrison's Principles of Internal Medicine, thirteenth ed., 1994, by McGraw-Hill, Inc., ISBN 0-07-032370-4, pgs., 1194–1197). These criteria may be used to determine when to begin using the method of the invention, the frequency and degree of treatment, and the time for cessation of treatment.

The cystic fibrosis patient having lung disease may be evaluated with any conventional measure of lung capacity, nature of extent of sputum, and etc.

The cystic fibrosis patient having gastointestinal disease may be evaluated by conventional criteria for adaquate nutrition.

While the present invention has been illustrated above by certain specific embodiments, these are not intended to limit the scope of the invention as described in the appended claims.

I claim:

1. A method for treatment of a human currently afflicted with cystic fibrosis, said method comprising administering to said human in need of such treatment a therapeutically effective amount of a 1H-indole-3-glyoxylamide compound represented by the formulae:

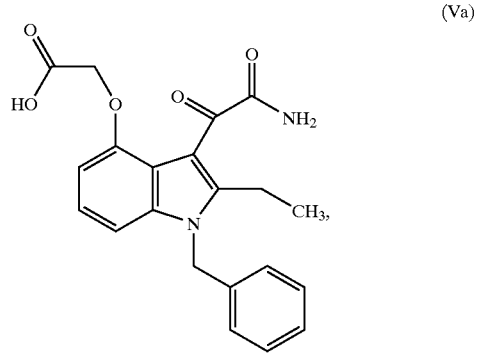

(Va)

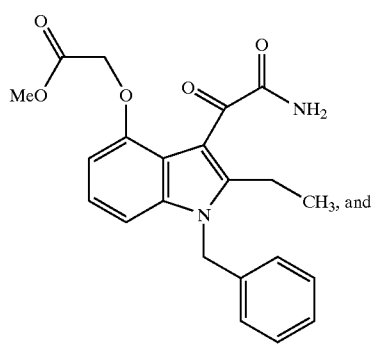
(Vb)
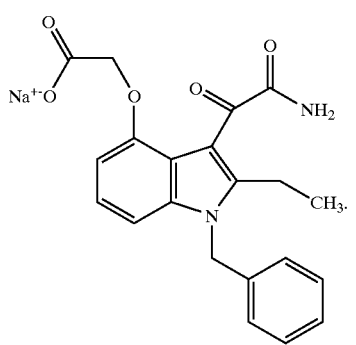
(Vc)
* * * * *